(12) United States Patent
Severini et al.

(10) Patent No.: US 9,096,910 B2
(45) Date of Patent: Aug. 4, 2015

(54) SET OF PROBES FOR THE DETECTION AND TYPING OF 46 HUMAN PAPILLOMAVIRUS MUCOSAL TYPES

(76) Inventors: Alberto Severini, Winnipeg (CA); Vanessa Goleski, Winnipeg (CA)

(*) Notice: Subject to any disclaimer, the term of this patent is extended or adjusted under 35 U.S.C. 154(b) by 238 days.

(21) Appl. No.: 13/522,348

(22) PCT Filed: Jan. 29, 2011

(86) PCT No.: PCT/CA2011/050026
§ 371 (c)(1),
(2), (4) Date: Oct. 23, 2012

(87) PCT Pub. No.: WO2011/088573
PCT Pub. Date: Jul. 28, 2011

(65) Prior Publication Data
US 2013/0143751 A1 Jun. 6, 2013

Related U.S. Application Data

(60) Provisional application No. 61/296,245, filed on Jan. 19, 2010.

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |
| *C12Q 1/70* | (2006.01) |

(52) U.S. Cl.
CPC ..................................... *C12Q 1/708* (2013.01)

(58) Field of Classification Search
CPC .............. C12Q 1/708; C12Q 1/6886; C12Q 2565/629; C12Q 1/686; C12Q 1/6846; C12Q 2525/121; C12Q 1/6883; C12Q 1/689; C12Q 2525/186; C12Q 2525/313; C12Q 2537/143; C12Q 2600/158; C12Q 1/6818; C12Q 1/6834; C12Q 2525/204; C12Q 2531/113; C12Q 2561/113; C12Q 2523/109; C12Q 2525/155; C12Q 2527/107; C12Q 2563/179
See application file for complete search history.

(56) References Cited

U.S. PATENT DOCUMENTS

| | | | |
|---|---|---|---|
| 2005/0175987 A1* | 8/2005 | Jansen et al. | 435/5 |
| 2007/0031826 A1* | 2/2007 | Lee et al. | 435/5 |
| 2010/0279888 A1* | 11/2010 | Park et al. | 506/9 |

FOREIGN PATENT DOCUMENTS

WO    WO 2011/073183    *    6/2011

OTHER PUBLICATIONS

Oh (Journal of Clinical Microbiology vol. 42 No. 7 Jul. 2004 pp. 3272-3280).*
Jiang (Journal of Medical Microbiology 2006 vol. 55 pp. 715-720).*
GenBank (Accession DQ080080 GI 71726694 May 31, 2006).*
Klaassen (Journal of Clinical Microbiology May 2004 vol. 42 No. 5 pp. 2152-2160).*
Boyers (J Clin Microbiol 2007 vol. 45 No. 6 pp. 1874-1883).*

* cited by examiner

*Primary Examiner* — Amanda Haney
(74) *Attorney, Agent, or Firm* — Michael R. Williams; Ade & Company Inc.

(57) ABSTRACT

We have developed a set of probes to detect and identify 46 types of mucosal human papillomaviruses (HPV). These probes recognize the variable region comprised between the 2 conserved regions of the published GP5+/GP6+ set of PCR primers. The 46 probes have been shown to hybridize, as intended, to the DNA derived from the following HPV types: 6, 11, 13, 16, 18, 26, 30, 31, 32, 33, 35, 39, 40, 42, 43, 44, 45, 51, 52, 53, 54, 56, 58, 59, 61, 62, 66, 67, 68, 69, 70, 71, 72, 73, 74, 81, 82, 83, 84, 85, 86, 87, 89, 90, 91 and 97. The hybridization of each probe is specific for each type without any cross hybridization among types and it is sensitive enough to allow detection of PCR products for genotyping of HPV DNA contained in clinical samples.

6 Claims, 5 Drawing Sheets

Fig. 2

| # | Type | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| 4 | +HPV16 | + | + | + | + | - | - | - | - | - | - | - | - | - | - | - | - | - | - | - | - | - | - | - | - | - | - | - | - | - | - | - | - | - | - | - | - | - | - | - | - |
| 5 | +HPV 18 | + | + | + | + | + | - | - | - | - | - | - | - | - | - | - | - | - | - | - | - | - | - | - | - | - | - | - | - | - | - | - | - | - | - | - | - | - | - | - | - |
| 6 | +HPV 26 | + | + | + | + | + | + | - | - | - | - | - | - | - | - | - | - | - | - | - | - | - | - | - | - | - | - | - | - | - | - | - | - | - | - | - | - | - | - | - | - |
| 7 | +HPV 30 | + | + | + | + | + | + | + | - | - | - | - | - | - | - | - | - | - | - | - | - | - | - | - | - | - | - | - | - | - | - | - | - | - | - | - | - | - | - | - | - |
| 8 | +HPV 31 | + | + | + | + | + | + | + | + | - | - | - | - | - | - | - | - | - | - | - | - | - | - | - | - | - | - | - | - | - | - | - | - | - | - | - | - | - | - | - | - |
| 9 | +HPV 32 | + | + | + | + | + | + | + | + | + | - | - | - | - | - | - | - | - | - | - | - | - | - | - | - | - | - | - | - | - | - | - | - | - | - | - | - | - | - | - | - |
| 10 | +HPV 33 | + | + | + | + | + | + | + | + | + | + | - | - | - | - | - | - | - | - | - | - | - | - | - | - | - | - | - | - | - | - | - | - | - | - | - | - | - | - | - | - |
| 11 | +HPV 35 | + | + | + | + | + | + | + | + | + | + | + | - | - | - | - | - | - | - | - | - | - | - | - | - | - | - | - | - | - | - | - | - | - | - | - | - | - | - | - | - |
| 12 | +HPV 39 | + | + | + | + | + | + | + | + | + | + | + | + | - | - | - | - | - | - | - | - | - | - | - | - | - | - | - | - | - | - | - | - | - | - | - | - | - | - | - | - |
| 13 | +HPV 40 | + | + | + | + | + | + | + | + | + | + | + | + | + | - | - | - | - | - | - | - | - | - | - | - | - | - | - | - | - | - | - | - | - | - | - | - | - | - | - | - |
| 14 | +HPV 42 | + | + | + | + | + | + | + | + | + | + | + | + | + | + | -* | - | - | - | - | - | - | - | - | - | - | - | - | - | - | - | - | - | - | - | - | - | - | - | - | - |
| 15 | +HPV 43 | + | + | + | + | + | + | + | + | + | + | + | + | + | + | + | - | - | - | - | - | - | - | - | - | - | - | - | - | - | - | - | - | - | - | - | - | - | - | - | - |
| 16 | +HPV 45 | + | + | + | + | + | + | + | + | + | + | + | + | + | + | + | - | + | - | - | - | - | - | - | - | - | - | - | - | - | - | - | - | - | - | - | - | - | - | - | - |
| 17 | +HPV 51 | + | + | + | + | + | + | + | + | + | + | + | + | + | + | + | - | + | + | - | - | - | - | - | - | - | - | - | - | - | - | - | - | - | - | - | - | - | - | - | - |
| 18 | +HPV 52 | + | + | + | + | + | + | + | + | + | + | + | + | + | + | - | - | + | -* | - | - | - | - | - | - | - | - | - | - | - | - | - | - | - | - | - | - | - | - | - | - |
| 19 | +HPV 53 | + | + | + | + | + | + | + | + | + | + | + | + | + | + | - | + | + | + | + | - | - | - | - | - | - | - | - | - | - | - | - | - | - | - | - | - | - | - | - | - |
| 20 | +HPV 54 | + | + | + | + | + | + | + | + | + | + | + | + | + | + | - | + | + | + | + | + | - | - | - | - | - | - | - | +* | - | - | - | - | - | - | - | - | - | - | - | - |
| 21 | +HPV 56 | + | + | + | + | + | + | + | + | + | + | + | + | + | + | - | + | + | + | + | + | - | - | - | - | - | - | - | +* | - | - | - | - | - | - | - | - | - | - | - | - |
| 22 | +HPV 58 | + | + | + | + | + | + | + | + | + | + | + | + | + | + | - | + | + | + | + | + | + | - | - | - | - | - | - | - | - | - | - | - | - | - | - | - | - | - | - | - |
| 23 | +HPV 59 | + | + | + | + | + | + | + | + | + | + | + | + | + | + | - | + | + | + | + | + | + | + | - | - | - | - | - | +* | - | - | - | - | - | - | - | - | - | - | - | - |
| 24 | +HPV 61 | + | + | + | + | + | + | + | + | + | + | + | + | + | + | - | + | + | + | + | + | + | + | - | - | - | - | - | - | - | - | - | - | - | - | - | - | - | - | - | - |
| 25 | +HPV 66 | + | + | + | + | + | + | + | + | + | + | + | + | + | + | - | + | + | + | + | + | + | + | - | + | - | - | - | - | - | - | - | - | - | - | - | - | - | - | - | - |
| 26 | +HPV 67 | + | + | + | + | + | + | + | + | + | + | + | + | + | + | - | + | + | + | + | + | + | + | - | + | + | - | - | - | +* | - | - | - | - | - | - | - | - | - | - | - |
| 27 | +HPV 69 | + | + | + | + | + | + | + | + | + | + | + | + | + | + | - | + | + | + | + | + | + | + | - | + | + | - | + | - | +* | - | - | - | - | - | - | - | - | - | - | - |
| 28 | +HPV 70 | + | + | + | + | + | + | + | + | + | + | + | + | + | + | - | + | + | + | + | + | + | + | - | + | + | - | + | + | +* | - | - | - | - | - | - | - | - | - | - | - |
| 29 | +HPV 72 | + | + | + | + | + | + | + | + | + | + | + | + | + | + | - | + | + | + | + | + | + | + | - | + | + | - | + | + | - | + | - | - | - | - | - | - | - | - | - | - |
| 30 | +HPV 73 | + | + | + | + | + | + | + | + | + | + | + | + | + | - | + | + | + | + | + | + | + | + | - | + | + | +* | + | + | - | + | + | - | - | - | - | - | - | - | - | - |

\* * False negative or positive results

Figure 5

SET OF PROBES FOR THE DETECTION AND TYPING OF 46 HUMAN PAPILLOMAVIRUS MUCOSAL TYPES

PRIOR APPLICATION INFORMATION

The instant application claims the benefit of U.S. Provisional Patent Application 61/296,245 filed Jan. 19, 2010

FIELD OF THE INVENTION

The present invention relates to reagents and methods for genotyping human papillomaviruses (HPV). In particular, the present invention relates to testing clinical samples for the type of HPV infection using a multiplex assay based on PCR amplification and detection using microspheres.

BACKGROUND OF THE INVENTION

Human papillomaviruses cause ubiquitous infectious of the keratinised epithelia of the skin and of the mucosae. About 120 HPV types have been characterized so far, which differ in prevalence, epidemiology and clinical manifestations (de Villiers et al., 2004). In particular, mucosal types infect the keratinised epithelia of the genital, anal and oro-pharyngeal mucosae (Muñoz et al., 2003; Muñoz and Bosch, 1997; Van Ranst et al, 1992; Chan et al., 1995, D'Souza et al., 2007, Bosh et al., 2008). Mucosal HPVs are most commonly transmitted by sexual contact, and infect sexually active people with a very high prevalence. It is estimated that the lifetime incidence of HPV infection in women is 80% (Bekkers at al., 2004), and the overall prevalence of active infection worldwide varies form 1.4% to 25% (Clifford at al, 2005).

Although the vast majority of infections are benign and self-limiting, a subset of "high risk" HPV types have the potential to cause persistent infection that may progress to malignant transformation and invasive cancer (Muñoz et al., 2003). Cervical cancer is the most common HPV-associated malignancy and it is now clear that HPV is a necessary cause of virtually all cervical cancers (Bosch and Muñoz, 2002; zur Hausen, 2002, Bosch et al., 2002; Muñoz et al., 2003; Walboomers et al., 1999, Smith et al, 2007). HPV associated malignancies are also found in the anal canal (Melbye and Sprogel, 1991; Palefsky et al., 1991), vulva (Buscema et al., 1988), the penis (Gregoire et al., 1995; Iwasawa et al., 1993), oro-pharyngeal mucosae and other head and neck tissues (D'Souza, et al., 2007; Mork et al., 2001; Gillison et al., 2000; Syrjanen, 2005).

Since HPV infection is necessary for the development of virtually all cervical cancers, detection of high risk HPV types is being considered as a screening method for cervical cancer, alongside, or even in substitution of, traditional cytological screening using the Papanicolau methods (pap test), with the promise of improving the sensitivity and cost effectiveness of cervical cancer screening programs (Cuzik et al., 2008; Cuzick et al., 2003; Ronco et al., 2006; Schiffman et al., 2005; Kim et al., 2005; Davies et al., 2006; Mayrand et al., 2006; Cuzik et al., 2006).

Two type-specific HPV vaccines (Gardasil, from Merck-Frosst for types 16, 18, 6 and 11; Cervarix form Glaxo-Smith-Kline for types 16 and 18) have recently been developed and clinical trials have shown that they are extremely effective in preventing both persistent infection with HPV and the dysplastic changes in the cervical epithelium that lead to malignant transformation (Koutsky et al., 2002; Villa et al., 2005; Harper et al., 2004; Harper et al., 2006). However, since vaccines are type-specific it is important to know the distribution of the various HPV types in a population, as well as to have a surveillance system in place to monitor vaccine efficacy and unexpected shifts in the frequency of HPV types not covered by the vaccines.

It is therefore expected that the routine use of type-specific tests for HPV will become more widespread, outside their current use in epidemiological studies for research purposes.

Currently, typing of HPV requires amplification by various PCR methods, followed by detection of specific sequences using either direct sequencing of the PCR products, RFLP methods (many methods have been described in the literature, for example Lungo et al., 1992; Menzo et al., 2008, Nobre et al., 2008; Santiago et al., 2006), Southern blot or dot blot using specific probes (for example Gregoire et al., 1989; Josefsson et al., 1999), reverse line hybridization (Gravitt et al., 1998; Kleter et al., 1999; van der Brule et al., 2002; Melchers et al, 1999), DNA microarray methods (Min et al., 2006; Albrecht et al, 2006; Choi et al., 2003; Huang et al., 2004; Hwang eta la., 2003; Oh et al., 2004; Nuovo et al., 2008), and others (for example Nishiwaki et al., 2008; Dell'Atti, 2007; Gao et al., 2003; Gharizadeh et al., 2007; Han et al., 2006; Lee et al., 2005; Liu et al, 2003; Zhang et al, 2003). In particular, reverse line blot methods have been validated and have been used extensively for epidemiological studies. Two leading commercial genotyping methods, Inno-LiPA (van Hamont, 2006) and Roche linear array (Coutlee et al., 2006), are based on the reverse hybridization technology. The Roche Linear Array genotyping kit as been approved by FDA and it is the leading commercial genotyping method. However, these methods are not suitable for high throughput testing and they rely on a subjective visual assessment of band intensity for determining the results.

The xMAP technology developed by Luminex (Austin, Tex., USA) is based on microspheres that can be produced in 100 different "colours" depending on they ratio of two spectrally distinct fluorophores coupled to the microspheres. The different colours can be recognized by flow cytometers and the different type of microspheres can be enumerated and analyzed for the presence of specific bound ligands. This technology has been the basis for a variety of multiplex assays for serology, genotyping and other analytical applications. A description of the Luminex technology and a list of publications can be found at the Luminex web site.

Each type of microsphere can be coupled with a specific ligand, e.g. with DNA probes specific for each type of HPV in this work, and mixed together to form a multiplex assay. The PCR products derived from HPV samples are labelled with biotin and mixed with the beads carrying the probes, so that HPV DNA will hybridize with the cognate probe. The flow cytometer will then sort the different "coloured" microspheres and determine which type carries the fluorescence due to the HPV DNA. The computer software driving the flow cytometer will indicate which beads are fluorescent, thereby identifying the HPV type(s) present in the sample. The advantages of this method is the low cost per assay, the possibility of automation for a high throughput assay, and the flexibility derived from the possibility of adding or removing types of microspheres depending on the need of the assay or on the discovery of new types. Several microsphere-based multiplex assay for HPV genotyping have been published. The method by Wallace et al. (2005) is a multiplex microsphere assay with probes for 45 mucosal HPV. However, formal validation was performed for only a few types and only 20 types were detected from clinical samples, without independent validation of the genotyping result. The method published by Oh et al. (2007) detects 15 HPV types and it has been validated against a 132 clinical samples. A 56 sample comparison with a DNA microarray genotyping method is also shown. The method, by Schmitt et al. (2006), has been carefully validated with HPV plasmids and clinical samples and covers the 22 most common mucosal HPV types. The method by Jiang et al. (2006) describes specific probes for 26 HPV mucosal types. Validation was performed with synthetic oligonucleotides complementary to the probes and with a limited number of clinical samples. A commercial method developed by Qiagen (Hilden, Germany) is able to type 18 HPV high-risk using a proprietary set of primers, followed by detection using a Luminex system. At least one study comparing this Luminex Qiagen test to a reverse line blot hybridization has been published (Seme et al., 2009).

Herein, we report the design of novel HPV type-specific probes and the development of a microsphere multiplex assay that can detect 46 different mucosal types in a single reaction. In addition the unique probe set, compared to the previous method we introduce 2 innovations: i) the use of longer probes (30 mers) to provide for a greater specificity for variants and closely related types; ii) the production of single stranded DNA products by selective digestion of the PCR products with exonuclease, which produces a greater signal to noise ratio, making a washing step unnecessary.

SUMMARY OF THE INVENTION

We have described a set of 46 DNA probes and a PCR amplification method for the detection of 46 mucosal HPV types using the Luminex xMAP technology. This technology uses a mixture of sortable microsphere coupled to the specific HPV probes, so that all the 46 types can be detected simultaneously in one reaction tube.

Our data shows that all the probes are sensitive and specific for the detection of the 46 HPV types, without cross-hybridization. This conclusion is supported by the use of reference DNA from the 46 types and an extensive validation using direct sequencing as a gold standard for the identification of the HPV types.

Amplified DNAs from at least 32 HPV types can be detected simultaneously and precisely by this Luminex method.

Comparison with a leading commercial HPV typing method, the Roche Linear Array, confirms that the NML Luminex method is suitable for the identification of HPV types in clinical samples containing 3 or less HPV types. However, the PCR amplification method is less efficient in amplifying DNA from samples with multiple infections containing 4 or more HPV types. This is a problem caused by the PCR amplification method and not by the set of probes or the Luminex detection system. The less efficient amplification in multiple infections is a significant problems for HPV types 52, 53, 61, 73 84 and 89 but not for the major oncogenic HPV types, which are most important in epidemiology and clinical practice.

When samples with 4 or more HPV types are excluded, detection by NML Luminex and Roche Linear array are equivalent. Therefore, use of the NML Luminex method on populations with high frequency of multiple infections (such as HIV patients, men who have sex with men or sex workers) will lead to an underestimation of the prevalence with certain types. On the contrary, use of the NML Luminex method on a general population of women, where the prevalence of infections with 4 or more types is negligible, will produce accurate prevalence results for most types.

The NML Luminex HPV genotyping method has the advantage of detecting almost all genital HPV types and of being very sensitive thanks to the nested PCR method. The Luminex xMAP technology allows for a very quick, hands-off reading of the samples and an objective computational interpretation of the results. Because our method has no washing steps or visual reading steps, it is easily amenable to automation.

According to a first aspect of the invention, there is provided a method of detecting and typing a human papillomavirus (HPV) type infection in a sample comprising:
 a) providing a sample suspected of comprising at least one HPV type;
 b) adding to the sample primers suitable for amplifying the L1 region of HPV;
 c) incubating the sample under conditions suitable for DNA amplification;
 d) adding at least one probe having a nucleotide sequence as set forth in any one of SEQ ID NOs: 1-46, said probe binding to only one HPV type under hybridization conditions, each said at least one probe further comprising a unique tag;
 e) incubating said probe and said sample under conditions suitable for hybridization; and
 f) detecting hybridization of at least one said tagged probe.

According to a second aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 1-46.

According to a third aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 1, 2, 4 or 5.

According to a fifth aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID. NOs: 4, 5 and 17.

According to a sixth aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 4, 5, 8, 10, 11, 12, 17, 18, 19, 22, 23, 24, 27 and 29.

According to a seventh aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 6, 4, 5, 7, 8, 10, 11, 12, 17, 18, 19, 20, 22, 23, 24, 27, 28, 29, 30, 31, 34, 37, 40 and 46.

According to an eighth aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 1, 2, 9, 13, 14, 15, 16, 21, 25, 26, 27, 28, 29, 30, 31, 33, 35, 36, 38, 39, 41, 42, 43, 44 and 45.

BRIEF DESCRIPTION OF THE DRAWINGS

FIG. 2—Position of the probes for the 46 HPV types considered in this submission. The alignment of the L1 region comprised between the GP5+/GP6+ primers is shown. The positions of the primers in indicated by the boxes while the probe sequences are in bold and underlined. Shown are probes for HPV 6 (SEQ ID NO: 231), HPV 11 (SEQ ID NO: 232): HPV 13 (SEQ ID NO: 233), HPV 16 (SEQ ID NO: 234), HPV 18 (SEQ ID NO: 235), HPV 26 (SEQ ID NO: 236), HPV 30 (SEQ ID NO: 237), HPV 31 (SEQ ID NO: 238), HPV 32 (SEQ ID NO: 239), HPV 33 (SEQ ID NO: 240), HPV 35 (SEQ ID NO: 241), HPV 39 (SEQ ID NO: 242), HPV 40 (SEQ ID NO: 243), HPV 42 (SEQ ID NO: 244), HPV 43 (SEQ ID NO: 245), HPV 44 (SEQ ID NO: 246), HPV 45 (SEQ ID NO: 247), HPV 51 (SEQ ID NO: 248), HPV 52 (SEQ ID NO: 249), HPV 53 (SEQ ID NO: 250), HPV 54 (SEQ ID NO: 251), HPV 56 (SEQ ID NO: 252), HPV 58 (SEQ ID NO: 253), HPV 59 (SEQ ID NO: 254), HPV 61 (SEQ ID NO: 255), HPV 62 (SEQ ID NO: 256), HPV 66 (SEQ ID NO: 257), HPV 67 (SEQ ID NO: 258), HPV 68 (SEQ ID NO: 259), HPV 69 (SEQ ID NO: 260), HPV 70 (SEQ ID NO: 261), HPV 71 (SEQ ID NO: 262), HPV 72 (SEQ ID NO: 263), HPV 73 (SEQ ID NO: 264), HPV 74 (SEQ ID NO: 265), HPV 81 (SEQ ID NO: 266), HPV 82 (SEQ ID NO: 267), HPV 83 (SEQ ID NO: 268), HPV 84 (SEQ ID NO: 269), HPV 85 (SEQ ID NO: 270), HPV 86 (SEQ ID NO: 271), HPV 87 (SEQ ID NO: 272), HPV 89 (SEQ ID NO: 273), HPV 90 (SEQ ID NO: 274), HPV 91 (SEQ ID NO: 275) and HPV 97 (SEQ ID NO: 276).

FIG. 5—Simultaneous detection of multiple HPV types—Samples containing DNA from increasing numbers of HPV types were prepared as described in the text and then detected by the NML Luminex method as described. The number of types in each sample is indicated in the leftmost column. The second column from the left indicates what additional HPV type was added to the mixture. A "+" sign indicates a positive result (over 50 FU). The asterisks indicate false positive or false negative results.

DESCRIPTION OF THE PREFERRED EMBODIMENTS

Figure 1:
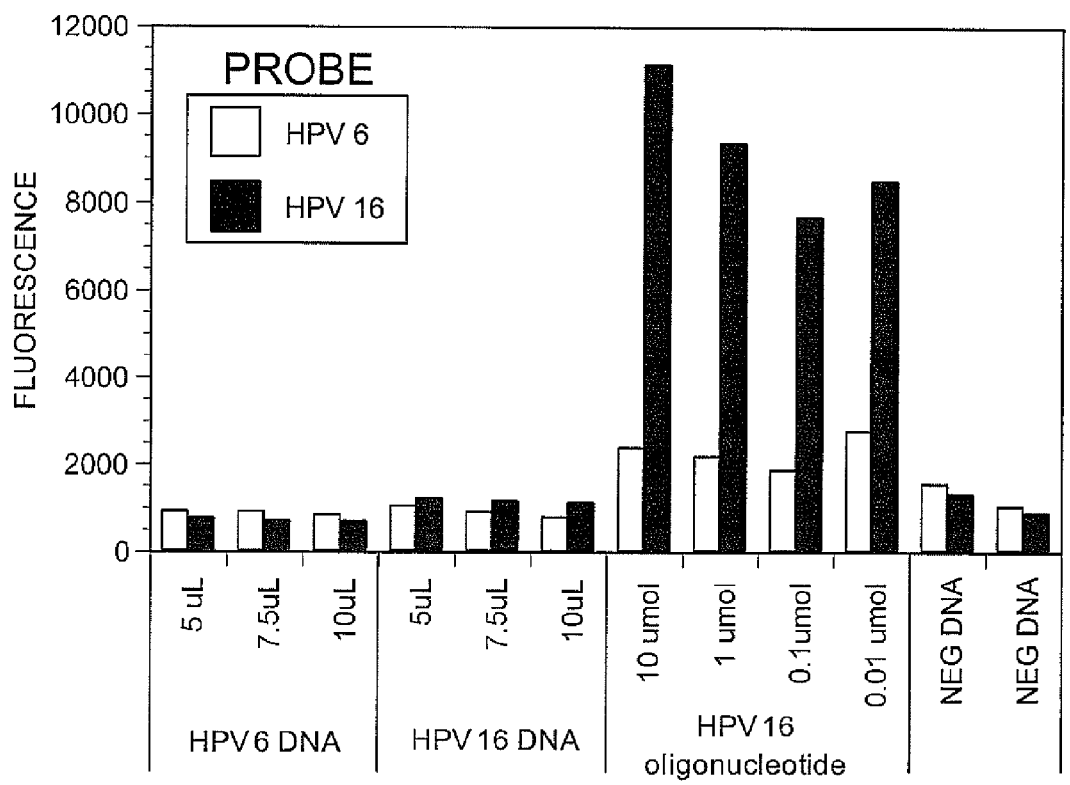
FIG. 1—Preliminary hybridization tests using 20 mer probes for HPV 6 and HPV 16—A mixture of two types of microspheres coupled with 20 mer probes for HPV 6 and 16 (as described in Table 1) were hybridized with the indicated volume of PCR reaction (panel A and B), with a 20 mer oligonucleotide exactly complementary to the HPV 16 probe (panel C), or with an unrelated PCR product (β-globin DNA).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DNA probes comprising SEQ ID NOs: 1 through 46 were generated according to the specific sequences of 46 types of genital HPV, namely type 6 (SEQ ID NO: 1), 11 (SEQ ID NO: 2), 13 (SEQ ID NO: 3), 16 (SEQ ID NO: 4), 18 (SEQ ID NO: 5), 26 (SEQ ID NO: 6), 30 (SEQ ID NO: 7), 31 (SEQ ID NO: 8), 32 (SEQ ID NO: 9), 33 (SEQ ID NO: 10), 35 (SEQ ID NO: 11), 39 (SEQ ID NO: 12), 40 (SEQ ID NO: 13), 42 (SEQ ID NO: 14), 43 (SEQ ID NO: 15), 44 (SEQ ID NO: 16), 45 (SEQ ID NO: 17), 51 (SEQ ID NO: 18), 52 (SEQ ID NO: 19), 53 (SEQ ID NO: 20), 54 (SEQ ID NO: 21), 56 (SEQ ID NO: 22), 58 (SEQ ID NO: 23), 59 (SEQ ID NO: 24), 61 (SEQ ID NO: 25), 62 (SEQ ID NO: 26), 66 (SEQ ID NO: 27), 67 (SEQ ID NO: 28), 68 (SEQ ID NO: 29), 69 (SEQ ID NO: 30), 70 (SEQ ID NO: 31), 71 (SEQ ID NO: 32), 72 (SEQ ID NO: 33), 73 (SEQ ID NO: 34), 74 (SEQ ID NO: 35), 81 (SEQ ID NO: 36), 82 (SEQ ID NO: 37), 83 (SEQ ID NO: 38), 84 (SEQ ID NO: 39), 85 (SEQ ID NO 40), 86 (SEQ ID NO: 41), 87 (SEQ ID NO: 42), 89 (SEQ ID NO: 43), 90 (SEQ ID NO: 44), 91 (SEQ ID NO: 45) and 97 (SEQ ID NO: 46). In order to make each probe sensitive and specific, the probes were tested in a multiplex assay as described below. Probes that in these tests did not hybridize to the intended HPV type or that cross-hybridized to other types were re-designed, sometimes repeatedly, until all probes hybridized to unique HPV type DNA. Accordingly, each respective probe binds specifically to only one specific HPV genome or HPV type. The history of the probe design is shown in Table 2.

For the multiplex assay, each probe was conjugated to one of 46 types of fluorescent microspheres, each with different ratios of red and infrared fluorophores, according to the manufacturers instructions. The micropsheres produced by Luminex Corp. are colour coded with a combination of two fluorescence dyes into 100 different sets that can be recognized and counted by a flow cytometer using a red laser. The flow cytometer can also detect a reporter dye bound to any set of beads using a separate green laser. For this embodiment, 46 sets of beads were selected and each set was coupled to a unique 30mer oligonucleotide probe designed to hybridize sensitively and specifically to one of 46 types of genital HPV DNA, amplified as described below. The 46 sets of beads were mixed to constitute a multiplex reaction that could detect any combination of the 46 types of HPV DNA present in clinical specimens.

The probes were designed to amplify the region comprised between the PCR amplification primers GP5+/GP6+. This region is 141 bp long for HPV 16 (nucleotides 6624 to 6764, GenBank accession no. AF125673), but varies in length slightly depending on the HPV type. GP5+/GP6+ are general primers that amplify the DNA from most HPV types. Published primers sets MY09/MY11 and primer set PGMY are also general primers which amplify most genital HPV types. They are situated outside the GP+/GP6+ region and therefore they can be used for a nested PCR reaction with the GP5+/GP6+ primers, in order to improve the sensitivity and the spectrum of HPV types that can be amplified, especially when multiple types are present in the same sample.

Using these primers, HPV DNA from clinical samples was amplified and then treated with T7 exonuclease to produce a single stranded, biotin labelled DNA complementary to the probes coupled to the microspheres. The single stranded HPV DNA and the tagged microspheres were then co-incubated, so that the HPV DNA could bind to its cognate probe on the microspheres. Streptavidin conjugated to the fluorophore phycoerythrine was then added. Streptavidin binds tightly to biotin conferring phycoerythrine fluorescence to those microsphere that are bound to HPV DNA. The samples were then analyzed by flow cytometry which provided an analysis of the numbers of each type of bound microspheres and their level of phycoerythrine fluorescence. High phycoerythrine fluoresce on specific beads indicates the presence of HPV DNA of specific types.

In addition to the multiplex assay for 46 HPV types, the microspheres can be mixed in different combinations to test separately only for HPV types contained in vaccines (HPV type 6 (SEQ ID NO: 1), 11 (SEQ ID NO: 2), 16 (SEQ ID NO: 4) and 18 (SEQ ID NO: 5)), or to test for the most malignant HPV types (HPV types 16 (SEQ ID NO: 4), 18 (SEQ ID NO: 5) and 45 (SEQ ID NO: 17)), or for the most common HPV types (HPV type 16 (SEQ ID NO: 4), 18 (SEQ ID NO: 5), 31 (SEQ ID NO: 8), 33 (SEQ ID NO: 10), 35 (SEQ ID NO: 11), 39 (SEQ ID NO: 12), 45 (SEQ ID NO: 17), 51 (SEQ ID NO: 18), 52 (SEQ ID NO: 19), 56 (SEQ ID NO: 22), 58 (SEQ ID NO: 23), 59 (SEQ ID NO: 24), 66 (SEQ ID NO: 27) and 68 (SEQ ID NO: 29)), or to test for all oncogenic HPV types (HPV type 26 (SEQ ID NO: 6), 16 (SEQ ID NO: 4), 18 (SEQ ID NO: 5), 30 (SEQ ID NO: 7), 31 (SEQ ID NO: 8), 33 (SEQ ID NO: 10), 0.35 (SEQ ID NO: 11), 39 (SEQ ID NO: 12), 45 (SEQ ID NO: 17), 51 (SEQ ID NO: 18), 52 (SEQ ID NO: 19), 53 (SEQ ID NO: 20), 56 (SEQ ID NO: 22), 58 (SEQ ID NO: 23), 59 (SEQ ID NO: 24), 66 (SEQ ID NO: 27), 67 (SEQ ID NO: 28), 68 (SEQ ID NO: 29), 69 (SEQ ID NO: 30), 70 (SEQ ID NO: 31), 73 (SEQ ID NO: 34), 82 (SEQ ID NO: 37), 85 (SEQ ID NO: 40), and 97 (SEQ ID NO: 46)), or to test only for non-oncogenic (low risk) types (6 (SEQ ID NO: 1), 11 (SEQ ID NO: 2), 32 (SEQ ID NO: 9), 40 (SEQ ID NO: 13), 42 (SEQ ID NO: 14), 43 (SEQ ID NO: 15), 44 (SEQ ID NO: 16), 54 (SEQ ID NO: 21), 61 (SEQ ID NO: 25), 62 (SEQ ID NO: 26), 66 (SEQ ID NO: 27), 67 (SEQ ID NO: 28), 68 (SEQ ID NO: 29), 69 (SEQ ID NO: 30), 70 (SEQ ID NO: 31), 72 (SEQ ID NO: 33), 74 (SEQ ID NO: 35), 81 (SEQ ID NO: 36), 83 (SEQ ID NO: 38), 84 (SEQ ID NO: 39), 86 (SEQ ID NO: 41), 87 (SEQ ID NO: 42), 89 (SEQ ID NO: 43), 90 (SEQ ID NO: 44) and 91 (SEQ ID NO: 45)).

In accordance with a first embodiment of the present invention, there is provided a series of DNA probes that can be used in conjunction with DNA amplification techniques to genotype various strains of HPV.

In a second embodiment of the invention, the series of DNA probes that can be used in a multiplexed format assay to simultaneously detect multiple strains of HPV In a third embodiment of the invention, the DNA probes can be used with other detection systems including Southern or Northern blots, reverse line blot hybridization, DNA microarray or ELISA, or other such systems as will be obvious to those skilled in the art.

According to an aspect of the invention, there is provided a method of detecting and typing a human papillomavirus (HPV) type infection in a sample comprising:

a) providing a sample suspected of comprising at least one HPV type;

b) adding to the sample primers suitable for amplifying the L1 region of HPV;

c) incubating the sample under conditions suitable for DNA amplification;

d) adding at least one probe having a nucleotide sequence as set forth in any one of SEQ ID NOs: 1-46, said probe binding to only one HPV type under hybridization conditions, each said at least one probe further comprising a unique tag;

e) incubating said probe and said sample under conditions suitable for hybridization; and f) detecting hybridization of at least one said tagged probe.

As discussed herein, the sample may contain more than one HPV type and the 'at least one probe' may be a set of probes comprising or consisting of respective probes having nucleotide sequences as set forth in any one of SEQ ID NOs: 1-46 and a unique tag or identification tag which uniquely identifies the respective probe. For example, all probes having a nucleotide sequence as set forth according to SEQ ID NO: 1 will have the same tag as will all probes having a nucleotide sequence as set forth in SEQ ID NO: 2.

As discussed herein, the hybridization conditions are sufficiently stringent that the probe will bind only to the target DNA. For example, the hybridization conditions may be sufficiently stringent for hybridization of two strands to occur only if there is 15, 16, 17, 18, 19, 20 or more consecutive nucleotides having an exact match.

As will be appreciated by one of skill in the art, the probes consisting of nucleotide sequences as set forth in any one of SEQ ID NOs: 1-46 and a unique tag can be used together or in any sub-combination thereof in a multiplex assay to specifically type HPV types in a given sample. Specifically, because each probe has a unique tag associated therewith, hybridization of a respective probe to a DNA molecule within the sample indicates the presence of the corresponding HPV type in that sample. The probe set is unique in that the probes do not cross-hybridize, as discussed below.

In some embodiments, at least one probe may refer to a mixture of probes, each representative probe of said mixture having a nucleotide sequence as set forth in SEQ ID NOs: 1, 2, 4 or 5 or as set forth in SEQ ID NOs: 4, 5 or 17 or as set forth in SEQ ID NOs: 4, 5, 8, 10, 11, 12, 17, 18, 19, 22, 23, 24, 27 or 29 or as set forth in SEQ ID NOs: 6, 4, 5, 7, 8, 10, 11, 12, 17, 18, 19, 20, 22, 23, 24, 27, 28, 29, 30, 31, 34, 37, 40 or 46 or as set forth in SEQ ID NOs: 1, 2, 9, 13, 14, 15, 16, 21, 25, 26, 27, 28, 29, 30, 31, 33, 35, 36, 38, 39, 41, 42, 43, 44 or 45.

The unique tag is a combination of two fluorescent dyes.

The unique tag is a combination of different ratios of red and infra-red fluorophores, as discussed herein.

According to another aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 1-46.

According to another aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 1, 2, 4 or 5. As will be appreciated by one of skill in the art, additional probes having sequences as set forth in any one of SEQ ID NOs: 3 and 6-46 and any combination thereof may be added to the probe set.

According to another aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID. NOs: 4, 5 and 17.

According to another aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 4, 5, 8, 10, 11, 12, 17, 18, 19, 22, 23, 24, 27 and 29.

According to another aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 6, 4, 5, 7, 8, 10, 11, 12, 17, 18, 19, 20, 22, 23, 24, 27, 28, 29, 30, 31, 34, 37, 40 and 46.

According to another aspect of the invention, there is provided a set of probes for detection and typing human papilloma virus (HPV) types, each said probe of said set hybridizing to only one HPV type under hybridizing conditions, each said probe of said set consisting of a unique tag and a nucleotide sequence as set forth in one of SEQ ID NOs: 1, 2, 9, 13, 14, 15, 16, 21, 25, 26, 27, 28, 29, 30, 31, 33, 35, 36, 38, 39, 41, 42, 43, 44 and 45.

EXAMPLES

Oligonucleotides

Oligonucleotides were synthesized at the DNA Core Section of the National Microbiology Laboratory. The probes carried a 5' $C_{12}$ amino linker modification for coupling to the carboxyl group of the Luminex microspheres. The MY09, MY11, GP5+ and the modified GP6+ primer for the PCR amplification of HPV DNA, were purchased from Invitrogen (Burlington ON, Canada).

PCR amplification

HPV DNA from plasmid or clinical specimens was amplified by a nested PCR method using the MY09/MY11 primers for the first step (Manos et al., 1989) and GP5+/GP6+ primers for the second step (Roda Husman et al., 1995). For optimal amplification of clinical samples with multiple HPV types, PGMY primers were used for the first step (Gravitt et al, 2000). The GP6+ primer carried the following modification: i) a 5' biotin label to be used as a ligand for the streptavidin-PE for detection of PCR products (See below); ii) the first 4 nucleotides on the 5' end were linked by phosphorothioate bonds to confer resistance to the action of the bacteriophage T7 gene 6 exonuclease (See below and in the result section). PCR amplification was performed in 1×PCR Buffer (Invitrogen, Cat #10342-020) in the presence of 4 mM $MgCl_2$, 200 μM of dNTP (Invitrogen, Cat#10297-018), 0.2 mM of each primer and 1.25 U of Amplitaq Gold polymerase (Applied Biosystem, Cat #4311816). The first round of nested PCR amplification with the MY09/MY11 primers started with a 5 min initial denaturation step at 94° C., followed by 30 cycles of denaturation at 94° C. for 30 seconds, annealing at 55° C. for 30 seconds and elongation at 72° C. for 60 seconds, followed by a 7 min final extension at 72° C. Amplification with PGMY primers was carried out for 40 cycles (denaturation at 94° C. for 30 sec, annealing 55° C. for 30 sec, elongation 72° C. for 30 sec) in the presence of 6 mM $MgCl_2$, 200 μM dNTPs and 0.6 μM each of the 18 primers comprising the PGMY mixture (Gravitt et al., 2000). One to 5 (typically 2) μL of this reaction were used for the second round of amplification with GP5+/GP6+ primers under the following conditions: 5 min initial denaturation at 94° C., followed by 30 cycles of 94° C. for 30 seconds, 40° C. for 20 seconds and 72° C. for 30 seconds, followed by a 7 min final extension at 72° C. One-step PCR with GP5+/GP6+ primers was conducted under the following conditions: a 5 min initial denaturation at 94° C. followed by 30 cycles of 94° C. for 30 seconds, 40° C. for 20 seconds and 72° C. for 30 seconds followed by a 7 min final extension at 72° C.

Digestion of PCR Products with T7 Exonuclease

After PCR, the GP5+ strand complementary to the biotinylated strand, was removed by digestion with T7 genes exonuclease, a 5'-3' processive exonuclease. The other strand was protected from the action of T7 exonuclease by the 4 phosphorothioate bonds on the 5' (Nikiforov et al, 1994). This digestion produced a single stranded, biotin labelled DNA complementary to the probes coupled to the Luminex beads and it was performed by adding T7 exonuclease (New New England Biolabs, Cat# M0263L) to PCR products at a final concentration of 0.4 U/μl. The reaction was stopped by adding 0.5M EDTA at a final concentration of 12.5 μl of 0.5M EDTA.

Preparation of Microspheres

Microspheres labelled with different ratios of red and infrared fluorophores were purchased from Luminex (Austin, Tex., USA, Cat #L100-CXXX-01) and coupled to HPV type-specific probes carrying a 5' amino modification that reacts with the carboxyl groups on the microspheres following the instruction of the manufacturer with minor modifications. Briefly, the microsphere stock (Luminex) was vortexed vigorously then an aliquot containing $5.0 \times 10^6$ microspheres from each set was placed in a separate 1.5 ml microfuge tube, resuspended in a in a sonicating water bath (Branson) and centrifuged at 14000×g for 2 min. The supernatant was removed and the microshperes were resuspended in 50 μl of 0.1 M 2-N-morpholinoethansulfonic acid (MES) (Sigma Cat #M-2933) at a pH of 4.5. Then 1 μl of a 1 mM solution of the appropriate type of amino substituted oligonucleotide was added to a different set of microspheres and 2.54 of a 10 mg/mL solution of 1-Ethyl-3-3-dimethylaminopropyl carbodiimide HCl (EDC) (Fisher Cat #22980) were added to each tube. The tubes were vortexed and, after an incubation of 30 min at RT in the dark, 2.5 μL of 10 mg/ml EDC were added to each tube and incubated in the dark for 30 minutes. After the second incubation period 1 ml of 0.02% Tween 20 (Sigma Cat # P-9416) was added and the tubes were centrifuged for 2 minutes at 14,000×g. The supernatant was removed and 1 ml of 0.1% SDS (sodium dodecyl sulfate) was added to the microsphere pellet, the tubes were vortexed and then microcentrifuged for 2 minute at 14,000×g. The supernatant was removed and the pellet was resuspended in 100 μl of TE. The microspheres coupled to the probes were stored in the dark at 4° C. for a maximum of 6 months.

Luminex Assay

For the Luminex assay typically 15 microspheres/ul of each set were mixed in a reaction mixture. Exonuclease-digested PCR products were placed in a 96 well PCR microplate (Fisher, Cat # CS006509) in a total volume of 17 ul and sealed with a 96 well sealing cover (Fisher, Cat # CS006555). The microplate was incubated at 95° C. for 10 minutes to denature the DNA and 33 μL of the microsphere mix was added. The samples were incubated at the hybridization temperature of for 10 min and, after addition of 25 μl of a 0.04 mg/ul solution of streptavidine-phycoerythrin (Invitrogen Cat # S-866) in 1× tetramethyl ammonium chloride (TMAC) (Sigma, Cat # T-3411) was added to the samples and incubated for 5 more minutes at 60° C. Samples were analyzed on a Luminex Liquid Chip 200 flow cytometer using the Luminex IS software. The analysis was carried out at 60° C. with a maximum volume of 50 μL of sample and a minimum count of 100 microspheres per type, with a setting of 8,300 and 16,500 for the lower and upper gate, respectively.

Example 1

Design and Selection of Probes

The probes were targeted at the region of the L1 gene comprised between the GP5+/GP6+ primers (Roda Husman et al., 1995). This is a relatively poorly conserved region bracketed by two conserved regions were the GP5+/GP6+ primers bind. The length of this segment varies slightly among different types and, for example, it is 141 bp long in HPV16, corresponding to nt 6624 to 6764 of the sequence published by Flores et al., 1999 (GenBank accession no. AF125673).

Previous literature on the use of Luminex Xmap technology for detecting DNA sequence typically reported the use of 20 nt long probes. We therefore designed first 20 nt long probes, using the ArrayDesigner computer software (Premier BioSoft International) (Table 1), but preliminary experiments with probes and DNA from HPV type 6 and 16 showed that these probes were not sensitive for the detection of HPV DNA under our conditions. As shown in FIG. 1, DNA amplified from HPV 6 and HPV 16 clones failed to hybridize to the microsphere carrying the cognate 20 mer probe (Pane A and B). A biotylinated oliginucleotide exactly complementary to the HPV 16 probe did produce a considerable fluorescence of the HPV 16 microsphere but it also non-specifically increased the fluorescence of the HPV 6 microsphere (panel C).

Therefore, the probes were then re-designed as 30mers by adding 10 nt to the left or the right of the original probe. Longer probes also provide greater specificity and a better chance of discriminating among closely related HPV types or variants, for example HPV16 and HPV 31. This initial set or 30mers contained numerous unsuitable probes, either because they were cross-reactive (poor specificity) or because they were not binding efficiently to the intended target (poor sensitivity), or both. Unsuitable probes were redesigned typically by shifting their position 10 nucleotides to the right or to the left along the variable region of the GP5+/GP6+ fragment. This process was repeated until all probes were both specific and sensitive for the intended target. Attempts to predict the efficiency and specificity of the probes or to weed out probes with hairpins or other cross-reactive sequences proved ineffectual, because often probes behaved in an unexpected manner.

Figure 2:
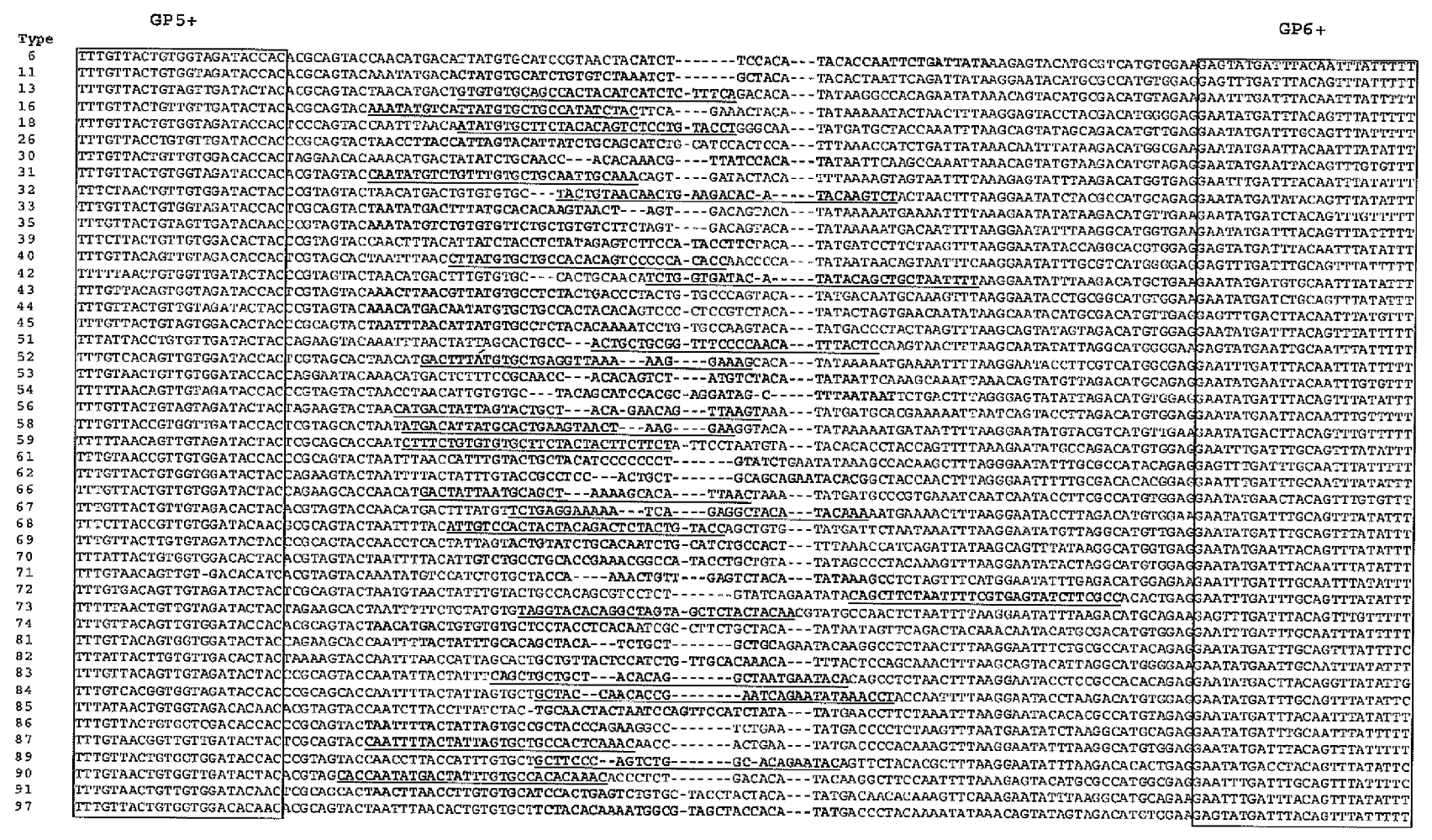

The history of the development of the probes is shown of Table 2, while the final sets of probes used for this method is shown on Table 3. FIG. 2 shows the location of the probes on the aligned sequences of the 46 HPV types covered by this method.

Example 2

Effect of Exonuclease

Figure 3:
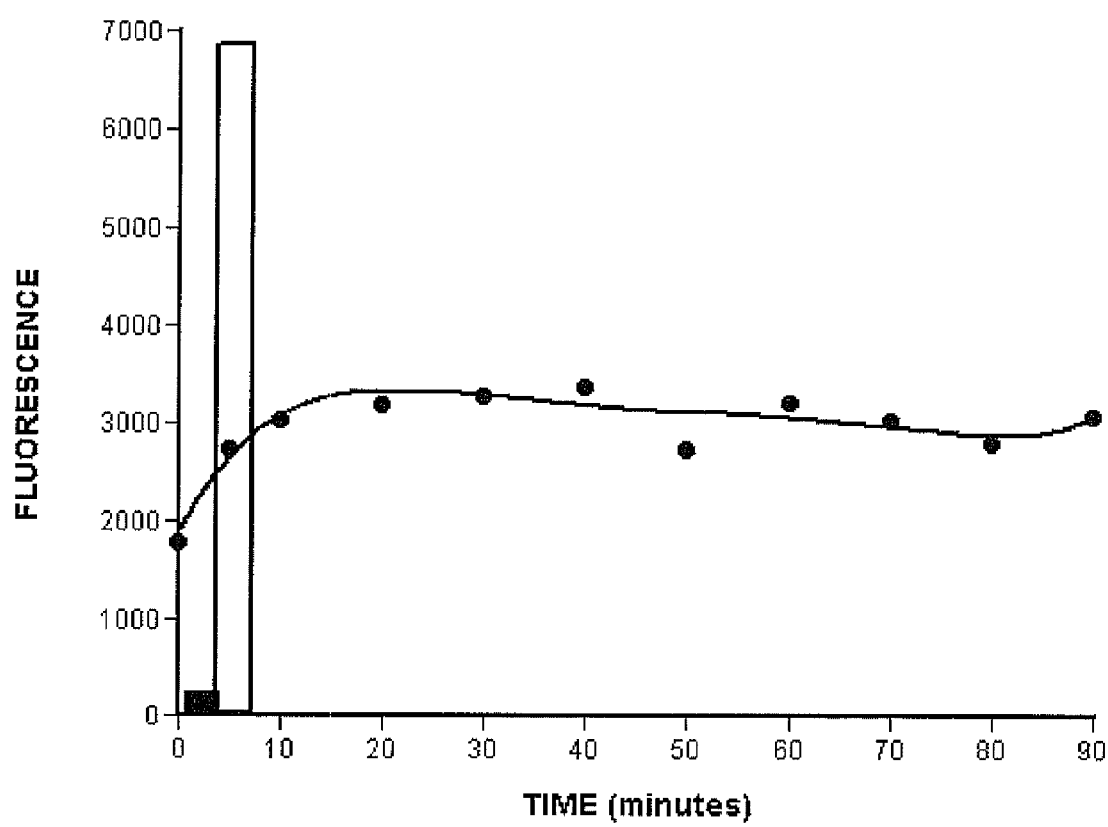
FIG. 3—Effect of T7 exonuclease digestion of nested PCR products on hybridization to Luminex beads. HPV 16 DNA was amplified by MY09/My11 and GP5+/GP6+ nested PCR, as described above, and the products were digested with T7 exonuclease for the indicated times. After digestion, the PCR products were hybridized to Luminex beads carrying the HPV 16 probe and detected as described above. The GP6+ primer contained a 5' biotin moiety, for detection by the Luminex technology, and phosphorothioate bonds in the first 4 nucleotides on the 5', to protect this strand from the action of the T7 exonuclease. The black bar and the white bar represent the fluorescence signals of a negative sample and of a sample containing a biotinylated oligonucleotide complementary to the HPV 16 probe.

Simple denaturation of the double-stranded PCR products followed by hybridization to the probes on the microspheres produced a fluorescence signal that was much lower compared to the signal produced by hybridizing the microspheres to biotin-labelled single-stranded oligonucleotides (FIG. 3). We suspected that rehybridization of the long strands of the PCR products might have been thermodynamically more favourable than the hybridization of the GP6+ strand to the short (30 nt) probe physically constrained on the microsphere. We therefore decided to remove the non-labelled strand of the PCR product using bacteriophage T7 gene 6 exonuclease, according to the method described earlier (Nikiforov et al., 1994). T7 exonulease is a 5'→3' processive enzyme that rapidly degrades one of the strand on a duplex DNA molecule (Kerr and Sadowski, 1972). In order to protect the GP6+ strand, carrying the biotin label, and selectively digest only GP5+ strand, the first 4 nucleotides at the 5' end of the molecule were modified to include phosphorothioate bonds between the deoxyribose moieties, instead of the usual phosphodiester bonds. This chemical modification is known to inhibit the action of T7 exonuclease, that can no longer digest the DNA molecule starting from such modified end (Nikiforov et al., 1994).

Optimal digestion conditions were determined by incubating 40 units of T7 exonuclease with 100 ul of PCR product for various times, and then measuring the fluorescence on the Luminex system. These experiments, like the one showed in FIG. 3 determined that an incubation of 40 minutes is optimum for the sensitivity of the test and increased the fluorescence signal by about 2 fold.

Example 3

Typing of HPV

Specificity and sensitivity for each type was determined by adding PCR product from a known source of HPV, clones carrying the whole HPV genome, when available, or clones of the MY region of the genome amplified by PCR form clinical samples or synthesized using published genomic sequences (see Material and methods for a complete list). All clones were confirmed by direct sequencing and comparison with published HPV sequences.

Using the PCR amplification method, exonuclease digestion and microsphere hybridization described above, amplified HPV DNA from each type was hybridized to a mixture of the 46 types of microspheres carrying the 46 specific HPV probes. After hybridization, the microsphere mixture was analyzed by the Luminex LiquidChip 200 flow cytometer. Four negative controls, containing only host cell DNA, were run alongside the samples. The average background fluorescence of each bead in the controls was subtracted from the fluorescence of each bead of the samples. This type of background correction is necessary because different bead types may have different background fluorescence. This corrections avoids the need for a bead washing step, used in other Luminex procedures (Wallace et al., 2005; Oh et al., 2007; Schmitt et al., 2006; Jiang et al., 2006; Seme et al., 2009). A fluorescence signal greater than 100 FU after correction was chosen as threshold for positivity.

Figure 4:
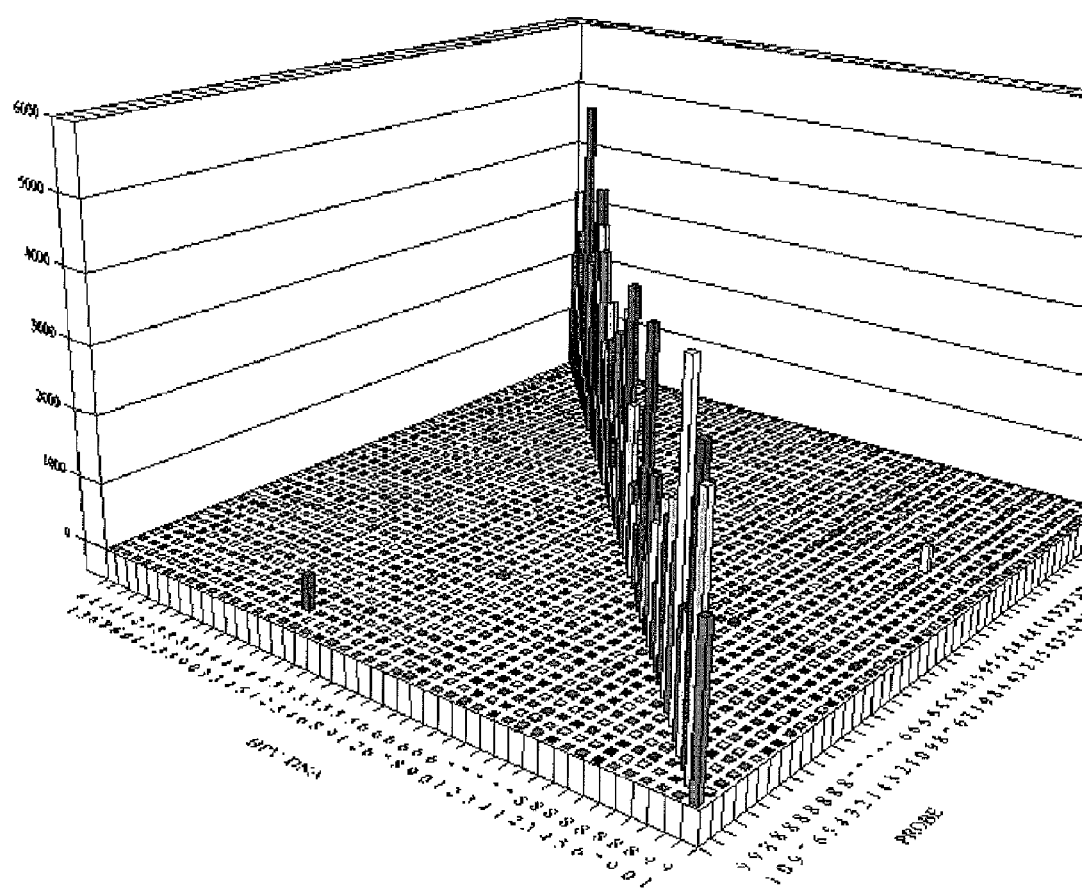
FIG. 4—Graphic representation of the data of Table 4—The probes are on the right axis and the HPV DNAs on the left axis. The vertical axis represents the fluorescence read for each microsphere carrying a specific HPV probe. The bars on the diagonal represent the hybridization of HPV DNA type with the intended cognate probe.

The complete results of are shown in Table 4, where each column represents the fluorescence associated with the microsphere carrying the probe for the indicated HPV type in the presence of the HPV DNA of the types indicated on the leftmost column. FIG. 4 shows the same results in graphic format. It can be seen that all the 46 probes strongly hybridize with the corresponding HPV DNA, but not with HPV DNA of different types. It should be noted that in the particular experiment shown in Table 4 and FIG. 4, the microsphere for HPV 89 also shows fluorescence above the 100 FU threshold level in the presence of HPV 44 DNA (513 FU), the microsphere for HPV 72 in the presence HPV 81 DNA (118 FU) and the microsphere for HPV 44 in the presence of HPV 86 DNA (391 FU). This should be interpreted as random fluctuations, rather than systematic cross-reactivity, because the abnormal fluorescence reading was not reproducible in other experiments. This corresponds to a false positive rate of 3/1980 measurements or 0.15%. To avoid false positives, clinical samples are tested in duplicate and the measurement is repeated if the duplicates give discordant results.

We then tested the ability of the Luminex method to detect infections with multiple types in the same sample, by amplifying DNAs from different HPV types separately and then mixing them together in a single Luminex detection reaction. The amount of DNA per type was kept constant, to simulate the situation of clinical samples, in which a mixture of different DNA is amplified to the maximum capacity of the PCR reaction, regardless of the number of types present. The results are presented in FIG. 5, that shows that at least 30 different types can be detected simultaneously with minimal cross hybridization. Some false negatives and false positives are however present. The false negatives are probably due to the fact that the fluorescence for each HPV type is low when many types are present and therefore some microsphere may fall under the 50 FU that was established as positivity threshold. False positive for HPV 72 are due to fluctuation in the background fluorescence of this microsphere.

Example 4

Validation Using Clinical Samples—Direct Sequencing

Validation against clinical samples was performed by comparing the results of the NML Luminex genotyping method with direct sequencing of the amplified products. Because direct sequencing identifies any HPV type without misclassification, this is a further test of the specificity of the probes of the NML Luminex assay.

Seven hundred seventy five samples were amplified by nested PCR as described above and the products were typed with the NML Luminex method. The same samples were amplified separately by nested PCR and run on an agarose gel to determine the presence of HPV DNA. Positive samples were sent for sequencing at the NML DNA Core facility, using GP5+ and GP6+ primers to sequence both strands of the amplified products. The assembled sequenced was compared against GenBank sequences using BLAST (Altschul et al., 1990). Type identification required a nucleotide identity greater that 90% on a fragment of at least 60 nucleotide in length.

The results presented in Table 5, show that the two methods were 97.7% concordant for the detection of HPV, regardless of type. The sensitivity and specificity of the NML Luminex method vs direct sequencing, taken as a gold standard, were 98.8% (97.1-99.6, 95% CI) and 96.4% (96.4-93.8, 95% CI), respectively.

When positive identification of HPV type is taken into consideration, the direct sequencing method could not determine the sequence of 34 positive samples, 32 of which were typed by the NML Luminex method. There was no agreement on the HPV type detected for 13 out of 429 samples positive with both methods (3.3%). The NML Luminex method detected a total of 793 HPV types, vs 577 for direct sequencing. This discrepancy is due to the fact that direct sequencing cannot detect multiple HPV types present in the same sample.

A breakdown of HPV types detected by the two methods is presented in Table 6.

From the validation against the direct sequencing method, it is impossible to establish if the extra types detected by the NML Luminex assay are due to better sensitivity for multiple infections or to poor specificity.

Example 5

Validation Using Clinical Samples—Comparison to Roche Linear Assay

Therefore we compared the performance of the NML Luminex assay using the Roche LinearArray HPV genotyping method as the gold standard. The Linear Array kit can detect 37 different genotypes and its amplification system, based on the PGMY primers, is particularly efficient in amplifying multiple types. Linear Array is FDA approved and it is one of the standard methods used in the literature on HPV epidemiology.

For this comparison we used a set of 880 samples that were tested for HPV at the National Microbiology Laboratory in parallel by the Roche Linear Array kit, according to the instruction of the manufacturer, and by the NML Luminex genotyping method.

The Linear Array probe for HPV 52 cross-reacts with HPV type 33, 35 and 58. Therefore all Linear Array HPV 52 results were confirmed by real time PCR specific for HPV 52 as previously described (Coutlee et al., 2007). Linear Array contains a probe designated HPV 55, but according to the latest classification of HPVs (de Villier et al, 2004) the type 55 is considered a variant of HPV 44 and HPV 55 has been removed. Therefore in this work we used the HPV 44 designation. Roche Linear Array probes IS39 and CP6108 recognize types more recently designated as HPV 82 and HPV 89 respectively. The more recent designation was used in this work.

Table 7 shows a comparison of the NML Luminex with Roche linear array for the detection of positive samples for any HPV type. Discordant results are 7% overall and 5.2% of discordant samples tested positive with the NML Luminex but not with the linear array. This is due to the greater sensitivity of the nested PCR used for the NML Luminex method and to the detection of HPV types not present on the linear array set of probes.

Table 8 shows the comparison of the NML Luminex method with the Roche Linear array for the detection of all HPV types and multiple infections. The Roche Linear array detected considerably more types of HPV (1111 vs. 917), due to the better performance in samples with high numbers of multiple infections. This reduced performance for multiple infections is not due is not a problem with the Luminex detection system, which can detect at least 32 different types simultaneously, as shown above (FIG. 5), but it is a shortcoming of the PCR amplification step, which is less efficient when a mixture of different types is present. Table 9 shows the comparison results for the individual types. Apart from the types not detected by the Roche Linear Array (HPV 13, 32, 74, 85, 86, 87, 90 and 91) the detection of HPV types 52, 53, 61, 73 84 and 89 was statistically significantly more sensitive ($X^2$ test) in the Roche linear Array, while the detection of HPV type 67 was more sensitive in the NML Luminex.

Table 10 shows the results after exclusion of samples with multiple infections with 4 or more types, as determined by the Roche linear array. This Table shows a much better concordance between NML Luminex and Roche Linear Array with respect of total number of types detected (535 vs 534, respectively) and type breakdown. In addition to the types not detected by the Roche Linear Array, only type 52 (better detection for Linear Array) and type 67 (better detection for NM Luminex) are now significantly different.

While the preferred embodiments of the invention have been described above, it will be recognized and understood that various modifications may be made therein, and the appended claims are intended to cover all such modifications which may fall within the spirit and scope of the invention.

REFERENCES

Albrecht, V., A. Chevallier, V. Magnone, P. Barbry, F. Vandenbos, A. Bongain, J. C. Lefebvre, and V. Giordanengo.

2006. Easy and fast detection and genotyping of high-risk human papillomavirus by dedicated DNA microarrays. J. Virol. Methods. 137:236-244.

Altschul, S. F., W. Gish, W. Miller, E. W. Myers, and D. J. Lipman. 1990. Basic local alignment search tool. J. Mol. Biol. 215:403-410.

Bekkers, R. L., L. F. Massuger, J. Bulten, and W. J. Melchers. 2004. Epidemiological and clinical aspects of human papillomavirus detection in the prevention of cervical cancer. Rev. Med. Virol. 14:95-105.

Bosch, F. X. and N. Muñoz. 2002. The viral etiology of cervical cancer. Virus Res. 89:183-190.

Bosch, F. X., A. Lorincz, N. Muñoz, C. J. Meijer, and K. V. Shah. 2002. The causal relation between human papillomavirus and cervical cancer. J. Clin. Pathol. 55:244-265.

Bosch, F. X., A. N. Burchell, M. Schiffman, A. R. Giuliano, S. de Sanjose, L. Bruni, G. Tortolero-Luna, S. K. Kjaer, and N. Munoz. 2008. Epidemiology and natural history of human papillomavirus infections and type-specific implications in cervical neoplasia. Vaccine 26 Suppl 10:K1-16.

Buscema, J., Z. Naghashfar, E. Sawada, R. Daniel, J. D. Woodruff, and K. Shah. 1988. The predominance of human papillomavirus type 16 in vulvar neoplasia. Obstet. Gynecol. 71:601-606.

Chan, S. Y., H. Delius, A. L. Halpern, and H. U. Bernard. 1995. Analysis of genomic sequences of 95 papillomavirus types: uniting typing, phylogeny, and taxonomy. J. Virol. 69:3074-3083.

Choi, B. S., O. Kim, M. S. Park, K. S. Kim, J. K. Jeong, and J. S. Lee. 2003. Genital human papillomavirus genotyping by HPV oligonucleotide microarray in Korean commercial sex workers. J. Med. Virol. 71:440-445.

Clifford, G. M., S. Gallus, R. Herrero, N. Munoz, P. J. Snijders, S. Vaccarella, P. T. Anh, C. Ferreccio, N. T. Hieu, E. Matos, M. Molano, R. Rajkumar, G. Ronco, S. de Sanjose, H. R. Shin, S. Sukvirach, J. O. Thomas, S. Tunsakul, C. J. Meijer, and S. Franceschi. 2005. Worldwide distribution of human papillomavirus types in cytologically normal women in the International Agency for Research on Cancer HPV prevalence surveys: a pooled analysis. Lancet 366:991-998.

Coutlee, F., D. Rouleau, G. Ghattas, C. Hankins, S. Vezina, P. Cote, J. Macleod, A. de Pokomandy, D. Money, S. Walmsley, H. Voyer, P. Brassard, and E. Franco. 2007. Confirmatory real-time PCR assay for human papillomavirus (HPV) type 52 infection in anogenital specimens screened for HPV infection with the linear array HPV genotyping test. J. Clin. Microbial. 45:3821-3823.

Coutlee, F., D. Rouleau, P. Petignat, G. Ghattas, J. R. Kornegay, P. Schlag, S. Boyle, C. Hankins, S. Vezina, P. Cote, J. Macleod, H. Voyer, P. Forest, S. Walmsley, and E. Franco. 2006. Enhanced detection and typing of human papillomavirus (HPV) DNA in anogenital samples with PGMY primers and the Linear array HPV genotyping test. J. Clin. Microbial. 44:1998-2006.

Cuzick, J., A. Szarewski, H. Cubie, G. Hulman, H. Kitchener, D. Luesley, E. McGoogan, U. Menon, G. Terry, R. Edwards, C. Brooks, M. Desai, C. Gie, L. Ho, I. Jacobs, C. Pickles, and P. Sasieni. 2003. Management of women who test positive for high-risk types of human papillomavirus: the HART study. Lancet 362:1871-1876.

Cuzick, J., M. Arbyn, R. Sankaranarayanan, V. Tsu, G. Ronco, M. H. Mayrand, J. Diliner, and C. J. Meijer. 2008. Overview of human papillomavirus-based and other novel options for cervical cancer screening in developed and developing countries. Vaccine 26 Suppl 10:K29-K41.

Cuzick, J., M. H. Mayrand, G. Ronco, P. Snijders, and J. Wardle. 2006. Chapter 10: New dimensions in cervical cancer screening. Vaccine 24 Suppl 3:S3-90-S3/97.

Davies, P., M. Arbyn, J. Diliner, H. C. Kitchener, C. J. Meijer, G. Ronco, and M. Hakama. 2006. A report on the current status of European research on the use of human papillomavirus testing for primary cervical cancer screening. Int. J. Cancer 118:791-796.

de Villiers, E. M., C. Fauquet, T. R. Broker, H. U. Bernard, and H. zur Hausen. 2004. Classification of papillomaviruses. Virology 324:17-27.

Dell'Atti, D., M. Zavaglia, S. Tombelli, G. Bertacca, A. O. Cavazzana, G. Bevilacqua, M. Minunni, and M. Mascini. 2007. Development of combined DNA-based piezoelectric biosensors for the simultaneous detection and genotyping of high risk Human Papilloma Virus strains. Clin. Chim. Acta. 383:140-146.

D'Souza, G., A. R. Kreimer, R. Viscidi, M. Pawlita, C. Fakhry, W. M. Koch, W. H. Westra, and M. L. Gillison. 2007. Case-control study of human papillomavirus and oropharyngeal cancer. N. Engl. J. Med. 356:1944-1956.

Flores, E. R., B. L. Allen-Hoffmann, D. Lee, C. A. Sattler, and P. F. Lambert. 1999. Establishment of the human papillomavirus type 16 (HPV-16) life cycle in an immortalized human foreskin keratinocyte cell line. Virology 262:344-354.

Gao, Y. E., J. Zhang, J. Wu, Z. C. Chen, and X. J. Yan. 2003. Detection and genotyping of human papillomavirus DNA in cervical cancer tissues with fluorescence polarization. Sheng Wu Hua Xue. Yu Sheng Wu Wu Li Xue. Bao. (Shanghai). 35:1029-1034.

Gharizadeh, B., M. Oggionni, B. Zheng, E. Akom, N. Pourmand, A. Ahmadian, K. L. Wallin, and P. Nyren. 2005. Type-specific multiple sequencing primers: a novel strategy for reliable and rapid genotyping of human papillomaviruses by pyrosequencing technology. J. Mol. Diagn. 7:198-205.

Gillison, M. L., W. M. Koch, R. B. Capone, M. Spafford, W. H. Westra, L. Wu, M. L. Zahurak, R. W. Daniel, M. Viglione, D. E. Symer, K. V. Shah, and D. Sidransky. 2000. Evidence for a causal association between human papillomavirus and a subset of head and neck cancers. J. Natl. Cancer Inst. 92:709-720.

Gravitt, P. E., C. L. Peyton, R. J. Apple, and C. M. Wheeler. 1998. Genotyping of 27 human papillomavirus types by using L1 consensus PCR products by a single-hybridization, reverse line blot detection method. J. Clin. Microbiol. 36:3020-3027.

Gravitt, P. E., C. L. Peyton, T. Q. Alessi, C. M. Wheeler, F. Coutlee, A. Hildesheim, M. H. Schiffman, D. R. Scott, and R. J. Apple. 2000. Improved amplification of genital human papillomaviruses. J. Clin. Microbiol. 38:357-361.

Gregoire, L., A. L. Cubilla, V. E. Reuter, G. P. Haas, and W. D. Lancaster. 1995. Preferential association of human papillomavirus with high-grade histologic variants of penile-invasive squamous cell carcinoma. J. Natl. Cancer Inst. 87:1705-1709.

Gregoire, L., M. Arella, J. Campione-Piccardo, and W. D. Lancaster. 1989. Amplification of human papillomavirus DNA sequences by using conserved primers. J. Clin. Microbiol. 27:2660-2665.

Han, J., D. C. Swan, S. J. Smith, S. H. Lum, S. E. Sefers, E. R. Unger, and Y. W. Tang. 2006. Simultaneous amplification and identification of 25 human papillomavirus types with Templex technology. J. Clin. Microbiol. 44:4157-4162.

Harper, D. M., E. L. Franco, C. M. Wheeler, A. B. Moscicki, B. Romanowski, C. M. Roteli-Martins, D. Jenkins, A.

Schuind, S. A. Costa Clemens, and G. Dubin. 2006. Sustained efficacy up to 4.5 years of a bivalent L1 virus-like particle vaccine against human papillomavirus types 16 and 18: follow-up from a randomised control trial. Lancet 367:1247-1255.

Harper, D. M., E. L. Franco, C. Wheeler, D. G. Ferris, D. Jenkins, A. Schuind, T. Zahaf, B. Innis, P. Naud, N. S. De Carvalho, C. M. Roteli-Martins, J. Teixeira, M. M. Blatter, A. P. Korn, W. Quint, and G. Dubin. 2004. Efficacy of a bivalent L1 virus-like particle vaccine in prevention of infection with human papillomavirus types 16 and 18 in young women: a randomised controlled trial. Lancet 364: 1757-1765.

Huang, H. J., S. L. Huang, C. Y. Lin, R. W. Lin, F. Y. Chao, M. Y. Chen, T. C. Chang, S. Hsuch, K. H. Hsu, and C. H. Lai. 2004. Human papillomavirus genotyping by a polymerase chain reaction-based genechip method in cervical carcinoma treated with neoadjuvant chemotherapy plus radical surgery. Int. J. Gynecol. Cancer. 14:639-649.

Hwang, T. S., J. K. Jeong, M. Park, H. S. Han, H. K. Choi, and T. S. Park. 2003. Detection and typing of HPV genotypes in various cervical lesions by HPV oligonucleotide microarray. Gynecol. Oncol. 90:51-56.

Iwasawa, A., Y. Kumamoto, and K. Fujinaga. 1993. Detection of human papillomavirus deoxyribonucleic acid in penile carcinoma by polymerase chain reaction and in situ hybridization. J. Urol. 149:59-63.

Jiang, H. L., H. H. Zhu, L. F. Zhou, F. Chen, and Z. Chen. 2006. Genotyping of human papillomavirus in cervical lesions by L1 consensus PCR and the Luminex xMAP system. J. Med. Microbiol. 55:715-720.

Josefsson A, Magnusson P, and Gyllensten U. 1999. Human papillomavirus detection by PCR and typing by dot-blot., p. 171-193. In Peeling R W and Sparling P. F (eds.), Sexually Transmitted Diseases. methods and Protocols. Humana Press, Totowa, N.J.

Kerr, C. and P. D. Sadowski. 1972. Gene 6 exonuclease of bacteriophage T7. II. Mechanism of the reaction. J. Biol. Chem. 247:311-318.

Kim, J. J., T. C. Wright, and S. J. Goldie. 2005. Cost-effectiveness of human papillomavirus DNA testing in the United Kingdom, The Netherlands, France, and Italy. J. Natl. Cancer Inst. 97:888-895.

Kleter, B., L. J. van Doom, J. ter Schegget, L. Schrauwen, K. van Krimpen, M. Burger, B. ter Harmsel, and W. Quint. 1998. Novel short-fragment PCR assay for highly sensitive broad-spectrum detection of anogenital human papillomaviruses. Am. J. Pathol. 153:1731-1739, Koutsky, L. A., K. A. Ault, C. M. Wheeler, D. R. Brown, E. Barr, F. B. Alvarez, L. M. Chiacchierini, and K. U. Jansen. 2002. A controlled trial of a human papillomavirus type 16 vaccine. N. Engl. J. Med. 347:1645-1651.

Lee, G. Y., S. M. Kim, S. Y. Rim, H. S. Choi, C. S. Park, and J. H. Nam. 2005. Human papillomavirus (HPV) genotyping by HPV DNA chip in cervical cancer and precancerous lesions. In J. Gynecol. Cancer. 15:81-87.

Liu, C. H., W. L. Ma, R. Shi, Y. F. Peng, Q. Ouyang, and W. L. Zheng. 2003. Application of Agilent 2100 Bioanalyzer in detection of human papilloma virus. Di Yi. Jun. Yi. Da. Xue. Xue. Bao. 23:213-215.

Lungu, O., T. C. Wright, Jr., and S. Silverstein. 1992. Typing of human papillomaviruses by polymerase chain reaction amplification with L1 consensus primers and RFLP analysis. Mol. Cell. Probes 6:145-162.

Manos M M, Ting Y, Wright D K, Lewis A J, Broker T R, and Wolinsky S M. 1989. USe of PCR amplification for the detection of genital HPV. Cancer Cells 7:209-214.

Mayrand, M. H., E. Duarte-Franco, I. Rodrigues, S. D. Walter, J. Hanley, A. Ferenczy, S. Ratnam, F. Coutlee, and E. L. Franco. 2007. Human papillomavirus DNA versus Papanicolaou screening tests for cervical cancer. N. Engl. J. Med. 357:1579-1588.

Melbye, M., C. Rabkin, M. Frisch, and R. J. Biggar. 1994. Changing patterns of anal cancer incidence in the United States, 1940-1989. Am. J. Epidemiol. 139:772-780.

Melchers, W. J., J. M. Bakkers, J. Wang, P. C. de Wilde, H. Boonstra, W. G. Quint, and A. G. Hanselaar. 1999. Short fragment polymerase chain reaction reverse hybridization line probe assay to detect and genotype a broad spectrum of human papillomavirus types. Clinical evaluation and follow-up. Am. J. Pathol. 155:1473-1478.

Menzo, S., A. Ciavattini, P. Bagnarelli, K. Marinelli, S. Sisti, and M. Clementi. 2008. Molecular epidemiology and pathogenic potential of underdiagnosed human papillomavirus types. BMC. Microbiol. 8:112.

Min, W., M. Wen-Li, Z. Bao, L. Ling, S. Zhao-Hui, and Z. Wen-Ling. 2006. Oligonucleotide microarray with RD-PCR labeling technique for detection and typing of human papillomavirus. Curr. Microbiol. 52:204-209.

Mork, J., A. K. Lie, E. Glattre, G. Hallmans, E. Jellum, P. Koskela, B. Moller, E. Pukkala, J. T. Schiller, L. Youngman, M. Lehtinen, and J. Dillner. 2001. Human papillomavirus infection as a risk factor for squamous-cell carcinoma of the head and neck. N. Engl. J. Med. 344:1125-1131.

Munoz, N. and F. X. Bosch. 1997. Cervical cancer and human papillomavirus: epidemiological evidence and perspectives for prevention. Salud Publica Mex. 39:274-282.

Munoz, N., F. X. Bosch, S. de Sanjose, R. Herrero, X. Castelisague, K. V. Shah, P. J. Snijders, and C. J. Meijer. 2003. Epidemiologic classification of human papillomavirus types associated with cervical cancer. N. Engl. J. Med. 348:518-527.

Nikiforov, T. T., R. B. Rendle, M. L. Kotewicz, and Y. H. Rogers. 1994. The use of phosphorothioate primers and exonuclease hydrolysis for the preparation of single-stranded PCR products and their detection by solid-phase hybridization. PCR Methods Appl. 3:286-291.

Nishiwaki, M., T. Yamamoto, S. Tone, T. Mural, T. Ohkawara, T. Matsunami, M. Koizumi, Y. Takagi, J. Yamaguchi, N. Kondo, J. Nishihira, T. Horikawa, and T. Yoshiki. 2008. Genotyping of human papillomaviruses by a novel one-step typing method with multiplex PCR and clinical applications. J. Clin. Microbial. 46:1161-1168.

Nobre, R. J., L. P. de Almeida, and T. C. Martins. 2008. Complete genotyping of mucosal human papillomavirus using a restriction fragment length polymorphism analysis and an original typing algorithm. J. Clin. Virol. 42:13-21.

Nuovo, G. J., D. Bartholomew, W. W. Jung, I. K. Han, T. Um, D. F. Grabarz, D. J. Lee, and R. T. McCabe. 2008. Correlation of Pap smear, cervical biopsy, and clinical follow-up with an HPV typing microarray system. Diagn. Mol. Pathol. 17:107-111.

Oh, T. J., C. J. Kim, S. K. Woo, T. S. Kim, D. J. Jeong, M. S. Kim, S. Lee, H. S. Cho, and S. An. 2004. Development and clinical evaluation of a highly sensitive DNA microarray for detection and genotyping of human papillomaviruses. J. Clin. Microbiol. 42 :3272-3280.

Palefsky, J. M. 1991. Human papillomavirus-associated anogenital neoplasia and other solid tumors in human immunodeficiency virus-infected individuals. Curr. Opin. Oncol. 3:881-885.

Roda Husman, A. M., J. M. Walboomers, A. J. van den Brule, C. J. Meijer, and P. J. Snijders. 1995. The use of general primers GP5 and GP6 elongated at their 3' ends with adjacent highly conserved sequences improves human papillomavirus detection by PCR. J. Gen. Virol. 76:1057-1062

Ronco, G., P. Giorgi-Rossi, F. Carozzi, P. P. Dalla, A. Del Mistro, L. De Marco, M. De Lillo, C. Naldoni, P. Pierotti, R. Rizzolo, N. Segnan, P. Schincaglia, M. Zorzi, M. Confortini, and J. Cuzick. 2006. Human papillomavirus testing and liquid-based cytology in primary screening of women younger than 35 years: results at recruitment for a randomised controlled trial. Lancet Oncol. 7:547-555.

Santiago, E., L. Camacho, M. L. Junquera, and F. Vazquez. 2006. Full HPV typing by a single restriction enzyme. J. Clin. Virol. 37:38-46.

Seme, K., S. Z. Lepej, M. M. Lunar, J. Iscic-Bes, A. Planinic, B. J. Kocjan, A. Vince, and M. Poljak. 2009. Digene HPV Genotyping RH Test RUO: comparative evaluation with INNO-LiPA HPV Genotyping Extra Test for detection of 18 high-risk and probable high-risk human papillomavirus genotypes. J. Clin. Virol. 46:176-179.

Smith, J. S., L. Lindsay, B. Hoots, J. Keys, S. Franceschi, R. Winer, and G. M. Clifford. 2007. Human papillomavirus type distribution in invasive cervical cancer and high-grade cervical lesions: a meta-analysis update. Int. J. Cancer 121:621-632.

Syrjanen, S. 2005. Human papillomavirus (HPV) in head and neck cancer. J. Clin. Viral. 32 Suppl 1:S59-S66.

van den Brule, A. J., R. Pal, N. Fransen-Daalmeijer, L. M. Schouls, C. J. Meijer, and P. J. Snijders. 2002. GP5+/6+ PCR followed by reverse line blot analysis enables rapid and high-throughput identification of human papillomavirus genotypes. J. Clin. Microbial. 40:779-787.

van Hamont, D., M. A. van Ham, J. M. Bakkers, L. F. Massuger, and W. J. Melchers. 2006. Evaluation of the SPF10-INNO LiPA human papillomavirus (HPV) genotyping test and the roche linear array HPV genotyping test. J. Clin. Microbial. 44:3122-3129.

Van Ranst, M., J. B. Kaplan, and R. D. Burk. 1992. Phylogenetic classification of human papillomaviruses: correlation with clinical manifestations. J. Gen. Virol. 73 :2653-2660.

Villa, L. L., R. L. Costa, C. A. Petta, R. P. Andrade, K. A. Ault, A. R. Giuliano, C. M. Wheeler, L. A. Koutsky, C. Malm, M. Lehtinen, F. E. Skjeldestad, S. E. Olsson, M. Steinwall, D. R. Brown, R. J. Kurman, B. M. Ronnett, M. H. Stoler, A. Ferenczy, D. M. Harper, G. M. Tamms, J. Yu, L. Lupinacci, R. Railkar, F. J. Taddeo, K. U. Jansen, M. T. Esser, H. L. Sings, A. J. Saah, and E. Barr. 2005. Prophylactic quadrivalent human papillomavirus (types 6, 11, 16, and 18) L1 virus-like particle vaccine in young women: a randomised double-blind placebo-controlled multicentre phase II efficacy trial. Lancet Oncol. 6:271-278.

Walboomers, J. M., M. V. Jacobs, M. M. Manos, F. X. Bosch, J. A. Kummer, K. V. Shah, P. J. Snijders, J. Peto, C. J. Meijer, and N. Muñoz. 1999. Human papillomavirus is a necessary cause of invasive cervical cancer worldwide. J. Pathol. 189:12-19.

Zhang, J., X. Yan, J. Sun, Z. Chen, Y. Gao, Y. Bai, and Z. Liu. 2003. A high throughout assay for human papillomavirus genotypes with fluorescence polarization. Chin Med. J. (Engl.). 116:1137-1140.

zur Hausen, H. 2002. Papillomaviruses and cancer: from basic studies to clinical application. Nat. Rev. Cancer 2:342-350.

TABLE 1

Sequences

| Sequence Definition | Probe Sequence | SEQ ID NO: |
|---|---|---|
| HPV 6 | ACCACACGCAGTACCAACAT | 47 |
| HPV 6 | CATGCGTCATGTGGAAGAGT | 48 |
| HPV11 | ATGCGCCATGTGGAGGAGTT | 49 |
| HPV11 | TGGTAGATACCACACGCAGT | 50 |
| HPV13 | TGACTGTGTGTGCAGCCACT | 51 |
| HPV13 | GTTGATACTACACGCAGTAC | 52 |
| HPV16 | ACCTACGACATGGGGAGGAA | 53 |
| HPV16 | ATGTCATTATGTGCTGCCAT | 54 |
| HPV18 | CAGTCTCCTGTACCTGGGCA | 55 |
| HPV18 | AGATACCACTCCCAGTACCA | 56 |
| HPV26 | CCTGTGTTGATACCACCCGC | 57 |
| HPV26 | CAGCATCTGCATCCACTCCA | 58 |
| HPV30 | TGGACACCACTAGGAACACA | 59 |
| HPV30 | ATCTGCAACCACACAAACGT | 60 |
| HPV31 | TGTCTGTTTGTGCTGCAATT | 61 |
| HPV31 | AGATACCACACGTAGTACCA | 62 |
| HPV32 | ATCTACGCCATGCAGAGGAA | 63 |
| HPV32 | ACTGTTGTGGATACTACCCG | 64 |
| HPV33 | TGGTAGATACCACACGCAGT | 65 |
| HPV33 | GCACACAAGTAACTAGTGAC | 66 |
| HPV34 | CCACAAGTACAACTGCACCA | 67 |
| HPV34 | ACCTCAGACATGCAGAAGAG | 68 |
| HPV35 | TGTCTGTGTGTTCTGCTGTG | 69 |
| HPV35 | AGGCATGGTGAAGAATATGA | 70 |
| HPV39 | ACTGTTGTGGACACTACCCG | 71 |
| HPV39 | TACCAGGCACGTGGAGGAGT | 72 |
| HPV40 | ATGTGCTGCCACACAGTCCC | 73 |
| HPV40 | TTTGCGTCATGGGGAGGAGT | 74 |
| HPV42 | GCCACTGCAACATCTGGTGA | 75 |
| HPV42 | ACTGTGGTTGATACTACCCG | 76 |
| HPV44 | GTGCTGCCACTACACAGTCC | 77 |
| HPV44 | CATGCGACATGTTGAGGAGT | 78 |
| HPV45 | GTGGACACTACCCGCAGTAC | 79 |
| HPV45 | GTGCCAAGTACATATGACCC | 80 |
| HPV47 | TTACTCTCAGGCAGGGGACA | 81 |
| HPV47 | GTCACAGTTGTAGACAACAC | 82 |
| HPV51 | GCACTGCCACTGCTGCGGTT | 83 |

TABLE 1-continued

Sequences

| Sequence Definition | Probe Sequence | SEQ ID NO: |
|---|---|---|
| HPV51 | AGGCATGGGAAGAGTATGA | 84 |
| HPV52 | ACCTTCGTCATGGCGAGGAA | 85 |
| HPV52 | TGGATACCACTCGTAGCACT | 86 |
| HPV53 | ACTCTTTCCGCAACCACACA | 87 |
| HPV53 | TGTTGTGGATACCACCAGGA | 88 |
| HPV54 | GCTACAGCATCCACGCAGGA | 89 |
| HPV54 | CAGTTGTAGATACCACCCGT | 90 |
| HPV56 | ACCTTAGACATGTGGAGGAA | 91 |
| HPV56 | CTGCTACAGAACAGTTAAGT | 92 |
| HPV58 | GGTTGATACCACTCGTAGCA | 93 |
| HPV58 | TGCACTGAAGTAACTAAGGA | 94 |
| HPV59 | ACTACTCGCAGCACCAATCT | 95 |
| HPV59 | ATGCCAGACATGTGGAGGAA | 96 |
| HPV61 | CCGTTGTGGATACCACCCGC | 97 |
| HPV61 | TTGCGCCATACAGAGGAGTT | 98 |
| HPV62 | TGTACCGCCTCCACTGCTGC | 99 |
| HPV62 | TTTGCGACACACGGAGGAAT | 100 |
| HPV66 | ACACGCCATGTAGAGGAA | 101 |
| HPV66 | ACCAGAAGCACCAACATGAC | 102 |
| HPVG7 | ACACGTAGTACCAACATGAC | 103 |
| HPV67 | ACCTTAGACATGTGGAAGAA | 104 |
| HPV68 | TTGTGGATACAACGCGCAGT | 105 |
| HPV68 | CAGACTCTACTGTACCAGCT | 106 |
| HPV69 | ACCCGCAGTACCAACCTCAC | 107 |
| HPVG9 | GCACAATCTGCATCTGCCAC | 108 |
| HPV70 | TCTGCCTGCACCGAAACGGC | 109 |
| HPV70 | ACTGTGGTGGACACTACACG | 110 |
| HPV71 | ATGTCCATCTGTGCTACCAA | 111 |
| HPV71 | ACAGTTGTGACACATCACGT | 112 |
| HPV72 | ACTGCCACAGCGTCCTCTGT | 113 |
| HPV72 | ATCTTCGCCACACTGAGGAA | 114 |
| HPV73 | GGTACACAGGCTAGTAGCTC | 115 |
| HPV73 | CTACAACGTATGCCAACTCT | 116 |
| HPV74 | ACCTCACAATCGCCTTCTGC | 117 |
| HPV74 | TGGATACCACACGCAGTACT | 118 |
| HPV82 | GCACTGCTGTTACTCCATCT | 119 |
| HPV82 | AGCAGTACATTAGGCATGGG | 120 |
| HPV82 | GCACTGCTGCTACTCCATCA | 121 |
| HPV82 | GCACAGACATTCACTCCAAC | 122 |
| HPV83 | GCTGCTGCTACACAGGCTAA | 123 |
| HPV83 | ACCTCCGCCACACAGAGGAA | 124 |
| HPV84 | AGATACCACCCGCAGCACCA | 125 |
| HPV84 | AGTGCTGCTACCAACACCGA | 126 |
| HPV85 | ACACACGCCATGTAGAGGAA | 127 |
| HPV85 | ACTGTGGTAGACACAACACG | 128 |
| HPV85 | AGTGCCGCTACCCAGAAGGC | 129 |
| HPV86 | TCGACACCACCCGCAGTACT | 130 |
| HPV87 | TGCTGCCACTCAAACAACCA | 131 |
| HPV87 | CGGTTGTTGATACTACTCGC | 132 |
| HPV89 | GTGCTGCTTCCCAGTCTGGC | 133 |
| HPV89 | ACCACCCGTAGTACCAACCT | 134 |
| HPV91 | TGTGGATACAACTCGCAGCA | 135 |
| HPV91 | GCATCCACTGAGTCTGTGCT | 136 |

TABLE 2

History of Probe Development

| HPV TYPE | OLIGO SEQUENCE 5' TO 3' | DNA SOURCE | BEAD # | COMMENTS | SEQ ID NO: |
|---|---|---|---|---|---|
| 6 | ACTACACGCAGTACCAACATGACATTATGT | PLASMID | 50 | low hybridization | 137 |
|  | CGTAACTACATCTTCCACATACACCAATTC | PLASMID | 50 | no hybridization | 138 |
|  | CAACATGACATTATGTGCATCCGTAACTAC | PLASMID | 50 | no hybridization | 139 |
|  | CATGACATTATGTGCATCCGTAACTACATCTTC | PLASMID | 50 | no hybridization | 140 |
|  | CATCTTCCACATACACCAATTCTGATTATA | PLASMID | 50 | ok | 1 |
|  | TCCGTAACTACATCTTCCACATACACCAAT | PLASMID | 50 | no hybridization | 141 |
| 11 | ACTATGTGCATCTGTGTCTAAATCTGCTAC | PLASMID | 13 | good | 2 |

TABLE 2-continued

History of Probe Development

| HPV TYPE | OLIGO SEQUENCE 5' TO 3' | DNA SOURCE | BEAD # | COMMENTS | SEQ ID NO: |
|---|---|---|---|---|---|
| 13 | AGCCACTACATCATCTCTTTCAGACACATA | PLASMID | 34 | no hybridization | 142 |
|  | TAACATGACTGTGTGTGCAGCCACTACATC | PLASMID | 34 | no hybridization | 143 |
|  | GTGTGTGCAGCCACTACATCATCTCTTTCA | PLASMID | 34 | no hybridization | 3 |
|  | GTGTGTGCAGCCACTACATCATCTCTTTCA | PLASMID | 34 | good | 3 |
| 16 | GCCATATCTACTTCAGAAACTACATATAAA | PLASMID | 98 | no hybridization | 144 |
|  | AAATATGTCATTATGTGCTGCCATATCTAC | PLASMID | 98 | no hybridization | 4 |
|  | ATGTCATTATGTGCTGCCATATCTACTTCA | PLASMID | 98 | cross hybridization with 62 | 145 |
|  | GTCATTATGTGCTGCCATATCTACTTCAGA | PLASMID | 98 | cross hybridization | 146 |
|  | GCCATATCTACTTCAGAAACTACATATAAA | PLASMID | 98 | no hybridization | 147 |
| 18 | ATATGTGCTTCTACACAGTCTCCTGTACCT | PLASMID | 15 | good | 5 |
|  | AACAATATGTGCTTCTACACAGTCTCCTGT | PLASMID | 15 | cross hybridization | 148 |
|  | TCCTGTACCTGGGCAATATGATGCTACCAA | PLASMID | 15 | cross hybridization | 149 |
|  | TATGTGCTTCTACACAGTCTCCTGTACCTG | PLASMID | 15 | no hybridization | 150 |
|  | TATGTGCTTCTACACAGTCTCCTGTACCTG | PLASMID | 15 | no hybridization | 150 |
| 26 | CCTTACCATTAGTACATTATCTGCAGCATC | PLASMID | 5 | good | 6 |
|  | AACCTTACCATTAGTACATTATCTGCAGCA | PLASMID | 5 | no hybridization | 151 |
|  | ACATTATCTGCAGCATCTGCATCCACTCCA | PLASMID | 5 | good | 152 |
| 30 | ATCTGCAACCACACAAACGTTATCCACATA | PLASMID | 53 | good | 7 |
|  | CCACACAAACGTTATCCACATATAATTCAA | PLASMID | 40 | no hybridization | 153 |
|  | GACTATATCTGCAACCACACAAACGTTATC | PLASMID | 40 | no hybridization | 154 |
|  | ATCTGCAACCACACAAACGTTATCCACATA | PLASMID | 40 | no hybridization | 155 |
| 31 | AAGTAGTAATTTTAAAGAGTATTTAAGACA | PLASMID | 55 | no hybridization | 156 |
|  | ATGTCTGTTTGTGCTGCAATTGCAAACAGT | PLASMID | 55 | no hybridization | 157 |
|  | CAATATGTCTGTTTGTGCTGCAATTGCAAA | PLASMID | 55 | low hybridization | 8 |
|  | CAATATGTCTGTTTGTGCTGCAATTGCAAA | PLASMID | 25 | no hybridization | 8 |
|  | CAATATGTCTGTTTGTGCTGCAATTGCAAA | PLASMID | 25 | no hybridization | 8 |
|  | AACAGTGATACTACATTTAAAAGTAGTAAT | PLASMID | 25 | no hybridization | 158 |
|  | TCTGTTTGTGCTGCAATTGCAAACAGTGAT | PLASMID | 25 | no hybridization | 159 |
|  | GCAATTGCAAACAGTGATACTACATTTAAA | PLASMID | 55 | no hybridization | 160 |
| 32 | ACTGTAACAACTGAAGACACATACAAGTCT | Test Sample 4330 | 36 | good | 9 |
| 7 | CACCAACACCATATGACAATAGTAAGTTTA | Test Sample 3228 | 33 | take out not mucosal | 161 |
| 33 | TAGTGACAGTACATATAAAAATGAAAATTT | PLASMID | 58 | cross hybridization | 162 |
|  | TAATATGACTTTATGCACACAAGTAACTAG | PLASMID | 30 | ok | 10 |
|  | GCACACAAGTAACTAGTGACAGTACATATA | PLASMID | 58 | no hybridization | 163 |
|  | GTGACAGTACATATAAAAATGAAAATTTTA | PLASMID | 30 | ok | 164 |
| 34 | TAGGTACACAATCCACAAGTACAACTGCAC | PLASMID | 37 | no dna sample | 165 |
| 35 | TGTCTGTGTGTTCTGCTGTGTCTTCTAGTG | Test Sample 4498 | 30 | no hybridization | 166 |
|  | GTGTCTTCTAGTGACAGTACATATAAAAAT | Test Sample 4498 | 30 | no hybridization | 167 |
|  | AACCCGTAGTACAAATATGTCTGTGTGTTC | Test Sample 4498 | 77 | no hybridization | 168 |
|  | AAATATGTCTGTGTGTTCTGCTGTGTCTTC | Test Sample 4498 | 77 | good | 11 |
|  | TCTGCTGTGTCTTCTAGTGACAGTACAATA | Test Sample 4498 | 77 | no hybridization | 169 |
| 39 | CTTTACATTATCTACCTCTATAGAGTCTTC | Test Sample 4317 | 25 | low hybridization | 170 |
|  | AGAGTCTTCCATACCTTCTACATATGATCC | Test Sample 4317 | 25 | low hybridization | 171 |
|  | CCGTAGTACCAACTTTACATTATCTACCTC | PLASMID | 76 | cross hybridization | 172 |
|  | CAACTTTACATTATCTACCTCTATAGAGTC | PLASMID | 76 | no hybridization | 173 |
|  | ATCTACCTCTATAGAGTCTTCCATACCTTC | PLASMID | 76 | good | 12 |
|  | CTACCTCTATAGAGTCTTCCATACCTTTCT | Test Sample 4317 | 76 | dna sample no good | 174 |
| 40 | GTCCCCCACACCAACCCCATATAATAACAG | TEST SAMPLE 3343 | 38 | cross hybridization | 175 |
|  | CTTATGTGCTGCCACACAGTCCCCCACACC | TEST SAMPLE 3343 | 38 | ok | 13 |
|  | ACCCCATATAATAACAGTAATTTCAAGGAA | TEST SAMPLE 3343 | 38 | cross hybridization | 176 |
|  | ACAGTCCCCCACACCAACCCCATATAATAA | TEST SAMPLE 3343 | 38 | cross hybridization | 177 |
| 42 | TCTGGTGATACATATACAGCTGCTAATTTT | test sample | 42 | multiple infection | 14 |
|  | ACATCTGGTGATACATATACAGCTGCTAAT | none | 42 | cross hybridization | 178 |
|  | CACTGCAACATCTGGTGATACATATACAGC | Test Sample 3398 | 42 | dna sample not good | 179 |
| 43 | AAACTTAACGTTATGTGCCTCTACTGACCC | none | 64 | waiting | 15 |
|  | TGACCCTACTGTGCCCAGTACATATGACAA | none | 64 | cross hybridization | 180 |
|  | TGCAAAGTTTAAGGAATACCTGCGGCA | none | 64 | cross hybridization | 181 |
| 44 | GCCACTACACAGTCCCCTCCGTCTACATAT | PLASMID | 3 | no hybridization | 182 |
|  | GACAATATGTGCTGCCACTACACAGTCCCC | PLASMID | 10 | ok | 183 |
|  | AAACATGACAATATGTGCTGCCACTACACA | PLASMID | 10 | good | 16 |
|  | AATATGTGCTGCCACTACACAGTCCCCTCC | PLASMID | 10 | cross hybridization | 184 |

TABLE 2-continued

History of Probe Development

| HPV TYPE | OLIGO SEQUENCE 5' TO 3' | DNA SOURCE | BEAD # | COMMENTS | SEQ ID NO: |
|---|---|---|---|---|---|
| 45 | TAATTTAACATTATGTGCCTCTACACAAAA | PLASMID | 18 | good | 17 |
|  | TAACATTATGTGCCTCTACACAAAATCCTG | Plasmid | 18 | no hybridization | 185 |
|  | CTCTACACAAAATCCTGTGCCAAGTACATA | PLASMID | 18 | low hybridization | 186 |
| 51 | TTAACTATTAGCACTGCCACTGCTGCGGTT | Test Sample 98066 | 28 | no hybridization | 187 |
|  | GCCACTGCTGCGGTTTCCCCACATTTACTC | Test Sample 98066 | 28 | no hybridization | 18 |
|  | TTTAACTATTAGCACTGCCACTGCTGCGGT | Test Sample 98066 | 28 | no hybridization | 188 |
|  | TAGCACTGCCACTGCTGCGGTTTCCCCAAC | Test Sample 98066 | 28 | no hybridization | 189 |
| 52 | CACAGTTGTGGATACCACTCGTAGCACTAA | PLASMID | 23 | no hybridization | 190 |
|  | AAAAGGAAAGCACATATAAAAATGAAAATT | PLASMID | 23 | no hybridization | 191 |
|  | CACTGCTAGCACTAACATGACTTTATGTGC | PLASMID | 8 | no hybridization | 192 |
|  | CATGACTTTATGTGCTGAGGTTAAAAAGGA | PLASMID | 8 | no hybridization | 193 |
|  | AGCACATATAAAAATGAAAATTTTAAGGAA | PLASMID | 8 | no hybridization | 194 |
|  | GACTTTATGTGCTGAGGTTAAAAAGGAAAG | PLASMID | 8 | no hybridization | 19 |
|  | AAAAGGAAAGCACATATAAAAATGAAAATT | PLASMID | 8 | no hybridization | 195 |
|  | GAGGTTAAAAAGGAAAGCACATATAAAAAT | PLASMID | 8 | cross hybridization | 196 |
| 53 | GATCTCTTTCCGCAACCACACAGTCTATGT | PLASMID | 44 | no hybridization | 197 |
| 53 | CTCTTTCCGCAACCACACAGTCTATGTCTA | PLASMID | 44 | no hybridization | 198 |
| 53 | CTACATATAATTCAAAGCAAATTAAACAGT | PLASMID | 44 | no hybridization | 199 |
| 53 | CGCAACCACACAGTCTATGTCTACATATAA | PLASMID | 44 | good | 20 |
| 54 | ACAGCATCCACGCAGGATAGCTTTAATAAT | Plasmid | 65 | good | 21 |
| 56 | AGTTAAGTAAATATGATGCACGAAAAATTA | PLASMID | 35 | cross hybridization | 200 |
| 56 | GTACTGCTACAGAACAGTTAAGTAAATATG | PLASMID | 35 | no hybridization | 201 |
| 56 | TAGAAGTACTAACATGACTATTAGTACTGC | PLASMID | 35 | no hybridization | 202 |
| 56 | CATGACTATTAGTACTGCTACCAGAACAGT | PLASMID | 35 | good | 22 |
| 58 | TGCACTGAAGTAACTAAGGAAGGTACATAT | Test Sample 98028 | 43 | no hybridization | 203 |
| 58 | CACTAATATGACATTATGCACTGAAGTAAC | Test Sample 98028 | 43 | some cross hybridization | 204 |
| 58 | ATGACATTATGcAcTGAAGTAAcTAAGGAA | Test Sample 98028 | 43 | good | 23 |
| 58 | ACTAAGGAAGGTACATATAAAAATGATAAT | Test Sample 98028 | 43 | no hybridization | 205 |
| 59 | ctttctgtgtgtgcttctactacttcttct | PLASMID | 60 | good | 24 |
| 59 | ACTACTCGCAGCACCAATCTTTCTGTGTGT | PLASMID | 60 | significant amounts of cross hybridization | 206 |
| 61 | CATTTGTACTGCTACATCCCCCCCTGTATC | PLASMID | 46 | good | 25 |
| 61 | TAATTTAACCATTTGTACTGCTACATCCCC | Plasmid | 46 | no hybridization | 207 |
| 61 | AACCATTTGTACTGCTACATCCCCCCCTGT | PLASMID | 46 | low hybridization | 208 |
| 62 | ACCGCCTCCACTGCTGCAGCAGAATACACG | Test sample N34 | 66 | good | 26 |
| 66 | TGAAATCAATCAATACCTTCGCCATGTGGA | Test Sample 99081 | 40 | no hybridization | 209 |
| 66 | GACTATTAATGCAGCTAAAAGCACATTAAC | Test sample 4491 | 75 | good | 27 |
| 66 | AGCTAAAAGCACATTAACTAAATATGATGC | Test sample 4491 | 75 | no hybridization | 210 |
| 66 | TAATGCAGCTAAAAGCACATTAACTAATAT | Test sample 4491 | 75 | cross hybridization | 211 |
| 66 | TTAACTAAATATGATGCCCGTGAAATCAAT | SAMPLE 4491 | 75 | cross hybridization | 212 |
| 66 | TAATGCAGCTAAAAGCACATTAACTACATA | Test sample 4491 | 20 | cross hybridization | 213 |
| 67 | AAAAATCAGAGGCTACATACAAAAATGAAA | PLASMID | 200 | waiting | 214 |
| 67 | TCTGAGGAAAATCAGAGGCTACATACAAA | PLASMID | 200 | good | 28 |
| 68 | ATTGTCCACTACTACAGACTCTACTGTACC | none | 45 | no dna sample | 29 |
| 69 | ACTGTATCTGCACAATCTGCATCTGCCACT | none | 72 | no dna sample | 30 |
| 70 | GTCTGCCTGCACCGAAACGGCCATACCTGC | Test Sample 4190 | 47 | good | 31 |
| 71 | ACCAAAACTGTTGAGTCTACATATAAAGCC | none | 73 | no dna sample | 32 |
| 72 | CAGCTTCTAATTTTCGTGAGTATCTTCGCC | PLASMID | 51 | good | 33 |
| 72 | CACAGCGTCCTCTGTATCAGAATATTACAG | PLASMID | 51 | good | 215 |
| 73 | TAGGTACACAGGCTAGTAGCTCTACTACAA | PLASMID | 52 | good | 34 |
| 74 | TAACATGACTGTGTGTGCTCCTACCTCACA | Plasmid | 54 | good | 35 |
| 74 | CTCACAATCGCCTTCTGCTACATATAATAG | PLASMID | 54 | no hybridization | 216 |
| 81 | CACAGCTACATCTGCTGCAGAATACAA | PLASMID | 56 | cross hybridization | 217 |
| 81 | TACTATTTGCACAGCTACATCTGCTGCTGC | Plasmid | 56 | good | 36 |
| 81 | ATCTGCTGCTGCAGAATACAAGGCCTCTAA | PLASMID | 56 | low hybridization | 218 |
| 82 | GCTGTTACTCCATCTGTTGCACAAACATTT | PLASMID | 61 | good | 37 |
| 83 | CAGCTGCTGCTACACAGGCTAATGAATACA | test sample 22038 | 74 | no dna sample | 38 |
| 84 | GCTACCAACACCGAATCAGAATATAAACCT | test sample 21A | 17 | no dna sample | 39 |
| 85 | TGCAACTACTAATCCAGTTCCATCTATATA | none | 19 | no dna sample | 40 |
| 86 | CCCCTCTAAGTTTAATGAATATCTAAG | none | 20 | cross hybridization | 219 |
| 86 | TAATTTTACTATTAGTGCCGCTACCCAGAA | none | 20 | no dna sample | 41 |
| 86 | TCTGAATATGACCCCTCTAAGTTTAATGA | none | 20 | cross hybridization | 220 |
| 86 | CGCTACCCAGAAGGCCTCTGAATATGACCC | none | 20 | cross hybridization | 221 |
| 87 | TGCCACTCAAACAACCACTGAATATGACCC | none | 62 | cross hybridization | 222 |
| 87 | CAATTTTACTATTAGTGCTGCCACTCAAAC | none | 62 | no dna sample | 42 |
| 87 | CACAAAGTTTAAGGAATATTTAAGGCA | none | 62 | cross hybridization | 223 |
| 87 | AACAACCACTGAATATGACCCCACAAAGTT | none | 62 | cross hybridization | 224 |
| 89 | GCTTCCCAGTCTGGCACAGAATAC | none | 23 | good | 43 |
| 89 | CCGTAGTACCAACCTTACCATTTGTGCTGC | none | 23 | cross hybridization | 225 |
| 89 | CATTTGTGCTGCTTCCCAGTCTGGCACAGA | none | 23 | cross hybridization | 226 |
| 90 | CACCAATATGACTATTTGTGCCACACAAAC | test sample 4015 | 83 | no dna sample | 44 |

TABLE 2-continued

History of Probe Development

| HPV TYPE | OLIGO SEQUENCE 5' TO 3' | DNA SOURCE | BEAD # | COMMENTS | SEQ ID NO: |
|---|---|---|---|---|---|
| 90 | CACACAAACACCCTCTGACACATACAAGGC | test sample 4015 | 83 | cross hybridization | 227 |
| 91 | TAACTTAACCTTGTGTGCATCCACTGAGTC | test sample 50211 | 63 | hybridizes with 89 | 45 |
| 91 | CTACCTACTACATATGACAACACAAAGTTC | find new dna | 63 | no hybridization | 228 |
| 91 | ATCCACTGAGTCTGTGCTACCTACTACATA | find new dna | 63 | no hybridization | 229 |
| 97 | TTTAACACTGTGTGCTTCTACACAAAATGG | PLASMID | | Fair | 230 |
| 97 | TCTACACAAAATGGCGTAGCTACCACATAT | PLASMID | | good | 46 |

TABLE 3

Probe Sequences
Final list of probes for the detection of 46 HPV types with the Luminex Microsphere technology.

| SEQ ID NO: | HPV TYPE | OLIGO SEQUENCE 5' TO 3' |
|---|---|---|
| 1 | 6 | CATCTTCCACATACACCAATTCTGATTATA |
| 2 | 11 | ACTATGTGCATCTGTGTCTAAATCTGCTAC |
| 3 | 13 | GTGTGTGCAGCCACTACATCATCTCTTTCA |
| 4 | 16 | AAATATGTCATTATGTGCTGCCATATCTAC |
| 5 | 18 | ATATGTGCTTCTACACAGTCTCCTGTACCT |
| 6 | 26 | CCTTACCATTAGTACATTATCTGCAGCATC |
| 7 | 30 | ATCTGCAACCACACAAACGTTATCCACATA |
| 8 | 31 | CAATATGTCTGTTTGTGCTGCAATTGCAAA |
| 9 | 32 | ACTGTAACAACTGAAGACACATACAAGTCT |
| 10 | 33 | TAATATGACTTTATGCACACAAGTAACTAG |
| 11 | 35 | AAATATGTCTGTGTGTTCTGCTGTGTCTTC |
| 12 | 39 | ATCTACCTCTATAGAGTCTTCCATACCTTC |
| 13 | 40 | CTTATGTGCTGCCACACAGTCCCCCACACC |
| 14 | 42 | TCTGGTGATACATATACAGCTGCTAATTTT |
| 15 | 43 | AAACTTAACGTTATGTGCCTCTACTGACCC |
| 16 | 44 | AAACATGACAATATGTGCTGCCACTACACA |
| 17 | 45 | TAATTTAACATTATGTGCCTCTACACAAAA |
| 18 | 51 | GCCACTGCTGCGGTTTCCCCACATTTACTC |
| 19 | 52 | GACTTTATGTGCTGAGGTTAAAAAGGAAAG |
| 20 | 53 | CGCAACCACACAGTCTATGTCTACATATAA |
| 21 | 54 | ACAGCATCCACGCAGGATAGCTTTAATAAT |
| 22 | 56 | CATGACTATTAGTACTGCTACCAGAACAGT |
| 23 | 58 | ATGACATTATGCACTGAAGTAACTAAGGAA |
| 24 | 59 | CTTTCTGTGTGTGCTTCTACTACTTCTTCT |
| 25 | 61 | CATTTGTACTGCTACATCCCCCCCTGTATC |
| 26 | 62 | ACCGCCTCCACTGCTGCAGCAGAATACACG |
| 27 | 66 | GACTATTAATGCAGCTAAAAGCACATTAAC |
| 28 | 67 | TCTGAGGAAAAATCAGAGGCTACATACAAA |
| 29 | 68 | ATTGTCCACTACTACAGACTCTACTGTACC |
| 30 | 69 | ACTGTATCTGCACAATCTGCATCTGCCACT |
| 31 | 70 | GTCTGCCTGCACCGAAACGGCCATACCTGC |
| 32 | 71 | ACCAAAACTGTTGAGTCTACATATAAAGCC |
| 33 | 72 | CAGCTTCTAATTTTCGTGAGTATCTTCGCC |
| 34 | 73 | TAGGTACACAGGCTAGTAGCTCTACTACAA |
| 35 | 74 | TAACATGACTGTGTGTGCTCCTACCTCACA |
| 36 | 81 | TACTATTTGCACAGCTACATCTGCTGCTGC |
| 37 | 82 | GCTGTTACTCCATCTGTTGCACAAACATTT |
| 38 | 83 | CAGCTGCTGCTACACAGGCTAATGAATACA |
| 39 | 84 | GCTACCAACACCGAATCAGAATATAAACCT |
| 40 | 85 | TGCAACTACTAATCCAGTTCCATCTATATA |
| 41 | 86 | TAATTTTACTATTAGTGCCGCTACCCAGAA |
| 42 | 87 | CAATTTTACTATTAGTGCTGCCACTCAAAC |
| 43 | 89 | GCTTCCCAGTCTGGCACAGAATAC |
| 44 | 90 | CACCAATATGACTATTTGTGCCACACAAAC |
| 45 | 91 | TAACTTAACCTTGTGTGCATCCACTGAGTC |
| 46 | 97 | TCTACACAAAATGGCGTAGCTACCACATAT |

TABLE 4

Determination of specificity and sensitivity of the 46 probes (columns) for hybridization with the cognate HPV DNA amplified from cloned controls for each HPV type (rows).

| Sample | HPV 6 | HPV 11 | HPV 13 | HPV 16 | HPV 18 | HPV 26 | HPV 30 |
|---|---|---|---|---|---|---|---|
| HPV 6 | 2004 | 0 | 2 | 0 | 0 | 0 | 0 |
| HPV 11 | 17 | 1445 | -8 | -7 | 57 | 5 | -5 |
| HPV 13 | 1 | 3 | 1061 | 1 | -17 | -12 | 8 |
| HPV 16 | 0 | 0 | 0 | 3378 | 0 | 0 | 0 |
| HPV 18 | 0 | 0 | 0 | 15 | 2802 | 0 | 0 |
| HPV 26 | 0 | 5 | 0 | 0 | 0 | 1961 | 0 |
| HPV 30 | 0 | 0 | 0 | 0 | 0 | 0 | 5008 |
| HPV 31 | 0 | 0 | 0 | 0 | 0 | 0 | 0 |
| HPV 32 | 0 | 0 | 0 | 0 | 0 | 0 | 0 |
| HPV 33 | 3 | 0 | 0 | 6 | 0 | 0 | 0 |
| HPV 35 | 0 | 0 | 0 | 0 | 0 | 0 | 0 |
| HPV 39 | 0 | 0 | 0 | 0 | 0 | 0 | 0 |
| HPV 40 | 0 | 0 | 0 | 0 | 0 | 0 | 0 |
| HPV 42 | 0 | 0 | 0 | 0 | 0 | 0 | 0 |
| HPV 43 | 0 | 0 | 0 | 0 | 0 | 0 | 0 |
| HPV 44 | -9 | 4 | 7 | -16 | 15 | 5 | 2 |
| HPV 45 | 0 | 0 | 0 | 0 | 0 | 0 | 0 |
| HPV 51 | 0 | 0 | 0 | 0 | 0 | 0 | 0 |
| HPV 52 | 5 | 14 | 3 | -5 | 16 | -4 | -13 |
| HPV 53 | 0 | 0 | 0 | 0 | 0 | 0 | 0 |
| HPV 54 | 0 | 0 | 0 | 0 | 0 | 0 | 0 |

| Sample | HPV 6 | HPV 11 | HPV 13 | HPV 16 | HPV 18 | HPV 26 | HPV 30 |
|---|---|---|---|---|---|---|---|
| HPV 54 | 0 | 0 | 0 | 0 | 0 | 0 | 0 |
| HPV 56 | 0 | 0 | 0 | 0 | 0 | 0 | 0 |
| HPV 58 | 0 | 0 | 0 | 0 | 0 | 0 | 0 |
| HPV 59 | 0 | 0 | 0 | 0 | 0 | 0 | 0 |
| HPV 61 | 0 | 0 | 0 | 0 | 0 | 0 | 0 |
| HPV 62 | -4 | 3 | 3 | 4 | -16 | -13 | -17 |
| HPV 66 | 0 | 0 | 0 | 0 | 0 | 0 | 0 |
| HPV 67 | 0 | 0 | 0 | 0 | 0 | 0 | 0 |
| Hpv 68 | 8 | 25 | -7 | 1 | -2 | -15 | 23 |
| HPV 69 |  | 8 | -3 | 1 | -15 | 7 | -13 |
| HPV 70 | 0 | 0 | 0 | 0 | 0 | 0 | 0 |
| HPV 71 |  | 2 | -9 | 17 | 9 | 6 | -77 |
| HPV 72 |  | 0 | 0 | 0 | 0 | 0 | 0 |
| HPV 73 |  | 5 | 34 | 15 | 2 | 12 | 18 |
| HPV 74 |  | 5 | 7 | -1 | 3 | -11 | 18 |
| HPV 81 |  | 14 | -5 | -18 | -18 | -6 | 7 |
| HPV 82 | 0 | 0 | 0 | 0 | 0 | 0 | 0 |
| HPV 83 |  | 0 | -11 | -4 | 1 | -19 | -6 |
| HPV 84 |  | -10 | -9 | -6 | 10 | -2 | -2 |
| HPV 85 | 0 | 0 | 0 | 0 | 0 | 0 | 0 |
| HPV 86 |  | 7 | 6 | 13 | 32 | -1 | 7 |
| HPV 87 |  | -9 | 5 | -18 | -6 | 13 | -13 |
| HPV 89 |  | -5 | 10 | 5 | 4 | 3 | -4 |
| HPV 90 |  | 15 | -11 | 9 | 13 | 2 | -2 |
| HPV 91 |  | 19 | 10 | 22 | 14 | -2 | 1 |
| HPV 97 |  | -8 | -5 | -3 | -1 | 12 | 7 |

| Sample | HPV 31 | HPV 32 | HPV 33 | HPV 35 | HPV 39 | HPV 40 | HPV 42 |
|---|---|---|---|---|---|---|---|
| HPV 6 | 0 | 0 | 5 | 0 | 0 | 0 | 0 |
| HPV 11 | -23 | 1 | -91 | 10 | 0 | -13 | -3 |
| HPV 13 | -45 | -2 | -106 | -13 | -6 | 13 | -11 |
| HPV 16 | 0 | 9 | 9 | 7 | 0 | 0 | 0 |
| HPV 18 | 1 | 0 | 0 | 0 | 0 | 0 | 0 |
| HPV 26 | 0 | 9 | 0 | 0 | 2 | 0 | 0 |
| HPV 30 | 0 | 0 | 17 | 0 | 0 | 0 | 0 |
| HPV 31 | 1168 | 0 | 27 | 0 | 11 | 0 | 0 |
| HPV 32 | 0 | 2601 | 5 | 0 | 0 | 0 | 0 |
| HPV 33 | 0 | 2 | 1083 | 0 | 0 | 0 | 2 |
| HPV 35 | 0 | 0 | 13 | 2348 | 1 | 0 | 0 |
| HPV 39 | 0 | 0 | 0 | 0 | 3554 | 0 | 0 |
| HPV 40 | 0 | 0 | 0 | 0 | 0 | 4154 | 0 |
| HPV 42 | 0 | 0 | 0 | 0 | 0 | 0 | 3689 |
| HPV 43 | 0 | 0 | 0 | 0 | 0 | 0 | 0 |
| HPV 44 | -23 | -4 | 12 | 0 | -3 | 1 | -7 |
| HPV 45 | 0 | 0 | 0 | 0 | 0 | 0 | 0 |
| HPV 51 | 0 | 0 | 0 | 2 | 0 | 0 | 0 |
| HPV 52 | 4 | 11 | -24 | 23 | 2 | 13 | -13 |

TABLE 4-continued

Determination of specificity and sensitivity of the 46 probes (columns) for hybridization with the cognate HPV DNA amplified from cloned controls for each HPV type (rows).

| | | | | | | | |
|---|---|---|---|---|---|---|---|
| HPV 53 | 0 | 0 | 0 | 0 | 0 | 0 | 0 |
| HPV 54 | 0 | 0 | 0 | 0 | 0 | 0 | 0 |

| Sample | HPV 31 | HPV 32 | HPV 33 | HPV 35 | HPV 39 | HPV 40 | HPV 42 |
|---|---|---|---|---|---|---|---|
| HPV 54 | 0 | 0 | 0 | 0 | 0 | 0 | 0 |
| HPV 56 | 0 | 0 | 0 | 0 | 0 | 0 | 0 |
| HPV 58 | 0 | 0 | 0 | 0 | 0 | 0 | 0 |
| HPV 59 | 0 | 0 | 0 | 0 | 0 | 0 | 0 |
| HPV 61 | 0 | 0 | 0 | 0 | 0 | 0 | 0 |
| HPV 62 | -10 | -41 | -6 | 7 | 0 | -3 | -4 |
| HPV 66 | 0 | 0 | 0 | 0 | 0 | 0 | 0 |
| HPV 67 | 0 | 0 | 0 | 0 | 0 | 0 | 0 |
| Hpv 68 | 4 | 1 | -62 | -5 | 3 | -11 | 3 |
| HPV 69 | -34 | 25 | -56 | 0 | 4 | 3 | 2 |
| HPV 70 | 0 | 0 | 0 | 0 | 0 | 0 | 0 |
| HPV 71 | -7 | -58 | -7 | -9 | 13 | 12 | -8 |
| HPV 72 | 0 | 0 | 0 | 14 | 0 | 0 | 0 |
| HPV 73 | 32 | 12 | 23 | 22 | 18 | 2 | 22 |
| HPV 74 | -4 | -1 | -40 | -4 | 4 | 6 | 20 |
| HPV 81 | 30 | 9 | 59 | 18 | -3 | 1 | 34 |
| HPV 82 | 0 | 0 | 0 | 0 | 0 | 0 | 0 |
| HPV 83 | -7 | 9 | -46 | 7 | -17 | -3 | 14 |
| HPV 84 | -12 | 7 | -4 | 9 | 18 | 7 | -4 |
| HPV 85 | 0 | 0 | 0 | 0 | 0 | 0 | 0 |
| HPV 86 | -15 | 23 | -10 | 16 | -3 | 1 | 12 |
| HPV 87 | -10 | -7 | -46 | -13 | 7 | 3 | 6 |
| HPV 89 | -18 | 15 | -5 | -13 | -5 | 2 | -2 |
| HPV 90 | 8 | 10 | -6 | 33 | 0 | 32 | 43 |
| HPV 91 | 17 | 3 | 8 | -3 | 22 | 13 | 9 |
| HPV 97 | -2 | 4 | -30 | 4 | -4 | -7 | -2 |

| Sample | HPV 43 | HPV 44 | HPV 45 | HPV 51 | HPV 52 | HPV 53 | HPV 54 |
|---|---|---|---|---|---|---|---|
| HPV 6 | 0 | 0 | 0 | 0 | 0 | 0 | 0 |
| HPV 11 | -15 | -9 | -19 | 15 | -5 | -7 | -6 |
| HPV 13 | -6 | -12 | -14 | -30 | 5 | 8 | -11 |
| HPV 16 | 0 | 5 | 0 | 0 | 0 | 0 | 0 |
| HPV 18 | 0 | 8 | 5 | 0 | 0 | 0 | 0 |
| HPV 26 | 9 | 0 | 0 | 18 | 0 | 0 | 0 |
| HPV 30 | 0 | 6 | 14 | 0 | 0 | 0 | 6 |
| HPV 31 | 0 | 0 | 0 | 0 | 0 | 0 | 0 |
| HPV 32 | 0 | 0 | 0 | 0 | 0 | 0 | 0 |
| HPV 33 | 4 | 0 | 0 | 8 | 0 | 0 | 0 |
| HPV 35 | 0 | 3 | 0 | 0 | 0 | 0 | 0 |
| HPV 39 | 0 | 0 | 0 | 0 | 0 | 0 | 0 |
| HPV 40 | 0 | 0 | 0 | 0 | 0 | 0 | 0 |
| HPV 42 | 0 | 0 | 0 | 0 | 0 | 0 | 0 |
| HPV 43 | 3364 | 0 | 0 | 0 | 0 | 0 | 0 |
| HPV 44 | 27 | 2068 | -8 | -31 | 0 | 14 | 2 |
| HPV 45 | 0 | 0 | 1922 | 0 | 0 | 0 | 0 |
| HPV 51 | 0 | 0 | 0 | 2884 | 0 | 0 | 0 |
| HPV 52 | 0 | 0 | 6 | 22 | -20 | 2429 | -10 | -5 |
| HPV 53 | 0 | 0 | 0 | 0 | 0 | 2162 | 0 |
| HPV 54 | 0 | 0 | 0 | 0 | 0 | 0 | 2755 |

| Sample | HPV 43 | HPV 44 | HPV 45 | HPV 51 | HPV 52 | HPV 53 | HPV 54 |
|---|---|---|---|---|---|---|---|
| HPV 54 | 0 | 0 | 0 | 0 | 0 | 0 | 2755 |
| HPV 56 | 0 | 0 | 0 | 0 | 0 | 0 | 0 |
| HPV 58 | 0 | 0 | 0 | 0 | 0 | 0 | 0 |
| HPV 59 | 0 | 0 | 0 | 0 | 0 | 0 | 0 |
| HPV 61 | 0 | 0 | 0 | 0 | 0 | 0 | 0 |
| HPV 62 | 12 | 0 | -6 | -5 | 1 | -3 | -19 |
| HPV 66 | 0 | 0 | 0 | 0 | 0 | 0 | 0 |
| HPV 67 | 0 | 0 | 0 | 0 | 0 | 0 | 0 |
| Hpv 68 | 8 | -12 | -3 | -14 | -7 | 8 | 6 |
| HPV 69 | 8 | 9 | 3 | -1 | 2 | 0 | 27 |
| HPV 70 | 0 | 0 | 0 | 0 | 0 | 0 | 0 |
| HPV 71 | -15 | -10 | 11 | -1 | -10 | 1 | -9 |
| HPV 72 | 0 | 0 | 0 | 0 | 0 | 0 | 0 |
| HPV 73 | 35 | 24 | 31 | 20 | 17 | 0 | 17 |
| HPV 74 | 4 | -3 | -13 | 3 | -3 | 5 | -11 |

TABLE 4-continued

Determination of specificity and sensitivity of the 46
probes (columns) for hybridization with the
cognate HPV DNA amplified from cloned
controls for each HPV type (rows).

| | | | | | | | | |
|---|---|---|---|---|---|---|---|---|
| HPV 81 | 33 | 36 | -12 | 7 | -8 | 13 | -10 | |
| HPV 82 | 0 | 0 | 0 | 0 | 0 | 0 | 0 | |
| HPV 83 | -3 | 2 | -14 | -2 | 2 | -9 | 4 | |
| HPV 84 | 4 | -15 | 13 | -22 | -11 | -16 | 11 | |
| HPV 85 | 0 | 0 | 0 | 0 | 0 | 0 | 0 | |
| HPV 86 | 6 | 391 | 10 | 26 | 19 | 24 | 4 | |
| HPV 87 | 14 | -9 | -12 | 5 | 12 | 10 | -16 | |
| HPV 89 | -1 | 6 | 3 | -7 | -11 | -4 | -4 | |
| HPV 90 | 5 | 19 | -14 | 2 | 6 | 22 | 4 | |
| HPV 91 | 19 | 9 | 8 | 11 | 17 | 21 | 15 | |
| HPV 97 | -12 | 10 | 9 | 3 | 28 | 1 | 2 | |

| Sample | HPV 56 | HPV 58 | HPV 59 | HPV 61 | HPV 62 | HPV 66 | HPV 67 | HPV 68 | HPV 69 |
|---|---|---|---|---|---|---|---|---|---|
| HPV 6 | 0 | 0 | 0 | 5 | 0 | 0 | 0 | 0 | 0 |
| HPV 11 | -3 | 14 | 2 | -13 | 6 | -4 | 5 | -1 | -10 |
| HPV 13 | 10 | -6 | -15 | -3 | -11 | -10 | -19 | 16 | -12 |
| HPV 16 | 0 | 0 | 0 | 6 | 0 | 0 | 0 | 0 | 0 |
| HPV 18 | 0 | 0 | 0 | 0 | 0 | 0 | 0 | 0 | 0 |
| HPV 26 | 0 | 0 | 0 | 0 | 0 | 0 | 0 | 0 | 0 |
| HPV 30 | 4 | 0 | 0 | 0 | 0 | 0 | 14 | 0 | 14 |
| HPV 31 | 0 | 0 | 0 | 0 | 0 | 0 | 0 | 0 | 0 |
| HPV 32 | 0 | 0 | 0 | 0 | 18 | 0 | 16 | 18 | 0 |
| HPV 33 | 0 | 0 | 0 | 0 | 0 | 0 | 4 | 0 | 15 |
| HPV 35 | 7 | 0 | 0 | 0 | 0 | 0 | 23 | 6 | 0 |
| HPV 39 | 0 | 0 | 0 | 5 | 0 | 0 | 0 | 0 | 0 |
| HPV 40 | 0 | 0 | 0 | 0 | 0 | 0 | 0 | 0 | 0 |
| HPV 42 | 0 | 0 | 0 | 0 | 0 | 0 | 0 | 0 | 0 |
| HPV 43 | 0 | 0 | 0 | 0 | 0 | 0 | 0 | 0 | 0 |
| HPV 44 | -13 | -4 | 5 | -8 | -15 | -12 | -3 | 20 | -9 |
| HPV 45 | 0 | 0 | 0 | 0 | 0 | 0 | 0 | 0 | 0 |
| HPV 51 | 0 | 0 | 0 | 0 | 0 | 0 | 0 | 0 | 0 |
| HPV 52 | -4 | 16 | -5 | -6 | 0 | -5 | -31 | -3 | 5 |
| HPV 53 | 0 | 0 | 0 | 0 | 0 | 0 | 0 | 0 | 0 |
| HPV 54 | 0 | 0 | 0 | 0 | 0 | 0 | 0 | 0 | 0 |

| Sample | HPV 56 | HPV 58 | HPV 59 | HPV 61 | HPV 62 | HPV 66 | HPV 67 | HPV 68 | HPV 69 |
|---|---|---|---|---|---|---|---|---|---|
| HPV 56 | 1638 | 0 | 0 | 0 | 0 | 0 | 0 | 0 | 0 |
| HPV 58 | 0 | 1874 | 0 | 0 | 0 | 0 | 0 | 0 | 0 |
| HPV 59 | 0 | 0 | 3405 | 0 | 0 | 0 | 0 | 0 | 0 |
| HPV 61 | 0 | 0 | 0 | 3831 | 0 | 0 | 0 | 0 | 0 |
| HPV 62 | -11 | -13 | -6 | 2 | 2298 | -2 | -12 | 10 | 14 |
| HPV 66 | 0 | 0 | 0 | 0 | 0 | 1258 | 0 | 0 | 0 |
| HPV 67 | 0 | 0 | 0 | 0 | 0 | 0 | 1115 | 0 | 0 |
| Hpv 68 | 6 | -11 | -18 | 15 | -6 | 8 | 12 | 957 | 5 |
| HPV 69 | -10 | 7 | -12 | -1 | -4 | 8 | -8 | 21 | 1909 |
| HPV 70 | 0 | 0 | 0 | 0 | 0 | 0 | 0 | 0 | 0 |
| HPV 71-3 | 1 | | -1 | -2 | -17 | 20 | -11 | -19 | -2 |
| HPV 72 | 0 | 0 | 0 | 0 | 0 | 0 | 0 | 0 | 0 |
| HPV 73 | 11 | 0 | 0 | 25 | 38 | 4 | 37 | 23 | 39 |
| HPV 74 | -10 | -3 | 5 | 20 | -4 | 3 | 15 | 8 | 1 |
| HPV 81 | -9 | 0 | -27 | 3 | -10 | -10 | 47 | 47 | 4 |
| HPV 82 | 0 | 0 | 0 | 0 | 0 | 0 | 0 | 0 | 0 |
| HPV 83 | 15 | -3 | -9 | 9 | -15 | 11 | -6 | 8 | 2 |
| HPV 84 | -12 | 0 | 3 | -2 | 1 | -6 | -16 | 17 | -9 |
| HPV 85 | 0 | 0 | 0 | 0 | 0 | 0 | 6 | 0 | 0 |
| HPV 86 | 15 | -2 | -3 | 1 | 6 | 12 | 5 | 32 | 14 |
| HPV 87 | -7 | -13 | -8 | -8 | 16 | -13 | 7 | 31 | 3 |
| HPV 89 | -3 | -3 | -1 | -5 | 4 | 15 | 7 | 7 | -14 |
| HPV 90 | 1 | -6 | 2 | 11 | 6 | 5 | -24 | 40 | -10 |
| HPV 91 | 11 | 3 | -3 | 13 | 9 | 5 | 32 | 16 | 15 |
| HPV 97 | -3 | -6 | 5 | -16 | -4 | -9 | -8 | 3 | 7 |

| Sample | HPV 70 | HPV 71 | HPV 72 | HPV 73 | HPV 74 | HPV 81 | HPV 82 | HPV 83 |
|---|---|---|---|---|---|---|---|---|
| HPV 6 | 1 | 2 | 0 | 0 | 0 | 0 | 2 | 0 |
| HPV 11 | -10 | 143 | -10 | 2 | -6 | -9 | -18 | -6 |
| HPV 13 | 0 | -11 | 254 | 4 | 26 | 5 | -12 | -15 |
| HPV 16 | 0 | 0 | 15 | 0 | 4 | 0 | 0 | 0 |
| HPV 18 | 0 | 3 | 12 | 0 | 0 | 0 | 0 | 0 |
| HPV 26 | 0 | 0 | 21 | 0 | 0 | 0 | 1 | 0 |
| HPV 30 | 0 | 8 | 0 | 0 | 0 | 0 | 0 | 0 |

TABLE 4-continued

Determination of specificity and sensitivity of the 46 probes (columns) for hybridization with the cognate HPV DNA amplified from cloned controls for each HPV type (rows).

| | | | | | | | | |
|---|---|---|---|---|---|---|---|---|
| HPV 31 | 0 | 0 | 5 | 0 | 11 | 0 | 0 | 0 |
| HPV 32 | 0 | 0 | 13 | 0 | 3 | 0 | 0 | 0 |
| HPV 33 | 0 | 0 | 0 | 3 | 0 | 0 | 0 | 7 |
| HPV 35 | 0 | 0 | 27 | 0 | 18 | 0 | 13 | 0 |
| HPV 39 | 0 | 0 | 9 | 0 | 0 | 0 | 0 | 0 |
| HPV 40 | 0 | 0 | 0 | 0 | 0 | 0 | 0 | 0 |
| HPV 42 | 0 | 0 | 0 | 0 | 0 | 0 | 0 | 0 |
| HPV 43 | 1 | 0 | 0 | 0 | 0 | 0 | 0 | 0 |
| HPV 44 | 1 | -18 | -13 | -7 | -16 | -15 | -13 | -13 |
| HPV 45 | 0 | 0 | 0 | 0 | 0 | 0 | 0 | 0 |
| HPV 51 | 0 | 0 | 0 | 0 | 0 | 0 | 0 | 0 |
| HPV 52 | -3 | -16 | 147 | 6 | 3 | 41 | -7 | -3 |
| HPV 53 | 0 | 0 | 13 | 0 | 0 | 0 | 0 | 0 |
| HPV 54 | 0 | 0 | 0 | 0 | 0 | 0 | 0 | 0 |

| Sample | HPV 70 | HPV 71 | HPV 72 | HPV 73 | HPV 74 | HPV 81 | HPV 82 | HPV 83 |
|---|---|---|---|---|---|---|---|---|
| HPV 56 | 0 | 0 | 78 | 0 | 0 | 0 | 0 | 0 |
| HPV 58 | 0 | 0 | 0 | 0 | 0 | 0 | 0 | 0 |
| HPV 59 | 0 | 0 | 0 | 0 | 0 | 0 | 0 | 0 |
| HPV 61 | 0 | 0 | 1 | 0 | 0 | 0 | 0 | 0 |
| HPV 62 | 3 | -6 | -119 | -10 | -7 | 0 | -10 | -9 |
| HPV 66 | 0 | 0 | 0 | 0 | 0 | 0 | 0 | 0 |
| HPV 67 | 0 | 0 | 0 | 0 | 0 | 0 | 0 | 0 |
| Hpv 68 | 6 | -6 | -106 | 9 | 10 | -9 | 3 | 3 |
| HPV 69 | 17 | -8 | -131 | -3 | 16 | 20 | -17 | -5 |
| HPV 70 | 3971 | 0 | 0 | 0 | 0 | 0 | 0 | 0 |
| HPV 71 | -5 | 1166 | -229 | -1 | -17 | -8 | -3 | -13 |
| HPV 72 | 0 | 0 | 2213 | 0 | 0 | 0 | 0 | 0 |
| HPV 73 | 23 | 18 | 20 | 1715 | 18 | 9 | 24 | 36 |
| HPV 74 | 16 | 2 | -127 | -3 | 1044 | -12 | 5 | 7 |
| HPV 81 | 1 | -16 | 115 | -15 | -14 | 2343 | -10 | -6 |
| HPV 82 | 0 | 0 | 1 | 0 | 0 | 0 | 2259 | 0 |
| HPV 83 | -12 | -11 | -142 | 6 | -6 | -5 | 5 | 2625 |
| HPV 84 | 12 | -15 | -82 | -12 | 3 | 10 | -2 | 11 |
| HPV 85 | 0 | 0 | 0 | 0 | 0 | 0 | 0 | 0 |
| HPV 86 | 6 | 28 | -115 | 5 | -2 | 8 | 8 | 2 |
| HPV 87 | -3 | -8 | -183 | -1 | 7 | 14 | 4 | 2 |
| HPV 89 | 6 | -7 | -68 | -14 | 3 | -5 | 0 | -17 |
| HPV 90 | -16 | 3 | -122 | 1 | -4 | 6 | -6 | 20 |
| HPV 91 | 9 | 23 | -51 | 16 | 9 | 7 | 17 | -9 |
| HPV 97 | -4 | -1 | -73 | 2 | -11 | -7 | -10 | 16 |

| Sample | HPV 84 | HPV 85 | HPV 86 | HPV 87 | HPV 89 | HPV 90 | HPV 91 | HPV 97 |
|---|---|---|---|---|---|---|---|---|
| HPV 6 | 0 | 0 | 0 | 11 | 0 | 0 | 0 | 17 |
| HPV 11 | 4 | -9 | -9 | -3 | -16 | 1 | 0 | 23 |
| HPV 13 | -8 | -3 | 18 | 1 | -12 | 2 | 1 | 28 |
| HPV 16 | 6 | 4 | 0 | 0 | 0 | 0 | 0 | 28 |
| HPV 18 | 9 | 0 | 0 | 0 | 0 | 0 | 0 | -4 |
| HPV 26 | 0 | 0 | 0 | 0 | 0 | 0 | 0 | 18 |
| HPV 30 | 0 | 0 | 0 | 0 | 0 | 0 | 0 | 12 |
| HPV 31 | 0 | 0 | 0 | 0 | 0 | 11 | 0 | 14 |
| HPV 32 | 0 | 14 | 0 | 0 | 0 | 0 | 9 | 28 |
| HPV 33 | 16 | 0 | 0 | 4 | 0 | 0 | 0 | 24 |
| HPV 35 | 0 | 8 | 0 | 0 | 0 | 5 | 0 | 24 |
| HPV 39 | 0 | 0 | 0 | 0 | 0 | 0 | 0 | 12 |
| HPV 40 | 0 | 0 | 0 | 0 | 0 | 0 | 0 | 28 |
| HPV 42 | 0 | 0 | 0 | 0 | 0 | 0 | 0 | 11 |
| HPV 43 | 0 | 0 | 0 | 0 | 0 | 0 | 0 | 27 |
| HPV 44 | -4 | 8 | 11 | -4 | 513 | -5 | 8 | 28 |
| HPV 45 | 0 | 0 | 0 | 0 | 0 | 0 | 0 | 0 |
| HPV 51 | 0 | 0 | 0 | 0 | 0 | 0 | 0 | 16 |
| HPV 52 | -9 | 5 | 23 | 8 | -6 | 7 | -2 | -8 |
| HPV 53 | 0 | 0 | 0 | 0 | 0 | 0 | 0 | 21 |
| HPV 54 | 0 | 0 | 0 | 0 | 0 | 0 | 0 | 17 |

| Sample | HPV 84 | HPV 85 | HPV 86 | HPV 87 | HPV 89 | HPV 90 | HPV 91 | HPV 97 |
|---|---|---|---|---|---|---|---|---|
| HPV 56 | 0 | 0 | 0 | 0 | 0 | 0 | 0 | -25 |
| HPV 58 | 0 | 0 | 0 | 0 | 0 | 0 | 0 | 1 |

TABLE 4-continued

Determination of specificity and sensitivity of the 46 probes (columns) for hybridization with the cognate HPV DNA amplified from cloned controls for each HPV type (rows).

| | | | | | | | | |
|---|---|---|---|---|---|---|---|---|
| HPV 59 | 0 | 0 | 0 | 0 | 0 | 0 | 0 | -22 |
| HPV 61 | 0 | 0 | 0 | 0 | 0 | 0 | 0 | -21 |
| HPV 62 | 21 | -15 | -12 | -4 | 2 | -5 | 29 | -20 |
| HPV 66 | 0 | 0 | 0 | 0 | 0 | 0 | 0 | -7 |
| HPV 67 | 0 | 0 | 0 | 0 | 0 | 0 | 0 | -5 |
| Hpv 68 | 4 | -11 | -4 | -5 | -2 | 2 | 0 | -11 |
| HPV 69 | 8 | 4 | -6 | -1 | 11 | -8 | 6 | -28 |
| HPV 70 | 0 | 0 | 0 | 0 | 11 | 0 | 0 | 1 |
| HPV 71 | 10 | -13 | -4 | -19 | 4 | -18 | -5 | 10 |
| HPV 72 | 0 | 0 | 0 | 0 | 0 | 0 | 0 | -13 |
| HPV 73 | 14 | 15 | 24 | 9 | 4 | 36 | 27 | -12 |
| HPV 74 | -7 | -7 | 7 | 3 | 12 | 0 | 19 | 1 |
| HPV 81 | -20 | -7 | 4 | 5 | -3 | 7 | -9 | -18 |
| HPV 82 | 0 | 0 | 0 | 0 | 0 | 0 | 0 | -14 |
| HPV 83 | 19 | -17 | 6 | 6 | -1 | 15 | 8 | -7 |
| HPV 84 | 2194 | 19 | 0 | 15 | -13 | -5 | -15 | -16 |
| HPV 85 | 0 | 4605 | 0 | 0 | 0 | 0 | 0 | -17 |
| HPV 86 | 18 | 5 | 1720 | 35 | 12 | 13 | 2 | -10 |
| HPV 87 | -3 | -1 | 8 | 1828 | 12 | 7 | 1 | 0 |
| HPV 89 | 9 | 12 | -13 | -10 | 3998 | -27 | 1 | -19 |
| HPV 90 | 13 | 7 | 15 | 16 | 23 | 3613 | 5 | -13 |
| HPV 91 | -8 | 6 | 14 | 21 | 24 | 31 | 2264 | -16 |
| HPV 97 | 6 | 2 | -20 | -3 | -3 | -7 | -11 | 1267 |

TABLE 5

Comparison of NML Luminex with direct sequencing for detection of any HPV type

| | Direct sequencing | | |
|---|---|---|---|
| NML Luminex | Negative | Positive | Totals |
| Positive | 14 | 429 | 442 |
| Negative | 348 | 5 | 353 |
| Totals | 361 | 434 | 795 |

TABLE 6

Distribution of HPV types as detected by NML Luminex and direct sequencing

| | NML LUMINEX | | | Direct Sequencing | | |
|---|---|---|---|---|---|---|
| HPV type | n | % of types | % of positive samples | n | % of types | % of positive samples |
| 6 | 43 | 7.5% | 5.4% | 39 | 4.9% | 4.9% |
| 11 | 12 | 2.1% | 1.5% | 11 | 1.4% | 1.4% |
| 13 | 0 | 0.0% | 0.0% | 0 | 0.0% | 0.0% |
| 16 | 87 | 15.1% | 10.9% | 68 | 8.6% | 8.6% |
| 18 | 26 | 4.5% | 3.3% | 15 | 1.9% | 1.9% |
| 26 | 0 | 0.0% | 0.0% | 0 | 0.0% | 0.0% |
| 30 | 2 | 0.3% | 0.3% | 0 | 0.0% | 0.0% |
| 31 | 29 | 5.0% | 3.6% | 29 | 3.7% | 3.6% |
| 32 | 3 | 0.5% | 0.4% | 2 | 0.3% | 0.3% |
| 33 | 11 | 1.9% | 1.4% | 14 | 1.8% | 1.8% |
| 35 | 8 | 1.4% | 1.0% | 2 | 0.3% | 0.3% |
| 39 | 22 | 3.8% | 2.8% | 16 | 2.0% | 2.0% |
| 40 | 9 | 1.6% | 1.1% | 5 | 0.6% | 0.6% |
| 42 | 13 | 2.3% | 1.6% | 5 | 0.6% | 0.6% |
| 43 | 0 | 0.0% | 0.0% | 1 | 0.1% | 0.1% |
| 44 | 3 | 0.5% | 0.4% | 1 | 0.1% | 0.1% |
| 45 | 12 | 2.1% | 1.5% | 10 | 1.3% | 1.3% |
| 51 | 16 | 2.8% | 2.0% | 9 | 1.1% | 1.1% |
| 52 | 33 | 5.7% | 4.2% | 17 | 2.1% | 2.1% |
| 53 | 25 | 4.3% | 3.1% | 12 | 1.5% | 1.5% |
| 54 | 11 | 1.9% | 1.4% | 8 | 1.0% | 1.0% |
| 56 | 10 | 1.7% | 1.3% | 4 | 0.5% | 0.5% |
| 58 | 28 | 4.9% | 3.5% | 25 | 3.2% | 3.1% |
| 59 | 11 | 1.9% | 1.4% | 5 | 0.6% | 0.6% |
| 61 | 7 | 1.2% | 0.9% | 1 | 0.1% | 0.1% |
| 62 | 26 | 4.5% | 3.3% | 17 | 2.1% | 2.1% |
| 66 | 39 | 6.8% | 4.9% | 30 | 3.8% | 3.8% |
| 67 | 7 | 1.2% | 0.9% | 8 | 1.0% | 1.0% |
| 68 | 2 | 0.3% | 0.3% | 4 | 0.5% | 0.5% |
| 69 | 3 | 0.5% | 0.4% | 2 | 0.3% | 0.3% |
| 70 | 11 | 1.9% | 1.4% | 10 | 1.3% | 1.3% |
| 71 | 3 | 0.5% | 0.4% | 0 | 0.0% | 0.0% |
| 72 | 5 | 0.9% | 0.6% | 4 | 0.5% | 0.5% |
| 73 | 5 | 0.9% | 0.6% | 3 | 0.4% | 0.4% |
| 74 | 1 | 0.2% | 0.1% | 0 | 0.0% | 0.0% |
| 81 | 8 | 1.4% | 1.0% | 6 | 0.8% | 0.8% |
| 82 | 7 | 1.2% | 0.9% | 5 | 0.6% | 0.6% |
| 83 | 11 | 1.9% | 1.4% | 5 | 0.6% | 0.6% |
| 84 | 12 | 2.1% | 1.5% | 1 | 0.1% | 0.1% |
| 85 | 2 | 0.3% | 0.3% | 2 | 0.3% | 0.3% |
| 86 | 1 | 0.2% | 0.1% | 1 | 0.1% | 0.1% |
| 87 | 2 | 0.3% | 0.3% | 3 | 0.4% | 0.4% |
| 89 | 8 | 1.4% | 1.0% | 4 | 0.5% | 0.5% |
| 90 | 3 | 0.5% | 0.4% | 1 | 0.1% | 0.1% |
| 91 | 1 | 0.2% | 0.1% | 0 | 0.0% | 0.0% |
| 102 | N/A | N/A | N/A | 2 | 0.3% | 0.3% |

TABLE 7

Comparison of NML Luminex vs Roche linear array for detection of samples positive for any HPV type.

| NML Luminex | Roche Linear Array Negative | Positive | Totals |
|---|---|---|---|
| Positive | 46 | 394 | 440 |
| Negative | 424 | 16 | 440 |
| Totals | 470 | 410 | 880 |

TABLE 8

Comparison between NML Luminex and Roche Linear array in the ability to detect multiple HPV infections.

|  | NML Luminex | Roche Linear Array |
|---|---|---|
| Positive for any type | 435 | 405 |
| Total HPV types detected | 917 | 1111 |
| Single infections | 200 | 156 |
| Multiple infections | 235 | 249 |
| 2 types | 122 | 87 |
| 3 types | 49 | 59 |
| 4+ types | 64 | 103 |

TABLE 9

Comparison of HPV type distribution as detected by NML Luminex and the Roche Linear Array method.

|  | NML Luminex n | NML Luminex % | Roche Linear Array n | Roche Linear Array % |
|---|---|---|---|---|
| HPV06 | 48 | 5.2% | 49 | 4.4% |
| HPV11 | 39 | 4.3% | 45 | 4.1% |
| HPV13* | 0 | 0.0% |  |  |
| HPV16 | 136 | 14.8% | 137 | 12.3% |
| HPV18 | 47 | 5.1% | 41 | 3.7% |
| HPV26 | 0 | 0.0% | 3 | 0.3% |
| HPV30* | 2 | 0.2% |  |  |
| HPV31 | 31 | 3.4% | 48 | 4.3% |
| HPV32* | 11 | 1.2% |  |  |
| HPV33 | 15 | 1.6% | 16 | 1.4% |
| HPV35 | 30 | 3.3% | 23 | 2.1% |
| HPV39 | 27 | 2.9% | 39 | 3.5% |
| HPV40 | 10 | 1.1% | 8 | 0.7% |
| HPV42 | 30 | 3.3% | 38 | 3.4% |
| HPV43* | 3 | 0.3% |  |  |
| HPV44 | 11 | 1.2% | 16 | 1.4% |
| HPV45 | 34 | 3.7% | 30 | 2.7% |
| HPV51 | 31 | 3.4% | 57 | 5.1% |
| HPV52** | 26 | 2.8% | 74 | 6.7% |
| HPV53** | 25 | 2.7% | 53 | 4.8% |
| HPV54 | 14 | 1.5% | 21 | 1.9% |
| HPV56 | 34 | 3.7% | 29 | 2.6% |
| HPV58 | 27 | 2.9% | 30 | 2.7% |
| HPV59 | 31 | 3.4% | 44 | 4.0% |
| HPV61** | 10 | 1.1% | 27 | 2.4% |
| HPV62 | 14 | 1.5% | 30 | 2.7% |
| HPV66 | 38 | 4.1% | 38 | 3.4% |
| HPV67** | 19 | 2.1% | 6 | 0.5% |
| HPV68 | 13 | 1.4% | 21 | 1.9% |
| HPV69 | 9 | 1.0% | 9 | 0.8% |
| HPV70 | 30 | 3.3% | 29 | 2.6% |
| HPV71 | 1 | 0.1% | 1 | 0.1% |
| HPV72 | 7 | 0.8% | 12 | 1.1% |
| HPV73** | 6 | 0.7% | 18 | 1.6% |
| HPV74* | 12 | 1.3% |  |  |
| HPV81 | 12 | 1.3% | 12 | 1.1% |
| HPV82 | 4 | 0.4% | 11 | 1.0% |
| HPV83 | 12 | 1.3% | 18 | 1.6% |
| HPV84** | 18 | 2.0% | 39 | 3.5% |
| HPV85* | 5 | 0.5% |  |  |
| HPV86* | 11 | 1.2% |  |  |
| HPV87 | 4 | 0.4% |  |  |
| HPV89** | 18 | 2.0% | 38 | 3.4% |
| HPV90* | 12 | 1.3% |  |  |
| HPV91* | 0 | 0.0% |  |  |

*Type not detected by the Roche Linear Array
**Statistically significant difference (p < 0.05)

TABLE 10

Comparison of HPV type distribution as detected by NML Luminex and the Roche Linear Array method when multiple infections with 4 or more types are excluded.

| Strain | NML Luminex n | NML Luminex % | Roche Linear Array n | Roche Linear Array % |
|---|---|---|---|---|
| HPV06 | 26 | 4.9% | 23 | 4.3% |
| HPV11 | 26 | 4.9% | 30 | 5.6% |
| HPV13* | 0 | 0 |  |  |
| HPV16 | 86 | 16.1% | 90 | 16.9% |
| HPV18 | 24 | 4.5% | 17 | 3.2% |
| HPV26 | 0 | 0% | 0 | 0% |
| HPV30* | 1 | 0.2% |  |  |
| HPV31 | 24 | 4.5% | 25 | 4.7% |
| HPV32* | 5 | 0.9% | 0 | 0.0% |
| HPV33 | 7 | 1.3% | 5 | 0.9% |
| HPV35 | 14 | 2.6% | 8 | 1.5% |
| HPV39 | 15 | 2.8% | 16 | 3.0% |
| HPV40 | 8 | 1.5% | 4 | 0.7% |
| HPV42 | 21 | 3.9% | 21 | 3.9% |
| HPV43* | 2 | 0.4% |  |  |
| HPV44 | 9 | 1.7% | 5 | 0.9% |
| HPV45 | 12 | 2.2% | 8 | 1.5% |
| HPV51 | 23 | 4.3% | 29 | 5.4% |
| HPV52** | 15 | 2.8% | 34 | 6.4% |
| HPV53 | 19 | 3.6% | 25 | 4.7% |
| HPV54 | 10 | 1.9% | 12 | 2.2% |
| HPV56 | 20 | 3.7% | 11 | 2.1% |
| HPV58 | 14 | 2.6% | 11 | 2.1% |
| HPV59 | 11 | 2.1% | 16 | 3.0% |
| HPV61 | 6 | 1.1% | 14 | 2.6% |
| HPV62 | 10 | 1.9% | 16 | 3.0% |
| HPV66 | 21 | 3.9% | 19 | 3.6% |
| HPV67** | 10 | 1.9% | 2 | 0.4% |
| HPV68 | 9 | 1.7% | 8 | 1.5% |
| HPV69 | 5 | 0.9% | 5 | 0.9% |
| HPV70 | 15 | 2.8% | 12 | 2.2% |
| HPV71 | 0 | 0% |  |  |
| HPV72 | 4 | 0.7% | 6 | 1.1% |
| HPV73 | 4 | 0.7% | 9 | 1.7% |
| HPV74* | 7 | 1.3% | 0 | 0.0% |
| HPV81 | 4 | 0.7% | 3 | 0.6% |
| HPV82 | 2 | 0.4% | 4 | 0.7% |
| HPV83 | 8 | 1.5% | 10 | 1.9% |
| HPV84 | 10 | 1.9% | 17 | 3.2% |
| HPV85* | 2 | 0.4% |  |  |
| HPV86* | 5 | 0.9% |  |  |
| HPV87 | 1 | 0.2% |  |  |
| HPV89 | 11 | 2.1% | 18 | 3.4% |
| HPV90* | 9 | 1.7% |  |  |
| HPV91* | 0 | 0% |  |  |

The invention claimed is:

1. A method of detecting and typing a human papillomavirus (HPV) type infection in a sample comprising:
   a) providing a sample suspected of comprising at least one HPV type;
   b) adding to the sample primers suitable for amplifying the L1 region of HPV;
   c) incubating the sample under conditions suitable for DNA amplification;
   d) adding a probe consisting of the nucleotide sequence of SEQ ID NO:46, said probe binding to only HPV type 97 under hybridization conditions, said probe further comprising a unique tag, said unique tag comprising a combination of two fluorescent dyes;
   e) incubating said probe and said sample under conditions suitable for hybridization; and
   f) detecting hybridization of said probe.

2. The method according to claim 1 wherein the unique tag is a combination of different ratios of red and infra-red fluorophores.

3. The method according to claim 1 wherein the primers comprise GP5+/GP6+.

4. The method according to claim 1 wherein the primers comprise GP5+/GP6+ and MY09/MY11.

5. The method according to claim 1 wherein at least one of the primers is exonuclease resistant.

6. The method according to claim 5 wherein exonuclease is added prior to step (d).

* * * * *

SEQUENCE LISTING

<160> NUMBER OF SEQ ID NOS: 276

<210> SEQ ID NO 1
<211> LENGTH: 30
<212> TYPE: DNA
<213> ORGANISM: Human papillomavirus type 6

<400> SEQUENCE: 1
catcttccac ataccaat tctgattata                                    30

<210> SEQ ID NO 2
<211> LENGTH: 30
<212> TYPE: DNA
<213> ORGANISM: Human papillomavirus type 11

<400> SEQUENCE: 2
actatgtgca tctgtgtcta aatctgctac                                  30

<210> SEQ ID NO 3
<211> LENGTH: 30
<212> TYPE: DNA
<213> ORGANISM: Human papillomavirus type 13

<400> SEQUENCE: 3
gtgtgtgcag ccactacatc atctctttca                                  30

<210> SEQ ID NO 4
<211> LENGTH: 30
<212> TYPE: DNA
<213> ORGANISM: Human papillomavirus type 16

<400> SEQUENCE: 4
aaatatgtca ttatgtgctg ccatatctac                                  30

<210> SEQ ID NO 5
<211> LENGTH: 30
<212> TYPE: DNA
<213> ORGANISM: Human papillomavirus type 18

<400> SEQUENCE: 5
atatgtgctt ctacacagtc tcctgtacct                                  30

<210> SEQ ID NO 6
<211> LENGTH: 30
<212> TYPE: DNA
<213> ORGANISM: Human papillomavirus type 26

<400> SEQUENCE: 6
ccttaccatt agtacattat ctgcagcatc                                  30

<210> SEQ ID NO 7
<211> LENGTH: 30
<212> TYPE: DNA
<213> ORGANISM: Human papillomavirus type 30

<400> SEQUENCE: 7
atctgcaacc acacaaacgt tatccacata                                  30

<210> SEQ ID NO 8
<211> LENGTH: 30
<212> TYPE: DNA
<213> ORGANISM: Human papillomavirus type 31

```
<400> SEQUENCE: 8
caatatgtct gtttgtgctg caattgcaaa                                    30

<210> SEQ ID NO 9
<211> LENGTH: 30
<212> TYPE: DNA
<213> ORGANISM: Human papillomavirus type 32

<400> SEQUENCE: 9
actgtaacaa ctgaagacac atacaagtct                                    30

<210> SEQ ID NO 10
<211> LENGTH: 30
<212> TYPE: DNA
<213> ORGANISM: Human papillomavirus type 33

<400> SEQUENCE: 10
taatatgact ttatgcacac aagtaactag                                    30

<210> SEQ ID NO 11
<211> LENGTH: 30
<212> TYPE: DNA
<213> ORGANISM: Human papillomavirus type 35

<400> SEQUENCE: 11
aaatatgtct gtgtgttctg ctgtgtcttc                                    30

<210> SEQ ID NO 12
<211> LENGTH: 30
<212> TYPE: DNA
<213> ORGANISM: Human papillomavirus type 39

<400> SEQUENCE: 12
atctacctct atagagtctt ccataccttc                                    30

<210> SEQ ID NO 13
<211> LENGTH: 30
<212> TYPE: DNA
<213> ORGANISM: Human papillomavirus type 40

<400> SEQUENCE: 13
cttatgtgct gccacacagt cccccacacc                                    30

<210> SEQ ID NO 14
<211> LENGTH: 30
<212> TYPE: DNA
<213> ORGANISM: Human papillomavirus type 42

<400> SEQUENCE: 14
tctggtgata catatacagc tgctaatttt                                    30

<210> SEQ ID NO 15
<211> LENGTH: 30
<212> TYPE: DNA
<213> ORGANISM: Human papillomavirus type 43

<400> SEQUENCE: 15
aaacttaacg ttatgtgcct ctactgaccc                                    30

<210> SEQ ID NO 16
<211> LENGTH: 30
<212> TYPE: DNA
<213> ORGANISM: Human papillomavirus type 44
```

```
<400> SEQUENCE: 16
aaacatgaca atatgtgctg ccactacaca                                    30

<210> SEQ ID NO 17
<211> LENGTH: 30
<212> TYPE: DNA
<213> ORGANISM: Human papillomavirus type 45

<400> SEQUENCE: 17
taatttaaca ttatgtgcct ctacacaaaa                                    30

<210> SEQ ID NO 18
<211> LENGTH: 30
<212> TYPE: DNA
<213> ORGANISM: Human papillomavirus type 51

<400> SEQUENCE: 18
gccactgctg cggtttcccc acatttactc                                    30

<210> SEQ ID NO 19
<211> LENGTH: 30
<212> TYPE: DNA
<213> ORGANISM: Human papillomavirus type 52

<400> SEQUENCE: 19
gactttatgt gctgaggtta aaaaggaaag                                    30

<210> SEQ ID NO 20
<211> LENGTH: 30
<212> TYPE: DNA
<213> ORGANISM: Human papillomavirus type 53

<400> SEQUENCE: 20
cgcaaccaca cagtctatgt ctacatataa                                    30

<210> SEQ ID NO 21
<211> LENGTH: 30
<212> TYPE: DNA
<213> ORGANISM: Human papillomavirus type 54

<400> SEQUENCE: 21
acagcatcca cgcaggatag ctttaataat                                    30

<210> SEQ ID NO 22
<211> LENGTH: 30
<212> TYPE: DNA
<213> ORGANISM: Human papillomavirus type 56

<400> SEQUENCE: 22
catgactatt agtactgcta ccagaacagt                                    30

<210> SEQ ID NO 23
<211> LENGTH: 30
<212> TYPE: DNA
<213> ORGANISM: Human papillomavirus type 58

<400> SEQUENCE: 23
atgacattat gcactgaagt aactaaggaa                                    30

<210> SEQ ID NO 24
<211> LENGTH: 30
<212> TYPE: DNA
<213> ORGANISM: Human papillomavirus type 59
```

<400> SEQUENCE: 24
ctttctgtgt gtgcttctac tacttcttct                                                30

<210> SEQ ID NO 25
<211> LENGTH: 30
<212> TYPE: DNA
<213> ORGANISM: Human papillomavirus type 61

<400> SEQUENCE: 25
catttgtact gctacatccc ccctgtatc                                                 30

<210> SEQ ID NO 26
<211> LENGTH: 30
<212> TYPE: DNA
<213> ORGANISM: Human papillomavirus type 62

<400> SEQUENCE: 26
accgcctcca ctgctgcagc agaatacacg                                                30

<210> SEQ ID NO 27
<211> LENGTH: 30
<212> TYPE: DNA
<213> ORGANISM: Human papillomavirus type 66

<400> SEQUENCE: 27
gactattaat gcagctaaaa gcacattaac                                                30

<210> SEQ ID NO 28
<211> LENGTH: 30
<212> TYPE: DNA
<213> ORGANISM: Human papillomavirus type 67

<400> SEQUENCE: 28
tctgaggaaa aatcagaggc tacatacaaa                                                30

<210> SEQ ID NO 29
<211> LENGTH: 30
<212> TYPE: DNA
<213> ORGANISM: Human papillomavirus type 68

<400> SEQUENCE: 29
attgtccact actacagact ctactgtacc                                                30

<210> SEQ ID NO 30
<211> LENGTH: 30
<212> TYPE: DNA
<213> ORGANISM: Human papillomavirus type 69

<400> SEQUENCE: 30
actgtatctg cacaatctgc atctgccact                                                30

<210> SEQ ID NO 31
<211> LENGTH: 30
<212> TYPE: DNA
<213> ORGANISM: Human papillomavirus type 70

<400> SEQUENCE: 31
gtctgcctgc accgaaacgg ccatacctgc                                                30

<210> SEQ ID NO 32
<211> LENGTH: 30
<212> TYPE: DNA
<213> ORGANISM: Human papillomavirus

```
<400> SEQUENCE: 32
accaaaactg ttgagtctac atataaagcc                              30

<210> SEQ ID NO 33
<211> LENGTH: 30
<212> TYPE: DNA
<213> ORGANISM: Human papillomavirus type 72

<400> SEQUENCE: 33
cagcttctaa ttttcgtgag tatcttcgcc                              30

<210> SEQ ID NO 34
<211> LENGTH: 30
<212> TYPE: DNA
<213> ORGANISM: Human papillomavirus type 73

<400> SEQUENCE: 34
taggtacaca ggctagtagc tctactacaa                              30

<210> SEQ ID NO 35
<211> LENGTH: 30
<212> TYPE: DNA
<213> ORGANISM: Human papillomavirus type 74

<400> SEQUENCE: 35
taacatgact gtgtgtgctc ctacctcaca                              30

<210> SEQ ID NO 36
<211> LENGTH: 30
<212> TYPE: DNA
<213> ORGANISM: Human papillomavirus

<400> SEQUENCE: 36
tactatttgc acagctacat ctgctgctgc                              30

<210> SEQ ID NO 37
<211> LENGTH: 30
<212> TYPE: DNA
<213> ORGANISM: Human papillomavirus

<400> SEQUENCE: 37
gctgttactc catctgttgc acaaacattt                              30

<210> SEQ ID NO 38
<211> LENGTH: 30
<212> TYPE: DNA
<213> ORGANISM: Human papillomavirus

<400> SEQUENCE: 38
cagctgctgc tacacaggct aatgaataca                              30

<210> SEQ ID NO 39
<211> LENGTH: 30
<212> TYPE: DNA
<213> ORGANISM: Human papillomavirus

<400> SEQUENCE: 39
gctaccaaca ccgaatcaga atataaacct                              30

<210> SEQ ID NO 40
<211> LENGTH: 30
<212> TYPE: DNA
```

<213> ORGANISM: Human papillomavirus

<400> SEQUENCE: 40
tgcaactact aatccagttc catctatata                                              30

<210> SEQ ID NO 41
<211> LENGTH: 30
<212> TYPE: DNA
<213> ORGANISM: Human papillomavirus

<400> SEQUENCE: 41
taattttact attagtgccg ctacccagaa                                              30

<210> SEQ ID NO 42
<211> LENGTH: 30
<212> TYPE: DNA
<213> ORGANISM: Human papillomavirus

<400> SEQUENCE: 42
caattttact attagtgctg ccactcaaac                                              30

<210> SEQ ID NO 43
<211> LENGTH: 24
<212> TYPE: DNA
<213> ORGANISM: Human papillomavirus

<400> SEQUENCE: 43
gcttcccagt ctggcacaga atac                                                    24

<210> SEQ ID NO 44
<211> LENGTH: 30
<212> TYPE: DNA
<213> ORGANISM: Human papillomavirus

<400> SEQUENCE: 44
caccaatatg actatttgtg ccacacaaac                                              30

<210> SEQ ID NO 45
<211> LENGTH: 30
<212> TYPE: DNA
<213> ORGANISM: Human papillomavirus

<400> SEQUENCE: 45
taacttaacc ttgtgtgcat ccactgagtc                                              30

<210> SEQ ID NO 46
<211> LENGTH: 30
<212> TYPE: DNA
<213> ORGANISM: Human papillomavirus

<400> SEQUENCE: 46
tctacacaaa atggcgtagc taccacatat                                              30

<210> SEQ ID NO 47
<211> LENGTH: 20
<212> TYPE: DNA
<213> ORGANISM: Human papillomavirus type 6

<400> SEQUENCE: 47
accacacgca gtaccaacat                                                         20

<210> SEQ ID NO 48
<211> LENGTH: 20

```
<212> TYPE: DNA
<213> ORGANISM: Human papillomavirus type 6

<400> SEQUENCE: 48
catgcgtcat gtggaagagt                                          20

<210> SEQ ID NO 49
<211> LENGTH: 20
<212> TYPE: DNA
<213> ORGANISM: Human papillomavirus type 11

<400> SEQUENCE: 49
atgcgccatg tggaggagtt                                          20

<210> SEQ ID NO 50
<211> LENGTH: 20
<212> TYPE: DNA
<213> ORGANISM: Human papillomavirus type 11

<400> SEQUENCE: 50
tggtagatac cacacgcagt                                          20

<210> SEQ ID NO 51
<211> LENGTH: 20
<212> TYPE: DNA
<213> ORGANISM: Human papillomavirus type 13

<400> SEQUENCE: 51
tgactgtgtg tgcagccact                                          20

<210> SEQ ID NO 52
<211> LENGTH: 20
<212> TYPE: DNA
<213> ORGANISM: Human papillomavirus type 13

<400> SEQUENCE: 52
gttgatacta cacgcagtac                                          20

<210> SEQ ID NO 53
<211> LENGTH: 20
<212> TYPE: DNA
<213> ORGANISM: Human papillomavirus type 16

<400> SEQUENCE: 53
acctacgaca tggggaggaa                                          20

<210> SEQ ID NO 54
<211> LENGTH: 20
<212> TYPE: DNA
<213> ORGANISM: Human papillomavirus type 16

<400> SEQUENCE: 54
atgtcattat gtgctgccat                                          20

<210> SEQ ID NO 55
<211> LENGTH: 20
<212> TYPE: DNA
<213> ORGANISM: Human papillomavirus type 18

<400> SEQUENCE: 55
cagtctcctg tacctgggca                                          20

<210> SEQ ID NO 56
```

-continued

```
<211> LENGTH: 20
<212> TYPE: DNA
<213> ORGANISM: Human papillomavirus type 18

<400> SEQUENCE: 56
agataccact cccagtacca                                               20

<210> SEQ ID NO 57
<211> LENGTH: 20
<212> TYPE: DNA
<213> ORGANISM: Human papillomavirus type 26

<400> SEQUENCE: 57
cctgtgttga taccacccgc                                               20

<210> SEQ ID NO 58
<211> LENGTH: 20
<212> TYPE: DNA
<213> ORGANISM: Human papillomavirus type 26

<400> SEQUENCE: 58
cagcatctgc atccactcca                                               20

<210> SEQ ID NO 59
<211> LENGTH: 20
<212> TYPE: DNA
<213> ORGANISM: Human papillomavirus type 30

<400> SEQUENCE: 59
tggacaccac taggaacaca                                               20

<210> SEQ ID NO 60
<211> LENGTH: 20
<212> TYPE: DNA
<213> ORGANISM: Human papillomavirus type 30

<400> SEQUENCE: 60
atctgcaacc acacaaacgt                                               20

<210> SEQ ID NO 61
<211> LENGTH: 20
<212> TYPE: DNA
<213> ORGANISM: Human papillomavirus type 31

<400> SEQUENCE: 61
tgtctgtttg tgctgcaatt                                               20

<210> SEQ ID NO 62
<211> LENGTH: 20
<212> TYPE: DNA
<213> ORGANISM: Human papillomavirus type 31

<400> SEQUENCE: 62
agataccaca cgtagtacca                                               20

<210> SEQ ID NO 63
<211> LENGTH: 20
<212> TYPE: DNA
<213> ORGANISM: Human papillomavirus type 32

<400> SEQUENCE: 63
atctacgcca tgcagaggaa                                               20
```

```
<210> SEQ ID NO 64
<211> LENGTH: 20
<212> TYPE: DNA
<213> ORGANISM: Human papillomavirus type 32

<400> SEQUENCE: 64
actgttgtgg atactacccg                                               20

<210> SEQ ID NO 65
<211> LENGTH: 20
<212> TYPE: DNA
<213> ORGANISM: Human papillomavirus type 33

<400> SEQUENCE: 65
tggtagatac cactcgcagt                                               20

<210> SEQ ID NO 66
<211> LENGTH: 20
<212> TYPE: DNA
<213> ORGANISM: Human papillomavirus type 33

<400> SEQUENCE: 66
gcacacaagt aactagtgac                                               20

<210> SEQ ID NO 67
<211> LENGTH: 20
<212> TYPE: DNA
<213> ORGANISM: Human papillomavirus type 34

<400> SEQUENCE: 67
ccacaagtac aactgcacca                                               20

<210> SEQ ID NO 68
<211> LENGTH: 20
<212> TYPE: DNA
<213> ORGANISM: Human papillomavirus type 34

<400> SEQUENCE: 68
acctcagaca tgcagaagag                                               20

<210> SEQ ID NO 69
<211> LENGTH: 20
<212> TYPE: DNA
<213> ORGANISM: Human papillomavirus type 35

<400> SEQUENCE: 69
tgtctgtgtg ttctgctgtg                                               20

<210> SEQ ID NO 70
<211> LENGTH: 20
<212> TYPE: DNA
<213> ORGANISM: Human papillomavirus type 35

<400> SEQUENCE: 70
aggcatggtg aagaatatga                                               20

<210> SEQ ID NO 71
<211> LENGTH: 20
<212> TYPE: DNA
<213> ORGANISM: Human papillomavirus type 39

<400> SEQUENCE: 71
actgttgtgg acactacccg                                               20
```

<210> SEQ ID NO 72
<211> LENGTH: 20
<212> TYPE: DNA
<213> ORGANISM: Human papillomavirus type 39

<400> SEQUENCE: 72
taccaggcac gtggaggagt                                              20

<210> SEQ ID NO 73
<211> LENGTH: 20
<212> TYPE: DNA
<213> ORGANISM: Human papillomavirus type 40

<400> SEQUENCE: 73
atgtgctgcc acacagtccc                                              20

<210> SEQ ID NO 74
<211> LENGTH: 20
<212> TYPE: DNA
<213> ORGANISM: Human papillomavirus type 40

<400> SEQUENCE: 74
tttgcgtcat ggggaggagt                                              20

<210> SEQ ID NO 75
<211> LENGTH: 20
<212> TYPE: DNA
<213> ORGANISM: Human papillomavirus type 42

<400> SEQUENCE: 75
gccactgcaa catctggtga                                              20

<210> SEQ ID NO 76
<211> LENGTH: 20
<212> TYPE: DNA
<213> ORGANISM: Human papillomavirus type 42

<400> SEQUENCE: 76
actgtggttg atactacccg                                              20

<210> SEQ ID NO 77
<211> LENGTH: 20
<212> TYPE: DNA
<213> ORGANISM: Human papillomavirus type 44

<400> SEQUENCE: 77
gtgctgccac tacacagtcc                                              20

<210> SEQ ID NO 78
<211> LENGTH: 20
<212> TYPE: DNA
<213> ORGANISM: Human papillomavirus type 44

<400> SEQUENCE: 78
catgcgacat gttgaggagt                                              20

<210> SEQ ID NO 79
<211> LENGTH: 20
<212> TYPE: DNA
<213> ORGANISM: Human papillomavirus type 45

<400> SEQUENCE: 79
gtggacacta cccgcagtac                                              20

```
<210> SEQ ID NO 80
<211> LENGTH: 20
<212> TYPE: DNA
<213> ORGANISM: Human papillomavirus type 45

<400> SEQUENCE: 80
gtgccaagta catatgaccc                                              20

<210> SEQ ID NO 81
<211> LENGTH: 20
<212> TYPE: DNA
<213> ORGANISM: Human papillomavirus type 47

<400> SEQUENCE: 81
ttactctcag gcagggggaca                                             20

<210> SEQ ID NO 82
<211> LENGTH: 20
<212> TYPE: DNA
<213> ORGANISM: Human papillomavirus type 47

<400> SEQUENCE: 82
gtcacagttg tagacaacac                                              20

<210> SEQ ID NO 83
<211> LENGTH: 20
<212> TYPE: DNA
<213> ORGANISM: Human papillomavirus type 51

<400> SEQUENCE: 83
gcactgccac tgctgcggtt                                              20

<210> SEQ ID NO 84
<211> LENGTH: 20
<212> TYPE: DNA
<213> ORGANISM: Human papillomavirus type 51

<400> SEQUENCE: 84
aggcatgggg aagagtatga                                              20

<210> SEQ ID NO 85
<211> LENGTH: 20
<212> TYPE: DNA
<213> ORGANISM: Human papillomavirus type 52

<400> SEQUENCE: 85
accttcgtca tggcgaggaa                                              20

<210> SEQ ID NO 86
<211> LENGTH: 20
<212> TYPE: DNA
<213> ORGANISM: Human papillomavirus type 52

<400> SEQUENCE: 86
tggataccac tcgtagcact                                              20

<210> SEQ ID NO 87
<211> LENGTH: 20
<212> TYPE: DNA
<213> ORGANISM: Human papillomavirus type 53

<400> SEQUENCE: 87
```
actctttccg caaccacaca 20

<210> SEQ ID NO 88
<211> LENGTH: 20
<212> TYPE: DNA
<213> ORGANISM: Human papillomavirus type 53

<400> SEQUENCE: 88
tgttgtggat accaccagga 20

<210> SEQ ID NO 89
<211> LENGTH: 20
<212> TYPE: DNA
<213> ORGANISM: Human papillomavirus type 54

<400> SEQUENCE: 89
gctacagcat ccacgcagga 20

<210> SEQ ID NO 90
<211> LENGTH: 20
<212> TYPE: DNA
<213> ORGANISM: Human papillomavirus type 54

<400> SEQUENCE: 90
cagttgtaga taccacccgt 20

<210> SEQ ID NO 91
<211> LENGTH: 20
<212> TYPE: DNA
<213> ORGANISM: Human papillomavirus type 56

<400> SEQUENCE: 91
accttagaca tgtggaggaa 20

<210> SEQ ID NO 92
<211> LENGTH: 20
<212> TYPE: DNA
<213> ORGANISM: Human papillomavirus type 56

<400> SEQUENCE: 92
ctgctacaga acagttaagt 20

<210> SEQ ID NO 93
<211> LENGTH: 20
<212> TYPE: DNA
<213> ORGANISM: Human papillomavirus type 58

<400> SEQUENCE: 93
ggttgatacc actcgtagca 20

<210> SEQ ID NO 94
<211> LENGTH: 20
<212> TYPE: DNA
<213> ORGANISM: Human papillomavirus type 58

<400> SEQUENCE: 94
tgcactgaag taactaagga 20

<210> SEQ ID NO 95
<211> LENGTH: 20
<212> TYPE: DNA
<213> ORGANISM: Human papillomavirus type 59

<400> SEQUENCE: 95

-continued

```
actactcgca gcaccaatct                                               20

<210> SEQ ID NO 96
<211> LENGTH: 20
<212> TYPE: DNA
<213> ORGANISM: Human papillomavirus type 59

<400> SEQUENCE: 96
atgccagaca tgtggaggaa                                               20

<210> SEQ ID NO 97
<211> LENGTH: 20
<212> TYPE: DNA
<213> ORGANISM: Human papillomavirus type 61

<400> SEQUENCE: 97
ccgttgtgga taccacccgc                                               20

<210> SEQ ID NO 98
<211> LENGTH: 20
<212> TYPE: DNA
<213> ORGANISM: Human papillomavirus type 61

<400> SEQUENCE: 98
ttgcgccata cagaggagtt                                               20

<210> SEQ ID NO 99
<211> LENGTH: 20
<212> TYPE: DNA
<213> ORGANISM: Human papillomavirus type 62

<400> SEQUENCE: 99
tgtaccgcct ccactgctgc                                               20

<210> SEQ ID NO 100
<211> LENGTH: 20
<212> TYPE: DNA
<213> ORGANISM: Human papillomavirus type 62

<400> SEQUENCE: 100
tttgcgacac acggaggaat                                               20

<210> SEQ ID NO 101
<211> LENGTH: 20
<212> TYPE: DNA
<213> ORGANISM: Human papillomavirus type 66

<400> SEQUENCE: 101
accttcgcca tgtggaggaa                                               20

<210> SEQ ID NO 102
<211> LENGTH: 20
<212> TYPE: DNA
<213> ORGANISM: Human papillomavirus type 66

<400> SEQUENCE: 102
accagaagca ccaacatgac                                               20

<210> SEQ ID NO 103
<211> LENGTH: 20
<212> TYPE: DNA
<213> ORGANISM: Human papillomavirus type 67
```

```
<400> SEQUENCE: 103
acacgtagta ccaacatgac                                              20

<210> SEQ ID NO 104
<211> LENGTH: 20
<212> TYPE: DNA
<213> ORGANISM: Human papillomavirus type 67

<400> SEQUENCE: 104
accttagaca tgtggaagaa                                              20

<210> SEQ ID NO 105
<211> LENGTH: 20
<212> TYPE: DNA
<213> ORGANISM: Human papillomavirus type 68

<400> SEQUENCE: 105
ttgtggatac aacgcgcagt                                              20

<210> SEQ ID NO 106
<211> LENGTH: 20
<212> TYPE: DNA
<213> ORGANISM: Human papillomavirus type 68

<400> SEQUENCE: 106
cagactctac tgtaccagct                                              20

<210> SEQ ID NO 107
<211> LENGTH: 20
<212> TYPE: DNA
<213> ORGANISM: Human papillomavirus type 69

<400> SEQUENCE: 107
acccgcagta ccaacctcac                                              20

<210> SEQ ID NO 108
<211> LENGTH: 20
<212> TYPE: DNA
<213> ORGANISM: Human papillomavirus type 69

<400> SEQUENCE: 108
gcacaatctg catctgccac                                              20

<210> SEQ ID NO 109
<211> LENGTH: 20
<212> TYPE: DNA
<213> ORGANISM: Human papillomavirus type 70

<400> SEQUENCE: 109
tctgcctgca ccgaaacggc                                              20

<210> SEQ ID NO 110
<211> LENGTH: 20
<212> TYPE: DNA
<213> ORGANISM: Human papillomavirus type 70

<400> SEQUENCE: 110
actgtggtgg acactacacg                                              20

<210> SEQ ID NO 111
<211> LENGTH: 20
<212> TYPE: DNA
<213> ORGANISM: Human papillomavirus
```

```
<400> SEQUENCE: 111
atgtccatct gtgctaccaa                                                     20

<210> SEQ ID NO 112
<211> LENGTH: 20
<212> TYPE: DNA
<213> ORGANISM: Human papillomavirus

<400> SEQUENCE: 112
acagttgtga cacatcacgt                                                     20

<210> SEQ ID NO 113
<211> LENGTH: 20
<212> TYPE: DNA
<213> ORGANISM: Human papillomavirus type 72

<400> SEQUENCE: 113
actgccacag cgtcctctgt                                                     20

<210> SEQ ID NO 114
<211> LENGTH: 20
<212> TYPE: DNA
<213> ORGANISM: Human papillomavirus type 72

<400> SEQUENCE: 114
atcttcgcca cactgaggaa                                                     20

<210> SEQ ID NO 115
<211> LENGTH: 20
<212> TYPE: DNA
<213> ORGANISM: Human papillomavirus type 73

<400> SEQUENCE: 115
ggtacacagg ctagtagctc                                                     20

<210> SEQ ID NO 116
<211> LENGTH: 20
<212> TYPE: DNA
<213> ORGANISM: Human papillomavirus type 73

<400> SEQUENCE: 116
ctacaacgta tgccaactct                                                     20

<210> SEQ ID NO 117
<211> LENGTH: 20
<212> TYPE: DNA
<213> ORGANISM: Human papillomavirus type 74

<400> SEQUENCE: 117
acctcacaat cgccttctgc                                                     20

<210> SEQ ID NO 118
<211> LENGTH: 20
<212> TYPE: DNA
<213> ORGANISM: Human papillomavirus type 74

<400> SEQUENCE: 118
tggataccac acgcagtact                                                     20

<210> SEQ ID NO 119
<211> LENGTH: 20
<212> TYPE: DNA
```

<213> ORGANISM: Human papillomavirus

<400> SEQUENCE: 119
gcactgctgt tactccatct					20

<210> SEQ ID NO 120
<211> LENGTH: 20
<212> TYPE: DNA
<213> ORGANISM: Human papillomavirus

<400> SEQUENCE: 120
agcagtacat taggcatggg					20

<210> SEQ ID NO 121
<211> LENGTH: 20
<212> TYPE: DNA
<213> ORGANISM: Human papillomavirus

<400> SEQUENCE: 121
gcactgctgc tactccatca					20

<210> SEQ ID NO 122
<211> LENGTH: 20
<212> TYPE: DNA
<213> ORGANISM: Human papillomavirus

<400> SEQUENCE: 122
gcacagacat tcactccaac					20

<210> SEQ ID NO 123
<211> LENGTH: 20
<212> TYPE: DNA
<213> ORGANISM: Human papillomavirus

<400> SEQUENCE: 123
gctgctgcta cacaggctaa					20

<210> SEQ ID NO 124
<211> LENGTH: 20
<212> TYPE: DNA
<213> ORGANISM: Human papillomavirus

<400> SEQUENCE: 124
acctccgcca cacagaggaa					20

<210> SEQ ID NO 125
<211> LENGTH: 20
<212> TYPE: DNA
<213> ORGANISM: Human papillomavirus

<400> SEQUENCE: 125
agataccacc cgcagcacca					20

<210> SEQ ID NO 126
<211> LENGTH: 20
<212> TYPE: DNA
<213> ORGANISM: Human papillomavirus

<400> SEQUENCE: 126
agtgctgcta ccaacaccga					20

<210> SEQ ID NO 127
<211> LENGTH: 20

```
<212> TYPE: DNA
<213> ORGANISM: Human papillomavirus

<400> SEQUENCE: 127
acacacgcca tgtagaggaa                                               20

<210> SEQ ID NO 128
<211> LENGTH: 20
<212> TYPE: DNA
<213> ORGANISM: Human papillomavirus

<400> SEQUENCE: 128
actgtggtag acacaacacg                                               20

<210> SEQ ID NO 129
<211> LENGTH: 20
<212> TYPE: DNA
<213> ORGANISM: Human papillomavirus

<400> SEQUENCE: 129
agtgccgcta cccagaaggc                                               20

<210> SEQ ID NO 130
<211> LENGTH: 20
<212> TYPE: DNA
<213> ORGANISM: Human papillomavirus

<400> SEQUENCE: 130
tcgacaccac ccgcagtact                                               20

<210> SEQ ID NO 131
<211> LENGTH: 20
<212> TYPE: DNA
<213> ORGANISM: Human papillomavirus

<400> SEQUENCE: 131
tgctgccact caaacaacca                                               20

<210> SEQ ID NO 132
<211> LENGTH: 20
<212> TYPE: DNA
<213> ORGANISM: Human papillomavirus

<400> SEQUENCE: 132
cggttgttga tactactcgc                                               20

<210> SEQ ID NO 133
<211> LENGTH: 20
<212> TYPE: DNA
<213> ORGANISM: Human papillomavirus

<400> SEQUENCE: 133
gtgctgcttc ccagtctggc                                               20

<210> SEQ ID NO 134
<211> LENGTH: 20
<212> TYPE: DNA
<213> ORGANISM: Human papillomavirus

<400> SEQUENCE: 134
accacccgta gtaccaacct                                               20

<210> SEQ ID NO 135
```

```
<210> SEQ ID NO 135
<211> LENGTH: 20
<212> TYPE: DNA
<213> ORGANISM: Human papillomavirus

<400> SEQUENCE: 135
tgtggataca actcgcagca                                              20

<210> SEQ ID NO 136
<211> LENGTH: 20
<212> TYPE: DNA
<213> ORGANISM: Human papillomavirus

<400> SEQUENCE: 136
gcatccactg agtctgtgct                                              20

<210> SEQ ID NO 137
<211> LENGTH: 30
<212> TYPE: DNA
<213> ORGANISM: Human papillomavirus type 6

<400> SEQUENCE: 137
actacacgca gtaccaacat gacattatgt                                   30

<210> SEQ ID NO 138
<211> LENGTH: 30
<212> TYPE: DNA
<213> ORGANISM: Human papillomavirus type 6

<400> SEQUENCE: 138
cgtaactaca tcttccacat acaccaattc                                   30

<210> SEQ ID NO 139
<211> LENGTH: 30
<212> TYPE: DNA
<213> ORGANISM: Human papillomavirus type 6

<400> SEQUENCE: 139
caacatgaca ttatgtgcat ccgtaactac                                   30

<210> SEQ ID NO 140
<211> LENGTH: 33
<212> TYPE: DNA
<213> ORGANISM: Human papillomavirus type 6

<400> SEQUENCE: 140
catgacatta tgtgcatccg taactacatc ttc                               33

<210> SEQ ID NO 141
<211> LENGTH: 30
<212> TYPE: DNA
<213> ORGANISM: Human papillomavirus type 6

<400> SEQUENCE: 141
tccgtaacta catcttccac atacaccaat                                   30

<210> SEQ ID NO 142
<211> LENGTH: 30
<212> TYPE: DNA
<213> ORGANISM: Human papillomavirus type 13

<400> SEQUENCE: 142
agccactaca tcatctcttt cagacacata                                   30
```

<210> SEQ ID NO 143
<211> LENGTH: 30
<212> TYPE: DNA
<213> ORGANISM: Human papillomavirus type 13

<400> SEQUENCE: 143
taacatgact gtgtgtgcag ccactacatc                                   30

<210> SEQ ID NO 144
<211> LENGTH: 30
<212> TYPE: DNA
<213> ORGANISM: Human papillomavirus type 16

<400> SEQUENCE: 144
gccatatcta cttcagaaac tacatataaa                                   30

<210> SEQ ID NO 145
<211> LENGTH: 30
<212> TYPE: DNA
<213> ORGANISM: Human papillomavirus type 16

<400> SEQUENCE: 145
atgtcattat gtgctgccat atctacttca                                   30

<210> SEQ ID NO 146
<211> LENGTH: 30
<212> TYPE: DNA
<213> ORGANISM: Human papillomavirus type 16

<400> SEQUENCE: 146
gtcattatgt gctgccatat ctacttcaga                                   30

<210> SEQ ID NO 147
<211> LENGTH: 30
<212> TYPE: DNA
<213> ORGANISM: Human papillomavirus type 16

<400> SEQUENCE: 147
gccatatcta cttcagaaac tacatataaa                                   30

<210> SEQ ID NO 148
<211> LENGTH: 30
<212> TYPE: DNA
<213> ORGANISM: Human papillomavirus type 18

<400> SEQUENCE: 148
aacaatatgt gcttctacac agtctcctgt                                   30

<210> SEQ ID NO 149
<211> LENGTH: 30
<212> TYPE: DNA
<213> ORGANISM: Human papillomavirus type 18

<400> SEQUENCE: 149
tcctgtacct gggcaatatg atgctaccaa                                   30

<210> SEQ ID NO 150
<211> LENGTH: 30
<212> TYPE: DNA
<213> ORGANISM: Human papillomavirus type 18

<400> SEQUENCE: 150
tatgtgcttc tacacagtct cctgtacctg                                   30

```
<210> SEQ ID NO 151
<211> LENGTH: 30
<212> TYPE: DNA
<213> ORGANISM: Human papillomavirus type 26

<400> SEQUENCE: 151
aaccttacca ttagtacatt atctgcagca                                      30

<210> SEQ ID NO 152
<211> LENGTH: 30
<212> TYPE: DNA
<213> ORGANISM: Human papillomavirus type 26

<400> SEQUENCE: 152
acattatctg cagcatctgc atccactcca                                      30

<210> SEQ ID NO 153
<211> LENGTH: 30
<212> TYPE: DNA
<213> ORGANISM: Human papillomavirus type 30

<400> SEQUENCE: 153
ccacacaaac gttatccaca tataattcaa                                      30

<210> SEQ ID NO 154
<211> LENGTH: 30
<212> TYPE: DNA
<213> ORGANISM: Human papillomavirus type 30

<400> SEQUENCE: 154
gactatatct gcaaccacac aaacgttatc                                      30

<210> SEQ ID NO 155
<211> LENGTH: 30
<212> TYPE: DNA
<213> ORGANISM: Human papillomavirus type 30

<400> SEQUENCE: 155
atctgcaacc acacaaacgt tatccacata                                      30

<210> SEQ ID NO 156
<211> LENGTH: 30
<212> TYPE: DNA
<213> ORGANISM: Human papillomavirus type 31

<400> SEQUENCE: 156
aagtagtaat tttaaagagt atttaagaca                                      30

<210> SEQ ID NO 157
<211> LENGTH: 30
<212> TYPE: DNA
<213> ORGANISM: Human papillomavirus type 31

<400> SEQUENCE: 157
atgtctgttt gtgctgcaat tgcaaacagt                                      30

<210> SEQ ID NO 158
<211> LENGTH: 30
<212> TYPE: DNA
<213> ORGANISM: Human papillomavirus type 31

<400> SEQUENCE: 158
aacagtgata ctacatttaa aagtagtaat                                      30
```

```
<210> SEQ ID NO 159
<211> LENGTH: 30
<212> TYPE: DNA
<213> ORGANISM: Human papillomavirus type 31

<400> SEQUENCE: 159
tctgtttgtg ctgcaattgc aaacagtgat                              30

<210> SEQ ID NO 160
<211> LENGTH: 30
<212> TYPE: DNA
<213> ORGANISM: Human papillomavirus type 31

<400> SEQUENCE: 160
gcaattgcaa acagtgatac tacatttaaa                              30

<210> SEQ ID NO 161
<211> LENGTH: 30
<212> TYPE: DNA
<213> ORGANISM: Human papillomavirus type 32

<400> SEQUENCE: 161
caccaacacc atatgacaat agtaagttta                              30

<210> SEQ ID NO 162
<211> LENGTH: 30
<212> TYPE: DNA
<213> ORGANISM: Human papillomavirus type 33

<400> SEQUENCE: 162
tagtgacagt acatataaaa atgaaaattt                              30

<210> SEQ ID NO 163
<211> LENGTH: 30
<212> TYPE: DNA
<213> ORGANISM: Human papillomavirus type 33

<400> SEQUENCE: 163
gcacacaagt aactagtgac agtacatata                              30

<210> SEQ ID NO 164
<211> LENGTH: 30
<212> TYPE: DNA
<213> ORGANISM: Human papillomavirus type 33

<400> SEQUENCE: 164
gtgacagtac atataaaaat gaaaatttta                              30

<210> SEQ ID NO 165
<211> LENGTH: 30
<212> TYPE: DNA
<213> ORGANISM: Human papillomavirus type 34

<400> SEQUENCE: 165
taggtacaca atccacaagt acaactgcac                              30

<210> SEQ ID NO 166
<211> LENGTH: 30
<212> TYPE: DNA
<213> ORGANISM: Human papillomavirus type 35

<400> SEQUENCE: 166
```
tgtctgtgtg ttctgctgtg tcttctagtg                                30

<210> SEQ ID NO 167
<211> LENGTH: 30
<212> TYPE: DNA
<213> ORGANISM: Human papillomavirus type 35

<400> SEQUENCE: 167
gtgtcttcta gtgacagtac atataaaaat                                30

<210> SEQ ID NO 168
<211> LENGTH: 30
<212> TYPE: DNA
<213> ORGANISM: Human papillomavirus type 35

<400> SEQUENCE: 168
aacccgtagt acaaatatgt ctgtgtgttc                                30

<210> SEQ ID NO 169
<211> LENGTH: 30
<212> TYPE: DNA
<213> ORGANISM: Human papillomavirus type 35

<400> SEQUENCE: 169
tctgctgtgt cttctagtga cagtacaata                                30

<210> SEQ ID NO 170
<211> LENGTH: 30
<212> TYPE: DNA
<213> ORGANISM: Human papillomavirus type 39

<400> SEQUENCE: 170
ctttacatta tctacctcta tagagtcttc                                30

<210> SEQ ID NO 171
<211> LENGTH: 30
<212> TYPE: DNA
<213> ORGANISM: Human papillomavirus type 39

<400> SEQUENCE: 171
agagtcttcc ataccttcta catatgatcc                                30

<210> SEQ ID NO 172
<211> LENGTH: 30
<212> TYPE: DNA
<213> ORGANISM: Human papillomavirus type 39

<400> SEQUENCE: 172
ccgtagtacc aactttacat tatctacctc                                30

<210> SEQ ID NO 173
<211> LENGTH: 30
<212> TYPE: DNA
<213> ORGANISM: Human papillomavirus type 39

<400> SEQUENCE: 173
caactttaca ttatctacct ctatagagtc                                30

<210> SEQ ID NO 174
<211> LENGTH: 30
<212> TYPE: DNA
<213> ORGANISM: Human papillomavirus type 39

<400> SEQUENCE: 174

```
ctacctctat agagtcttcc atacctttct                                            30
```

```
<210> SEQ ID NO 175
<211> LENGTH: 30
<212> TYPE: DNA
<213> ORGANISM: Human papillomavirus type 40

<400> SEQUENCE: 175
gtcccccaca ccaaccccat ataataacag                                            30

<210> SEQ ID NO 176
<211> LENGTH: 30
<212> TYPE: DNA
<213> ORGANISM: Human papillomavirus type 40

<400> SEQUENCE: 176
accccatata ataacagtaa tttcaaggaa                                            30

<210> SEQ ID NO 177
<211> LENGTH: 30
<212> TYPE: DNA
<213> ORGANISM: Human papillomavirus type 40

<400> SEQUENCE: 177
acagtccccc acaccaaccc catataataa                                            30

<210> SEQ ID NO 178
<211> LENGTH: 30
<212> TYPE: DNA
<213> ORGANISM: Human papillomavirus type 42

<400> SEQUENCE: 178
acatctggtg atacatatac agctgctaat                                            30

<210> SEQ ID NO 179
<211> LENGTH: 30
<212> TYPE: DNA
<213> ORGANISM: Human papillomavirus type 42

<400> SEQUENCE: 179
cactgcaaca tctggtgata catatacagc                                            30

<210> SEQ ID NO 180
<211> LENGTH: 30
<212> TYPE: DNA
<213> ORGANISM: Human papillomavirus type 43

<400> SEQUENCE: 180
tgaccctact gtgcccagta catatgacaa                                            30

<210> SEQ ID NO 181
<211> LENGTH: 27
<212> TYPE: DNA
<213> ORGANISM: Human papillomavirus type 43

<400> SEQUENCE: 181
tgcaaagttt aaggaatacc tgcggca                                               27

<210> SEQ ID NO 182
<211> LENGTH: 30
<212> TYPE: DNA
<213> ORGANISM: Human papillomavirus type 44
```

```
<400> SEQUENCE: 182
gccactacac agtccctcc gtctacatat                                    30

<210> SEQ ID NO 183
<211> LENGTH: 30
<212> TYPE: DNA
<213> ORGANISM: Human papillomavirus type 44

<400> SEQUENCE: 183
gacaatatgt gctgccacta cacagtcccc                                   30

<210> SEQ ID NO 184
<211> LENGTH: 30
<212> TYPE: DNA
<213> ORGANISM: Human papillomavirus type 44

<400> SEQUENCE: 184
aatatgtgct gccactacac agtccctcc                                    30

<210> SEQ ID NO 185
<211> LENGTH: 30
<212> TYPE: DNA
<213> ORGANISM: Human papillomavirus type 45

<400> SEQUENCE: 185
taacattatg tgcctctaca caaaatcctg                                   30

<210> SEQ ID NO 186
<211> LENGTH: 30
<212> TYPE: DNA
<213> ORGANISM: Human papillomavirus type 45

<400> SEQUENCE: 186
ctctacacaa aatcctgtgc caagtacata                                   30

<210> SEQ ID NO 187
<211> LENGTH: 30
<212> TYPE: DNA
<213> ORGANISM: Human papillomavirus type 51

<400> SEQUENCE: 187
ttaactatta gcactgccac tgctgcggtt                                   30

<210> SEQ ID NO 188
<211> LENGTH: 30
<212> TYPE: DNA
<213> ORGANISM: Human papillomavirus type 51

<400> SEQUENCE: 188
tttaactatt agcactgcca ctgctgcggt                                   30

<210> SEQ ID NO 189
<211> LENGTH: 30
<212> TYPE: DNA
<213> ORGANISM: Human papillomavirus type 51

<400> SEQUENCE: 189
tagcactgcc actgctgcgg tttccccaac                                   30

<210> SEQ ID NO 190
<211> LENGTH: 30
<212> TYPE: DNA
<213> ORGANISM: Human papillomavirus type 52
```

```
<400> SEQUENCE: 190
cacagttgtg gataccactc gtagcactaa                                30

<210> SEQ ID NO 191
<211> LENGTH: 30
<212> TYPE: DNA
<213> ORGANISM: Human papillomavirus type 52

<400> SEQUENCE: 191
aaaaggaaag cacatataaa aatgaaaatt                                30

<210> SEQ ID NO 192
<211> LENGTH: 30
<212> TYPE: DNA
<213> ORGANISM: Human papillomavirus type 52

<400> SEQUENCE: 192
cactgctagc actaacatga ctttatgtgc                                30

<210> SEQ ID NO 193
<211> LENGTH: 30
<212> TYPE: DNA
<213> ORGANISM: Human papillomavirus type 52

<400> SEQUENCE: 193
catgacttta tgtgctgagg ttaaaaagga                                30

<210> SEQ ID NO 194
<211> LENGTH: 30
<212> TYPE: DNA
<213> ORGANISM: Human papillomavirus type 52

<400> SEQUENCE: 194
agcacatata aaatgaaaaa ttttaaggaa                                30

<210> SEQ ID NO 195
<211> LENGTH: 30
<212> TYPE: DNA
<213> ORGANISM: Human papillomavirus type 52

<400> SEQUENCE: 195
aaaaggaaag cacatataaa aatgaaaatt                                30

<210> SEQ ID NO 196
<211> LENGTH: 30
<212> TYPE: DNA
<213> ORGANISM: Human papillomavirus type 52

<400> SEQUENCE: 196
gaggttaaaa aggaaagcac atataaaaat                                30

<210> SEQ ID NO 197
<211> LENGTH: 30
<212> TYPE: DNA
<213> ORGANISM: Human papillomavirus type 53

<400> SEQUENCE: 197
gatctctttc cgcaaccaca cagtctatgt                                30

<210> SEQ ID NO 198
<211> LENGTH: 30
<212> TYPE: DNA
```

```
<213> ORGANISM: Human papillomavirus type 53

<400> SEQUENCE: 198
ctctttccgc aaccacacag tctatgtcta                                30

<210> SEQ ID NO 199
<211> LENGTH: 30
<212> TYPE: DNA
<213> ORGANISM: Human papillomavirus type 53

<400> SEQUENCE: 199
ctacatataa ttcaaagcaa attaaacagt                                30

<210> SEQ ID NO 200
<211> LENGTH: 30
<212> TYPE: DNA
<213> ORGANISM: Human papillomavirus type 56

<400> SEQUENCE: 200
agttaagtaa atatgatgca cgaaaaatta                                30

<210> SEQ ID NO 201
<211> LENGTH: 30
<212> TYPE: DNA
<213> ORGANISM: Human papillomavirus type 56

<400> SEQUENCE: 201
gtactgctac agaacagtta agtaaatatg                                30

<210> SEQ ID NO 202
<211> LENGTH: 30
<212> TYPE: DNA
<213> ORGANISM: Human papillomavirus type 56

<400> SEQUENCE: 202
tagaagtact aacatgacta ttagtactgc                                30

<210> SEQ ID NO 203
<211> LENGTH: 30
<212> TYPE: DNA
<213> ORGANISM: Human papillomavirus type 58

<400> SEQUENCE: 203
tgcactgaag taactaagga aggtacatat                                30

<210> SEQ ID NO 204
<211> LENGTH: 30
<212> TYPE: DNA
<213> ORGANISM: Human papillomavirus type 58

<400> SEQUENCE: 204
cactaatatg acattatgca ctgaagtaac                                30

<210> SEQ ID NO 205
<211> LENGTH: 30
<212> TYPE: DNA
<213> ORGANISM: Human papillomavirus type 58

<400> SEQUENCE: 205
actaaggaag gtacatataa aaatgataat                                30

<210> SEQ ID NO 206
<211> LENGTH: 30
```

```
<212> TYPE: DNA
<213> ORGANISM: Human papillomavirus type 59

<400> SEQUENCE: 206
actactcgca gcaccaatct ttctgtgtgt                                    30

<210> SEQ ID NO 207
<211> LENGTH: 30
<212> TYPE: DNA
<213> ORGANISM: Human papillomavirus type 61

<400> SEQUENCE: 207
taatttaacc atttgtactg ctacatcccc                                    30

<210> SEQ ID NO 208
<211> LENGTH: 30
<212> TYPE: DNA
<213> ORGANISM: Human papillomavirus type 61

<400> SEQUENCE: 208
aaccatttgt actgctacat ccccccctgt                                    30

<210> SEQ ID NO 209
<211> LENGTH: 30
<212> TYPE: DNA
<213> ORGANISM: Human papillomavirus type 66

<400> SEQUENCE: 209
tgaaatcaat caataccttc gccatgtgga                                    30

<210> SEQ ID NO 210
<211> LENGTH: 30
<212> TYPE: DNA
<213> ORGANISM: Human papillomavirus type 66

<400> SEQUENCE: 210
agctaaaagc acattaacta aatatgatgc                                    30

<210> SEQ ID NO 211
<211> LENGTH: 30
<212> TYPE: DNA
<213> ORGANISM: Human papillomavirus type 66

<400> SEQUENCE: 211
taatgcagct aaaagcacat taactaatat                                    30

<210> SEQ ID NO 212
<211> LENGTH: 30
<212> TYPE: DNA
<213> ORGANISM: Human papillomavirus type 66

<400> SEQUENCE: 212
ttaactaaat atgatgcccg tgaaatcaat                                    30

<210> SEQ ID NO 213
<211> LENGTH: 30
<212> TYPE: DNA
<213> ORGANISM: Human papillomavirus type 66

<400> SEQUENCE: 213
taatgcagct aaaagcacat taactacata                                    30

<210> SEQ ID NO 214
```

```
<210> SEQ ID NO 214
<211> LENGTH: 30
<212> TYPE: DNA
<213> ORGANISM: Human papillomavirus type 67

<400> SEQUENCE: 214
aaaaatcaga ggctacatac aaaaatgaaa                                30

<210> SEQ ID NO 215
<211> LENGTH: 30
<212> TYPE: DNA
<213> ORGANISM: Human papillomavirus type 72

<400> SEQUENCE: 215
cacagcgtcc tctgtatcag aatattacag                                30

<210> SEQ ID NO 216
<211> LENGTH: 30
<212> TYPE: DNA
<213> ORGANISM: Human papillomavirus type 74

<400> SEQUENCE: 216
ctcacaatcg ccttctgcta catataatag                                30

<210> SEQ ID NO 217
<211> LENGTH: 30
<212> TYPE: DNA
<213> ORGANISM: Human papillomavirus

<400> SEQUENCE: 217
cacagctaca tctgctgctg cagaatacaa                                30

<210> SEQ ID NO 218
<211> LENGTH: 30
<212> TYPE: DNA
<213> ORGANISM: Human papillomavirus

<400> SEQUENCE: 218
atctgctgct gcagaataca aggcctctaa                                30

<210> SEQ ID NO 219
<211> LENGTH: 27
<212> TYPE: DNA
<213> ORGANISM: Human papillomavirus

<400> SEQUENCE: 219
cccctctaag tttaatgaat atctaag                                   27

<210> SEQ ID NO 220
<211> LENGTH: 30
<212> TYPE: DNA
<213> ORGANISM: Human papillomavirus

<400> SEQUENCE: 220
tctgaatatg acccctcta agtttaatga                                 30

<210> SEQ ID NO 221
<211> LENGTH: 30
<212> TYPE: DNA
<213> ORGANISM: Human papillomavirus

<400> SEQUENCE: 221
cgctacccag aaggcctctg aatatgaccc                                30
```

```
<210> SEQ ID NO 222
<211> LENGTH: 30
<212> TYPE: DNA
<213> ORGANISM: Human papillomavirus

<400> SEQUENCE: 222
tgccactcaa acaaccactg aatatgaccc                                      30

<210> SEQ ID NO 223
<211> LENGTH: 27
<212> TYPE: DNA
<213> ORGANISM: Human papillomavirus

<400> SEQUENCE: 223
cacaaagttt aaggaatatt taaggca                                         27

<210> SEQ ID NO 224
<211> LENGTH: 30
<212> TYPE: DNA
<213> ORGANISM: Human papillomavirus

<400> SEQUENCE: 224
aacaaccact gaatatgacc ccacaaagtt                                      30

<210> SEQ ID NO 225
<211> LENGTH: 30
<212> TYPE: DNA
<213> ORGANISM: Human papillomavirus

<400> SEQUENCE: 225
ccgtagtacc aaccttacca tttgtgctgc                                      30

<210> SEQ ID NO 226
<211> LENGTH: 30
<212> TYPE: DNA
<213> ORGANISM: Human papillomavirus

<400> SEQUENCE: 226
catttgtgct gcttcccagt ctggcacaga                                      30

<210> SEQ ID NO 227
<211> LENGTH: 30
<212> TYPE: DNA
<213> ORGANISM: Human papillomavirus

<400> SEQUENCE: 227
cacacaaaca ccctctgaca catacaaggc                                      30

<210> SEQ ID NO 228
<211> LENGTH: 30
<212> TYPE: DNA
<213> ORGANISM: Human papillomavirus

<400> SEQUENCE: 228
ctacctacta catatgacaa cacaaagttc                                      30

<210> SEQ ID NO 229
<211> LENGTH: 30
<212> TYPE: DNA
<213> ORGANISM: Human papillomavirus

<400> SEQUENCE: 229
atccactgag tctgtgctac ctactacata                                      30
```

```
<210> SEQ ID NO 230
<211> LENGTH: 30
<212> TYPE: DNA
<213> ORGANISM: Human papillomavirus

<400> SEQUENCE: 230
tttaacactg tgtgcttcta cacaaaatgg                                       30

<210> SEQ ID NO 231
<211> LENGTH: 138
<212> TYPE: DNA
<213> ORGANISM: Human papillomavirus type 6

<400> SEQUENCE: 231
tttgttactg tggtagatac cacacgcagt accaacatga cattatgtgc atccgtaact      60
acatcttcca catacaccaa ttctgattat aaagagtaca tgcgtcatgt ggaagagtat     120
gatttacaat ttattttt                                                   138

<210> SEQ ID NO 232
<211> LENGTH: 136
<212> TYPE: DNA
<213> ORGANISM: Human papillomavirus type 11

<400> SEQUENCE: 232
tttgttactg tggtagatac cacacgcagt acaaatatga cactatgtgc atctgtctaa      60
atctgctaca tacactaatt cagattataa ggaatacatg cgccatgtgg aggagtttga     120
tttacagttt attttt                                                     136

<210> SEQ ID NO 233
<211> LENGTH: 144
<212> TYPE: DNA
<213> ORGANISM: Human papillomavirus type 13

<400> SEQUENCE: 233
tttgttactg tagttgatac tacacgcagt actaacatga ctgtgtgtgc agccactaca      60
tcatctcttt cagacacata taaggccaca gaatataaac agtacatgcg acatgtagaa     120
gaatttgatt tacaatttat tttt                                            144

<210> SEQ ID NO 234
<211> LENGTH: 141
<212> TYPE: DNA
<213> ORGANISM: Human papillomavirus type 16

<400> SEQUENCE: 234
tttgttactg ttgttgatac tacacgcagt acaaatatgt cattatgtgc tgccatatct      60
acttcagaaa ctacatataa aaatactaac tttaaggagt acctacgaca tgggaggaa      120 tatgatttac agtttatttt t                                               141

<210> SEQ ID NO 235
<211> LENGTH: 144
<212> TYPE: DNA
<213> ORGANISM: Human papillomavirus type 18

<400> SEQUENCE: 235
tttgttactg tggtagatac cactcccagt accaatttaa caatatgtgc ttctacacag      60
tctcctgtac ctgggcaata tgatgctacc aaatttaagc agtatagcag acatgttgag     120
gaatatgatt tgcagtttat tttt                                            144
```

```
<210> SEQ ID NO 236
<211> LENGTH: 144
<212> TYPE: DNA
<213> ORGANISM: Human papillomavirus type 26

<400> SEQUENCE: 236
tttgttacct gtgttgatac cacccgcagt actaacctta ccattagtac attatctgca      60
gcatctgcat ccactccatt taaaccatct gattataaac aatttataag acatggcgaa     120
gaatatgaat tacaatttat attt                                            144

<210> SEQ ID NO 237
<211> LENGTH: 137
<212> TYPE: DNA
<213> ORGANISM: Human papillomavirus type 30

<400> SEQUENCE: 237
tttgttactg tgtggacacc actaggaaca caaacatgac tatatctgca accacacaaa      60
cgttatccac atataattca agccaaatta aacagtatgt aagacatgta gaggaatatg     120
aattacagtt tgtgttt                                                    137

<210> SEQ ID NO 238
<211> LENGTH: 141
<212> TYPE: DNA
<213> ORGANISM: Human papillomavirus type 31

<400> SEQUENCE: 238
tttgttactg tggtagatac cacacgtagt accaatatgt ctgtttgtgc tgcaattgca      60
aacagtgata ctacatttaa aagtagtaat tttaaagagt atttaagaca tggtgaggaa     120
tttgatttac aatttatatt t                                               141

<210> SEQ ID NO 239
<211> LENGTH: 138
<212> TYPE: DNA
<213> ORGANISM: Human papillomavirus type 32

<400> SEQUENCE: 239
tttctaactg ttgtggatac tacccgtagt actaacatga ctgtgtgtgc tactgtaaca      60
actgaagaca catacaagtc tactaacttt aaggaatatc tacgccatgc agaggaatat     120
gatatacagt ttatatttt                                                  138

<210> SEQ ID NO 240
<211> LENGTH: 138
<212> TYPE: DNA
<213> ORGANISM: Human papillomavirus type 33

<400> SEQUENCE: 240
tttgttactg tggtagatac cactcgcagt actaatatga ctttatgcac acaagtaact      60
agtgacagta catataaaaa tgaaaatttt aagaatatat aagacatgt tgaagaatat     120 gatctacagt ttgtttttt                                                  138

<210> SEQ ID NO 241
<211> LENGTH: 140
<212> TYPE: DNA
<213> ORGANISM: Human papillomavirus type 35

<400> SEQUENCE: 241
```

```
tttgttactg tagttgatac aacccgtagt acaaatatgt ctgtgtgttc tgctgtgtct    60
tctagtcaca gtacatataa aaatgacaat tttaaggaat atttaggcat ggtgaagaat   120
atgatttaca gtttatttt                                                140

<210> SEQ ID NO 242
<211> LENGTH: 144
<212> TYPE: DNA
<213> ORGANISM: Human papillomavirus type 39

<400> SEQUENCE: 242
tttcttactg ttgtggacac tacccgtagt accaacttta cattatctac ctctatagag    60
tcttccatac cttctacata tgatccttct aagtttaagg aatataccag gcacgtggag   120
gagtatgatt tacaatttat attt                                          144

<210> SEQ ID NO 243
<211> LENGTH: 145
<212> TYPE: DNA
<213> ORGANISM: Human papillomavirus type 40

<400> SEQUENCE: 243
tttgttacag ttgtagacac cactcgtagc actaatttaa ccttatgtgc tgccacacag    60
tcccccacac caaccccata taataacagt aatttcaagg aatatttgcg tcatggggag   120
gagtttgatt tgcagcttta ttttt                                         145

<210> SEQ ID NO 244
<211> LENGTH: 138
<212> TYPE: DNA
<213> ORGANISM: Human papillomavirus type 42

<400> SEQUENCE: 244
tttttaactg tggttgatac tacccgtact actaacatga ctttgtgtgc cactgcaaca    60
tctggtgata catatacagc tgctaatttt aaggaatatt taagacatgc tgaagaatat   120
gatgtgcaat ttatattt                                                 138

<210> SEQ ID NO 245
<211> LENGTH: 143
<212> TYPE: DNA
<213> ORGANISM: Human papillomavirus type 43

<400> SEQUENCE: 245
tttgttacag tggtagatac cactcgtagt acaaacttaa cgttatgtgc ctctactgac    60
cctactgtgc ccagtacata tgacaatgca agtttaagg aataccctgcg gcatgtggag   120 aatatgatct gcagtttata ttt                                           143

<210> SEQ ID NO 246
<211> LENGTH: 144
<212> TYPE: DNA
<213> ORGANISM: Human papillomavirus type 44

<400> SEQUENCE: 246
tttgttactg ttgtagatac tacccgtagt acaaacatga caatatgtgc tgccactaca    60
cactcccctc cgtctacata tactagtgaa caatataagc aatacatgcg acatgttgag   120
gagtttgact tacaatttat gttt                                          144

<210> SEQ ID NO 247
<211> LENGTH: 144
```

```
<212> TYPE: DNA
<213> ORGANISM: Human papillomavirus type 45

<400> SEQUENCE: 247
tttgttactg tagtggacac tacccgcagt actaatttaa cattatgtgc ctctacacaa      60
aatcctgtgc caagtacata tgaccctact aagtttaagc agtatagtag acatgtggag     120
gaatatgatt tacagtttat tttt                                            144

<210> SEQ ID NO 248
<211> LENGTH: 141
<212> TYPE: DNA
<213> ORGANISM: Human papillomavirus type 51

<400> SEQUENCE: 248
tttattacct gtcttgatac taccagaagt acaaatttaa ctattagcac tgccactgct      60
gcggtttccc caacatttac tccaagtaac tttaagcaat atattaggca tggggaagag     120
tatgaattgc aatttatttt t                                               141

<210> SEQ ID NO 249
<211> LENGTH: 138
<212> TYPE: DNA
<213> ORGANISM: Human papillomavirus type 52

<400> SEQUENCE: 249
tttgtcacag ttgtggatac cactcgtagc actaacatga ctttatgtgc tgaggttaaa      60
aaggaaagca catataaaaa tgaaaatttt aaggaatacc ttcgtcatgg cgaggaattt     120
gatttacaat ttattttt                                                   138

<210> SEQ ID NO 250
<211> LENGTH: 138
<212> TYPE: DNA
<213> ORGANISM: Human papillomavirus type 53

<400> SEQUENCE: 250
tttgtaactg ttgtggatac caccaggaat acaaacatga ctctttccgc aaccacacag      60
tctatgtcta catataattc aaagcaaatt aaacagtatg ttagacatgc agaggaatat     120
gaattacaat tgtgtttt                                                   138

<210> SEQ ID NO 251
<211> LENGTH: 137
<212> TYPE: DNA
<213> ORGANISM: Human papillomavirus type 54

<400> SEQUENCE: 251
tttttaacag ttgtagatac cacccgtagt actaacctaa cattgtgtgc tacagcatcc      60
acgcaggata gctttaataa ttctgacttt agggagtata ttagacatgt taggaatatg     120
atttacagtt tatattt                                                    137

<210> SEQ ID NO 252
<211> LENGTH: 138
<212> TYPE: DNA
<213> ORGANISM: Human papillomavirus type 56

<400> SEQUENCE: 252
tttgttactg tagtagatac tactagaagt actaacatga ctattagtac tgctacagaa      60
cagttaagta aatatgatgc acgaaaaatt aatcagtacc ttagacatgt ggaggaatat     120
```

```
<210> SEQ ID NO 253
<211> LENGTH: 138
<212> TYPE: DNA
<213> ORGANISM: Human papillomavirus type 58

<400> SEQUENCE: 253
tttgttaccg tggttgatac cactcgtagc actaatatga cattatgcac tgaagtaact      60
aaggaaggta catataaaaa tgataatttt aaggaatatg tacgtcatgt tgaagaatat     120
gacttacagt tgttttt                                                    138

<210> SEQ ID NO 254
<211> LENGTH: 144
<212> TYPE: DNA
<213> ORGANISM: Human papillomavirus type 59

<400> SEQUENCE: 254
tttttaacag ttgtagatac tactcgcagc accaatcttt ctgtgtgtgc ttctactact      60
tcttctattc ctaatgtata cacacctacc agttttaaag aatatgccag acatgtggag     120
gaatttgatt gcagtttat attt                                             144

<210> SEQ ID NO 255
<211> LENGTH: 141
<212> TYPE: DNA
<213> ORGANISM: Human papillomavirus type 61

<400> SEQUENCE: 255
tttgtaaccg tgtggatac cacccgcagt actaatttaa ccatttgtac tgctacatcc       60 cccctgtat ctgaatataa agccacaagc tttagggaat atttgcgcca tacagaggag      120
tttgatttgc aatttatttt t                                               141

<210> SEQ ID NO 256
<211> LENGTH: 137
<212> TYPE: DNA
<213> ORGANISM: Human papillomavirus type 62

<400> SEQUENCE: 256
tttgttactg tggtggatac taccagaagt actaatttta ctatttgtac cgcctccact      60
gctgcagcag aatacacggc taccaacttt agggattttt gcgacacacg gaggaatttg     120
atttgcaatt tatattt                                                    137

<210> SEQ ID NO 257
<211> LENGTH: 138
<212> TYPE: DNA
<213> ORGANISM: Human papillomavirus type 66

<400> SEQUENCE: 257
tttgttactg ttgtggatac taccagaagc accaacatga ctattaatgc agctaaaagc      60
acattaacta aatatgatgc ccgtgaaatc aatcaatacc ttcgccatgt ggaggaatat     120
gaactacagt tgtgttt                                                    138

<210> SEQ ID NO 258
<211> LENGTH: 138
<212> TYPE: DNA
<213> ORGANISM: Human papillomavirus type 67

<400> SEQUENCE: 258
```

```
tttgttactg tttgtagaca ctacacgtag taccaacatg actttatgtt ctgaggaaaa    60
atcagaggct acatacaaaa atgaaacttt aaggaatacc ttagacatgt ggaagaatat   120
gatttgcagt ttatattt                                                 138

<210> SEQ ID NO 259
<211> LENGTH: 144
<212> TYPE: DNA
<213> ORGANISM: Human papillomavirus type 68

<400> SEQUENCE: 259
tttcttaccg ttgtggatac aacgcgcagt actaattttta cattgtccac tactacagac    60
tctactgtac cagctgtgta tgattctaat aaatttaagg aatatgttag gcatgttgag   120
gaatatgatt tgcagtttat attt                                          144

<210> SEQ ID NO 260
<211> LENGTH: 144
<212> TYPE: DNA
<213> ORGANISM: Human papillomavirus type 69

<400> SEQUENCE: 260
tttgttactt gtgtagatac tacccgcagt accaacctca ctattagtac tgtatctgca    60
caatctgcat ctgccacttt taaaccatca gattataagc agtttataag gcatggtgag   120
gaatatgaat tacagtttat attt                                          144

<210> SEQ ID NO 261
<211> LENGTH: 144
<212> TYPE: DNA
<213> ORGANISM: Human papillomavirus type 70

<400> SEQUENCE: 261
tttattactg tggtggacac tacacgtagt actaattttta cattgtctgc ctgcaccgaa    60
acggccatac ctgctgtata tagccctaca aagtttaagg aatatactag gcatgtggag   120
gaatatgatt tacaatttat attt                                          144

<210> SEQ ID NO 262
<211> LENGTH: 137
<212> TYPE: DNA
<213> ORGANISM: Human papillomavirus type 71

<400> SEQUENCE: 262
tttgtaacag ttgtgacaca tcacgtagta caaatatgtc catctgtgct accaaaactg    60
ttgagtctac atataaagcc tctagtttca tggaatattt gagacatgga gaagaatttg   120
atttgcaatt tatattt                                                  137

<210> SEQ ID NO 263
<211> LENGTH: 141
<212> TYPE: DNA
<213> ORGANISM: Human papillomavirus type 72

<400> SEQUENCE: 263
tttgtgacag ttgtagatac tactcgcagt actaatgtaa ctatttgtac tgccacagcg    60
tcctctgtat cagaatatac agcttctaat tttcgtgagt atcttcgcca cactgaggaa   120
tttgatttgc agtttatatt t                                             141

<210> SEQ ID NO 264
```

```
<211> LENGTH: 147
<212> TYPE: DNA
<213> ORGANISM: Human papillomavirus type 73

<400> SEQUENCE: 264
tttttaactg ttgtagatac tactagaagc actaatttttt ctgtatgtgt aggtacacag      60
gctagtagct ctactacaac gtatgccaac tctaatttta aggaatatttt aagacatgca    120 gaagagtttg atttacagtt tgttttt                                          147

<210> SEQ ID NO 265
<211> LENGTH: 144
<212> TYPE: DNA
<213> ORGANISM: Human papillomavirus type 74

<400> SEQUENCE: 265
tttgttacag ttgtggatac cacacgcagt actaacatga ctgtgtgtgc tcctacctca      60
caatcgcctt ctgctacata taatagttca gactacaaac aatacatgcg acatgtggag    120
gaatttgatt tgcaatttat tttt                                            144

<210> SEQ ID NO 266
<211> LENGTH: 138
<212> TYPE: DNA
<213> ORGANISM: Human papillomavirus type 81

<400> SEQUENCE: 266
tttgttacag tggtggatac taccagaagc accaatttta ctatttgcac agctacatct      60
gctgctgcag aatacaaggc ctctaactttt aaggaatttc tgcgccatac agaggaatat   120
gatttgcagt ttatttttc                                                  138

<210> SEQ ID NO 267
<211> LENGTH: 144
<212> TYPE: DNA
<213> ORGANISM: Human papillomavirus type 82

<400> SEQUENCE: 267
tttattactt gtgttgacac tactaaaagt accaatttaa ccattagcac tgctgttact      60
ccatctgttg cacaaacatt tactccagca aactttaagc agtacattag catggggaa     120 gaatatgaat tgcaatttat attt                                            144

<210> SEQ ID NO 268
<211> LENGTH: 138
<212> TYPE: DNA
<213> ORGANISM: Human papillomavirus type 83

<400> SEQUENCE: 268
tttgttacag ttgtagatac tacccgcagt accaatatta ctatttcagc tgctgctaca      60
caggctaatg aatacacagc ctctaactttt aaggaatacc tccgccacac agaggaatat   120
gacttacagg ttatattg                                                   138

<210> SEQ ID NO 269
<211> LENGTH: 138
<212> TYPE: DNA
<213> ORGANISM: Human papillomavirus type 84

<400> SEQUENCE: 269
tttgtcacgg tggtagatac cacccgcagc accaatttta ctattagtgc tgctaccaac      60
accgaatcag aatataaacc taccaatttt aaggaatacc taagacatgt ggaggaatat   120
```

<210> SEQ ID NO 270
<211> LENGTH: 144
<212> TYPE: DNA
<213> ORGANISM: Human papillomavirus type 85

<400> SEQUENCE: 270

```
tttataactg tggtagacac aacacgtagt accaatctta ccttatctac tgcaactact        60
aatccagttc catctatata tgaaccttct aaatttaagg aatacacacg ccatgtagag       120
gaatatgatt tacaatttat attt                                              144
```

<210> SEQ ID NO 271
<211> LENGTH: 138
<212> TYPE: DNA
<213> ORGANISM: Human papillomavirus type 86

<400> SEQUENCE: 271

```
tttgttactg tggtcgacac cacccgcagt actaattta ctattagtgc cgctacccag         60
aaggcctctg aatatgaccc ctctaagttt aatgaatatc taaggcatgc agaggaatat       120
gatttgcaat ttattttt                                                     138
```

<210> SEQ ID NO 272
<211> LENGTH: 138
<212> TYPE: DNA
<213> ORGANISM: Human papillomavirus type 87

<400> SEQUENCE: 272

```
tttgtaacgg ttgttgatac tactcgcagt accaattta ctattagtgc tgccactcaa         60
acaaccactg aatatgaccc cacaaagttt aaggaatatt taaggcatgt ggaggaatat       120
gatttacagt ttattttt                                                     138
```

<210> SEQ ID NO 273
<211> LENGTH: 139
<212> TYPE: DNA
<213> ORGANISM: Human papillomavirus type 89

<400> SEQUENCE: 273

```
tttgttactg tggtggatac cacccgtagt accaaccta ccatttgtgc tgcttcccag         60
tctggcacag aaatacagtt ctacacgctt taaggaatat ttaagacaca ctgaggaata       120
tgacctacag tttatattc                                                    139
```

<210> SEQ ID NO 274
<211> LENGTH: 138
<212> TYPE: DNA
<213> ORGANISM: Human papillomavirus type 90

<400> SEQUENCE: 274

```
tttgtaactg tggttgatac tacacgtagc accaatatga ctatttgtgc cacacaaaca       60
ccctctgaca catacaaggc ttccaatttt aaagagtaca tgcgccatgg cgaggaattt       120
gatttgcagt ttattttc                                                    138
```

<210> SEQ ID NO 275
<211> LENGTH: 144
<212> TYPE: DNA
<213> ORGANISM: Human papillomavirus type 91

```
<400> SEQUENCE: 275
tttgtaactg ttgtggatac aactcgcagc actaacttaa ccttgtgtgc atccactgag        60
tctgtgctac ctactacata tgacaacaca aagttcaaag aatatttaag gcatgcagaa       120
gaatttgatt tacagtttat attt                                              144

<210> SEQ ID NO 276
<211> LENGTH: 143
<212> TYPE: DNA
<213> ORGANISM: Human papillomavirus type 97

<400> SEQUENCE: 276
tttgttactg tggtggacac aacacgcagt actaatttaa cactgtgtgc ttctacacaa        60
aatggcgtag ctaccacata tgaccctaca aatataaaca gtatagtaga catgtggaag       120
agtatgattt acagtttatt ttt                                               143
```